United States Patent
Akao et al.

(10) Patent No.: US 11,160,312 B2
(45) Date of Patent: Nov. 2, 2021

(54) AEROSOL GENERATING DEVICE, AND METHOD AND PROGRAM FOR OPERATING SAME

(71) Applicant: JAPAN TOBACCO INC., Tokyo (JP)

(72) Inventors: Takeshi Akao, Tokyo (JP); Kazuma Mizuguchi, Tokyo (JP); Hajime Fujita, Tokyo (JP)

(73) Assignee: JAPAN TOBACCO INC., Tokyo (JP)

( * ) Notice: Subject to any disclaimer, the term of this patent is extended or adjusted under 35 U.S.C. 154(b) by 0 days.

(21) Appl. No.: 17/128,232

(22) Filed: Dec. 21, 2020

(65) Prior Publication Data
US 2021/0106064 A1 Apr. 15, 2021

Related U.S. Application Data

(63) Continuation of application No. PCT/JP2018/023735, filed on Jun. 22, 2018.

(51) Int. Cl.
*A24F 40/57* (2020.01)
*A24F 40/53* (2020.01)
*A24F 40/51* (2020.01)
*A61M 15/06* (2006.01)

(52) U.S. Cl.
CPC .............. *A24F 40/57* (2020.01); *A24F 40/51* (2020.01); *A24F 40/53* (2020.01); *A61M 15/06* (2013.01)

(58) Field of Classification Search
CPC ........ A61M 15/96; A61M 15/06; A24F 40/57
See application file for complete search history.

(56) References Cited

U.S. PATENT DOCUMENTS

2014/0345606 A1* 11/2014 Talon .................. A61M 16/024
128/202.21
2017/0245551 A1 8/2017 Reevell

FOREIGN PATENT DOCUMENTS

| JP | 2013-517493 A | 5/2013 |
| JP | 2014-501105 A | 1/2014 |
| WO | 2017/024477 A1 | 2/2017 |
| WO | 2017/084818 A1 | 5/2017 |
| WO | 2017/144191 A1 | 8/2017 |
| WO | 2017/144374 A1 | 8/2017 |

(Continued)

OTHER PUBLICATIONS

English Machine translation of WO 2017/185355A1 Quiming et al. (Year: 2017).*

(Continued)

*Primary Examiner* — Anthony Calandra
(74) *Attorney, Agent, or Firm* — Xsensus LLP

(57) ABSTRACT

Provided is an aerosol generating device that can accurately detect the shortage or exhaustion of an aerosol source at low cost. The aerosol generating device includes: a reservoir that stores an aerosol source or an aerosol base that holds an aerosol source; a load that atomizes the aerosol source with heat generated by using power supplied from a power source; a sensor that outputs a value related to the temperature of the load; and a control unit configured to determine the occurrence of exhaustion of the aerosol source in the reservoir or the aerosol base on the basis of the cooling velocity derived from the output value of the sensor in a cooling process after the load has been heated to a temperature higher than or equal to a temperature at which the aerosol source can be atomized.

13 Claims, 36 Drawing Sheets

(56) References Cited

FOREIGN PATENT DOCUMENTS

WO 2017/185355 A1 11/2017
WO 2017/185356 A1 11/2017

OTHER PUBLICATIONS

International Search Report and Written Opinion dated Aug. 28, 2018, received for PCT Application No. PCT/JP2018/023735, Filed on Jun. 22, 2018, 8 pages including English Translation.
Chinese Office Action dated Jun. 30, 2021 in Chinese Patent Application No. 201880095834.1.

* cited by examiner

Fig. 31

| METALS | Al | Ti | Zr | Ta | Zn | Cr | Fe | Ni | Pb | Cu | Ag | Pt | Au |
|---|---|---|---|---|---|---|---|---|---|---|---|---|---|
| OXIDATION-REDUCTION POTENTIAL (V) | −1.676 | −1.630 | −1.534 | −0.810 | −0.763 | −0.740 | −0.440 | −0.257 | −0.126 | 0.340 | 0.799 | 1.188 | 1.520 |
| EASE OF FORMING OXIDE FILM | FORMED (* PARTICULARLY EASILY FORMED AT HIGH TEMPERATURE) | | | | | | | | | | LESS LIKELY TO BE FORMED | NOT FORMED | |

PREFERRED METALS FOR USE IN LOAD (HEATER): Al, Ti, Zr, Ta, Zn, Cr, Fe, Ni, Pb, Cu

3100

AEROSOL GENERATING DEVICE, AND METHOD AND PROGRAM FOR OPERATING SAME

CROSS REFERENCE TO RELATED APPLICATION

The present application is a continuation application of International Application No. PCT/JP2018/023735, filed on Jun. 22, 2018, the entire contents of which are incorporated herein by reference.

TECHNICAL FIELD

The present disclosure relates to an aerosol generation device that generates aerosol to be inhaled by a user, and a method and a program for operating the same.

BACKGROUND ART

In an aerosol generation device such as a general electronic cigarette, a heated cigarette, or nebulizer, the aerosol generation device being configured to generate aerosol to be inhaled by a user, if the user performs inhalation when an aerosol source to be atomized to generate the aerosol is insufficient in quantity, a sufficient quantity of aerosol cannot be supplied to the user. In addition, in the case of the electronic cigarette or the heated cigarette, there may be a problem in that the aerosol having an unintended inhaling flavor may be released.

As a solution to this problem, PTL 1 discloses a technique for detecting depletion of an aerosol source based on a time period required when a temperature of a heater decreases from a certain temperature to another temperature by cooling of the heater. PTLs 2 to 5 also disclose various techniques that solve the above-described problem or may contribute to solve the above-described problem.

These techniques are in the process of development. There is a need for a technique that makes it possible to observe a cooling process of a heater of an aerosol generation device at a low cost and with high accuracy, a technique that makes it possible to detect insufficiency and depletion of an aerosol source in the aerosol generation device at a low cost and with high accuracy, and the other techniques. Note that the cooling process of the heater is affected according to a state of the aerosol generation device. Accordingly, since the state of the aerosol generation device can be known by observing the cooling process of the heater, there is further need for a technique that makes it possible to observe the cooling process of the heater of the aerosol generation device at a low cost and with high accuracy.

CITATION LIST

Patent Literature

PTL 1: International Publication No. WO 2017/185355
PTL 2: international Publication No. WO 20171185356
PTL 3: International Publication No. WO 2017/024477
PTL 4: International Publication No. WO 2017/144191
PTL 5: International Publication No. WO 2017/084818

SUMMARY OF INVENTION

Technical Problem

The present disclosure has been devised in view of the point described above.

A first problem to be solved by the present disclosure is to provide an aerosol generation device capable of observing a cooling process of a heater at a low cost and with high accuracy, and further capable of detecting insufficiency or depletion of an aerosol source at a low cost and with high accuracy, and a method and a program for operating the same.

A second problem to be solved by the present disclosure is to provide an aerosol generation device capable of detecting insufficiency or depletion of an aerosol source at a low cost and with high accuracy, and a method and a program for operating the same.

A third problem to be solved by the present disclosure is to provide an aerosol generation device capable of detecting insufficiency or depletion of an aerosol source at a low cost and with high accuracy, and a method and a program for operating the same.

Solution to Problem

In order to solve the first problem described above, according to a first embodiment of the present disclosure, there is provided an aerosol generation device comprising a storage unit that stores an aerosol source or an aerosol base material that retains the aerosol source, a load that generates heat upon receipt of power supply from a power source and atomizes the aerosol source, and in which a value of an electric resistance changes in response to a temperature, a sensor that detects the value of the electric resistance of the load or an electric value related to the electric resistance, and a control unit configured to monitor a cooling process of the load after a temperature of the load increases up to a temperature in which the aerosol source can be atomized or higher, based on a time-series change in a value detected by the sensor, in a manner that retains a correlation between the time-series change in the value detected by the sensor and a decrease in the temperature of the load.

In an embodiment, the control unit is configured to control the power supply from the power source to the load based on a request for aerosol generation. At least one of a time period from an end of the power supply to a start of monitoring of the cooling process and a cycle in which the sensor detects the value of the electric resistance or the electric value related to the electric resistance is larger than a minimum value achievable by the control unit.

In an embodiment, the control unit is configured to determine, based on the cooling process, whether depletion of the aerosol source in the storage unit or the aerosol base material has occurred.

In an embodiment, the control unit is configured to provide a dead zone in which the cooling process is not monitored or determination, based on the monitored cooling process, as to whether the depletion has occurred is not made, when or immediately after the cooling process starts.

In an embodiment, the control unit is configured to control the power supply from the power source to the load, based on a request for aerosol generation. The dead zone is provided until a current value of at least one of a residual current and a surge current that are generated at the end of the power supply becomes equal to or smaller than a threshold.

In an embodiment, a time period of the dead zone is shorter than a time period until the cooling process is completed in a state in which the depletion of the aerosol source does not occur.

In an embodiment, the control unit is configured to control the power supply from the power source to the load based on a request for aerosol generation, and cause the sensor to detect the value related to the electric resistance value during monitoring of the cooling process in a cycle longer than a time period required until a current value of at least one of a residual current and a surge current that are generated at the end of the power supply becomes equal to or smaller than a threshold.

In an embodiment, the control unit is configured to shorten in a stepped manner the cycle in which the value of the electric resistance or the electric value related to the electric resistance is detected by the sensor during monitoring of the cooling process.

In an embodiment, the control unit is configured to shorten the cycle in which the value of the electric resistance or the electric value related to the electric resistance is detected by the sensor during monitoring of the cooling process, as the temperature of the load corresponding to the value detected by the sensor is low.

In an embodiment, the control unit is configured to correct the value detected by the sensor when or immediately after the cooling process starts by smoothing the time-series change in the value detected by the sensor, and monitor the cooling process based on the corrected value.

In an embodiment, the control unit is configured to correct the value detected by the sensor using at least one of an average process and a low-pass filter.

In an embodiment, the control unit is configured to determine whether the depletion of the aerosol source has occurred, based on the cooling process until the value detected by the sensor reaches a steady state.

In an embodiment, the control unit is configured to control the power supply from the power source to the load based on a request for aerosol generation, and determine whether the value detected by the sensor has reached the steady state, based on a comparison between the value detected by the sensor before the power supply is performed and a value detected by the sensor in the cooling process.

In an embodiment, the control unit is configured to determine whether the value detected by the sensor has reached the steady state based on a comparison between the value detected by the sensor corresponding to a temperature higher than a room temperature by a predetermined value and the value detected by the sensor in the cooling process.

In an embodiment, the predetermined value is larger than an error in the temperature of the load obtained from the value detected by the sensor, the error being caused by an error of the sensor.

In an embodiment, the control unit is configured to determine whether the value detected by the sensor has reached the steady state, based on a time differential value of the value detected by the sensor.

In an embodiment, the control unit is configured to determine whether the value detected by the sensor has reached the steady state, based on deviation, or variance of the value detected by the sensor.

In addition, according to the first embodiment of the present disclosure, there is provided a method of operating an aerosol generation device, the method comprising generating heat upon receipt of power supply to a load having an electric resistance value that changes in response to a temperature and atomizing an aerosol source, detecting a value of an electric resistance of the load or an electric value related to the electric resistance, and monitoring a cooling process after a temperature of the load increases up to a temperature in which the aerosol source can be atomized or higher, based on a time-series change in the detected value, in a manner that retains a correlation between the time-series change in the value detected by the sensor and a decrease in the temperature of the load.

In addition, according to the first embodiment of the present disclosure, there is provided an aerosol generation device comprising a storage unit that stores an aerosol source or an aerosol base material that retains the aerosol source, a load that generates heat upon receipt of power supply from a power source and atomizes the aerosol source, and in which a value of an electric resistance changes in response to a temperature, a sensor that detects the value of the electric resistance of the load or an electric value related to the electric resistance, and a control unit configured to monitor a cooling process after a temperature of the load increases up to a temperature in which the aerosol source can be atomized or higher, based on a time-series change in a value detected by the sensor. The control unit is configured to cause the sensor to detect the value during monitoring of the cooling process at timing when the temperature of the load does not diverge from the value of the electric resistance of the load or the electric value related to the electric resistance, or with a frequency that does not interfere with cooling of the load in the cooling process.

In addition, according to the first embodiment of the present disclosure, there is provided a method of operating an aerosol generation device, the method comprising generating heat upon receipt of power supply to a load having an electric resistance value that changes in response to a temperature and atomizing an aerosol source, detecting a value of an electric resistance of the load or an electric value related to the electric resistance, and monitoring a cooling process after a temperature of the load increases up to a temperature in which the aerosol source can be atomized or higher, based on a time-series change in the detected value, wherein the value is detected during monitoring of the cooling process at timing when the temperature of the load does not diverge from the value of the electric resistance of the load or the electric value related to the electric resistance, or with a frequency that does not interfere with cooling of the load in the cooling process.

In addition, according to the first embodiment of the present disclosure, there is provided an aerosol generation device comprising a storage unit that stores an aerosol source or an aerosol base material that retains the aerosol source, a load that generates heat upon receipt of power supply from a power source and atomizes the aerosol source, and in which a value of an electric resistance changes in response to a temperature, a sensor that detects the value of the electric resistance of the load or an electric value related to the electric resistance, and a control unit configured to monitor a cooling process after a temperature of the load increases up to a temperature in which the aerosol source can be atomized or higher, based on a time-series change in a value detected by the sensor. The control unit is configured to determine whether depletion of the aerosol source in the storage unit has occurred, based on the time-series change in the value detected by the sensor in the cooling process after a point when or immediately after cooling of the load starts and before a point when the load reaches a room temperature.

In an embodiment, the control unit is configured to determine whether the value detected by the sensor has reached a steady state, based on the value detected by the sensor or the time-series change in the value, and determine whether the depletion has occurred, based on the cooling process until the value detected by the sensor reaches the steady state.

In addition, according to the first embodiment of the present disclosure, there is provided a method of operating an aerosol generation device, the method comprising generating heat upon receipt of power supply to a load having an electric resistance value that changes in response to a temperature and atomizing an aerosol source, detecting a value of an electric resistance of the load or an electric value related to the electric resistance, and monitoring a cooling process after a temperature of the load increases up to a temperature in which the aerosol source can be atomized or higher, based on a time-series change in the detected value. It is determined whether depletion of the aerosol source has occurred, based on the time-series change in the detected value in the cooling process after a point when or immediately after cooling of the load starts and before a point when the load reaches a room temperature.

According to the first embodiment of the present disclosure, there is provided a program for, when being executed by a processor, causing the processor to perform any of the above-described methods.

In order to solve the second problem described above, according to a second embodiment of the present disclosure, there is provided an aerosol generation device comprising a storage unit that stores an aerosol source or an aerosol base material that retains the aerosol source, a load that generates heat upon receipt of power supply from a power source and atomizes the aerosol source, a sensor that outputs a value related to a temperature of the load, and a control unit configured to determine whether depletion of the aerosol source in the storage unit or the aerosol base material has occurred, based on a cooling rate derived from the output value of the sensor in a cooling process after the temperature of the load increases up to a temperature in which the aerosol source can be atomized or higher.

In an embodiment, the control unit is configured to determine whether the depletion has occurred based on the cooling rate in a time zone in which a difference between the cooling rate when the depletion of the aerosol source occurs and the cooling rate when the depletion of the aerosol source does not occur is equal to or larger than a threshold, in the cooling process.

In an embodiment, the control unit is configured to determine whether the depletion has occurred, based on the cooling rate in a time zone in which the temperature of the load belongs to a temperature range achievable only when the depletion occurs, in the cooling process.

In an embodiment, the control unit is configured to derive the cooling rate from a plurality of output values of the sensor and acquire at least an earliest value in terms of a time axis among the plurality of output values of the sensor, in a time zone in which the temperature of the load belongs to a temperature range achievable only when the depletion occurs, in the cooling process.

In an embodiment, the control unit is configured to acquire the plurality of output values of the sensor in the time zone in which the temperature of the load belongs to the temperature range achievable only when the depletion occurs, in the cooling process.

In an embodiment, the load has an electric resistance value that changes in response to a temperature, and the sensor outputs the value related to the electric resistance value as a value related to the temperature of the load.

In an embodiment, the control unit is configured to provide a dead zone in which the value related to the electric resistance value is not acquired by the sensor or the cooling rate is not derived, when or immediately after the cooling process starts. Alternatively, the control unit is configured to derive the cooling rate based on the output value of the sensor when or immediately after the cooling process starts, the output value being corrected by smoothing a time-series change in the output value of the sensor.

In an embodiment, the control unit is configured to control the power supply from the power source to the load so that the electric power supplied from the power supply to the load before the cooling process decreases in a stepped manner or decreases gradually.

In an embodiment, the control unit is configured to control the power supply from the power source to the load based on a request for aerosol generation. The dead zone is provided to continue until a current value of at least one of a residual current and a surge current that are generated at the end of the power supply becomes equal to or smaller than a threshold.

In an embodiment, the dead zone is shorter than a time period until the cooling process is completed in a case where the depletion does not occur.

In an embodiment, the aerosol generation device includes a first circuit that is connected in series between the power source and the load and includes a first switch, and a second circuit that is connected in series between the power source and the load, is connected in parallel to the first circuit, includes a second switch, and has an electric resistance value larger than the electric resistance value of the first circuit. The control unit is configured to control the first switch and the second switch, and derive the cooling rate based on the output value of the sensor while only the second switch of the first switch and the second switch is on.

In an embodiment, the control unit is configured to turn on the second switch immediately before the cooling process.

In an embodiment, at least one of a time period from the end of the power supply to a start of acquisition of the value related to the electric resistance value by the sensor and a cycle in which the sensor acquires the value related to the electric resistance value is larger than the minimum value achievable by the control unit.

In addition, according to the second embodiment of the present disclosure, there is provided a method of operating an aerosol generation device, the method comprising generating heat upon receipt of power to a load and atomizing an aerosol source, detecting a value related to a temperature of the load, and determining whether depletion of the aerosol source has occurred, based on a cooling rate derived from the detected value, in a cooling process after a temperature of the load increases up to a temperature in which the aerosol source can be atomized or higher.

According to the second embodiment of the present disclosure, there is provided a program for, when being executed by a processor, causing the processor to perform the above-described methods.

In order to solve the third problem described above, according to a third embodiment of the present disclosure, there is provided an aerosol generation device comprising a storage unit that stores an aerosol source or an aerosol base material that retains the aerosol source, a load that generates heat upon receipt of power supply from a power source and atomizes the aerosol source, and of which physical properties change when the load is heated at a temperature achievable only when depletion of the aerosol source in the storage unit or the aerosol base material occurs, a sensor that outputs a value related to the physical properties of the load, and a control unit configured to determine whether the depletion has occurred, based on the output value of the sensor after a temperature of the load increases up to a temperature in which the aerosol source can be atomized or higher.

In an embodiment, the control unit is configured to determine whether the depletion has occurred, based on a steady value that is the output value of the sensor in a steady state after the temperature of the load increases up to a temperature in which the aerosol source can be atomized or higher.

In an embodiment, the control unit is configured to be capable of acquiring a request for aerosol generation, and acquire the steady value taking opportunity of the acquisition of the request.

In an embodiment, the control unit is configured to determine whether the depletion has occurred, based on an amount of change in the output value of the sensor before and after the temperature of the load increases up to a temperature in which the aerosol source can be atomized or higher.

In an embodiment, the control unit is configured to determine whether the depletion has occurred, based on a difference in the output value of the sensor before and after the temperature of the load increases up to a temperature in which the aerosol source can be atomized or higher.

In an embodiment, the control unit is configured to prohibit the aerosol source from being atomized by the load until the output value of the sensor reaches the steady state after the temperature of the load increases up to a temperature in which the aerosol source can be atomized or higher.

In an embodiment, the control unit is configured to determine whether the depletion has occurred, based on a comparison between the output value of sensor before reaching the steady state and a value obtained by adding a predetermined value to the value related to the physical properties of the load in the steady state when the depletion has occurred or based on a comparison between a value obtained by subtracting the predetermined value from the output value of the sensor before reaching the steady state and the value related to the physical properties of the load in the steady state when the depletion has occurred, in the cooling process after the temperature of the load increases up to a temperature in which the aerosol source can be atomized or higher.

In an embodiment, the load has an electric resistance value that changes in response to a temperature. The sensor outputs the value related to the electric resistance value of the load as a value related to the physical properties of the load.

In an embodiment, the control unit is configured to determine whether the depletion has occurred, based on a comparison between the output value of the sensor after the temperature of the load increases up to a temperature in which the aerosol source can be atomized or higher and a value related to the resistance value of the load when a protective film is formed on a surface of the load.

In an embodiment, the control unit is configured to determine whether the depletion has occurred, based on a comparison between an amount of change in the output value of the sensor before and after the temperature of the load increases up to a temperature in which the aerosol source can be atomized or higher and an amount of change in the value related to the resistance value of the load due to the protective film formed on the surface of the load.

In an embodiment, the load contains metals having oxidation-reduction potentials equal to or lower than the oxidation-reduction potential of copper.

In an embodiment, the load has no passivation film.

In an embodiment, the load contains NiCr.

In an embodiment, the aerosol generation device further includes a first circuit that is connected in series between the power source and the load and includes a first switch, and a second circuit that is connected in series between the power source and the load, is connected in parallel to the first circuit, includes the second switch, and has an electric resistance value larger than the electric resistance value of the first circuit. The control unit is configured to control the first switch and the second switch, and determine whether the depletion has occurred based on the output value of the sensor while only the second switch of the first switch and the second switch is on.

In addition, according to the third embodiment of the present disclosure, there is provided a method of operating an aerosol generation device that includes a load of which physical properties change when the load is heated at a temperature achievable only when depletion of the aerosol source occurs, the method comprising detecting a value related to the physical properties of the load, and determining whether the depletion of the aerosol source has occurred, based on the detected value after a temperature of the load increases up to a temperature in which the aerosol source can be atomized or higher.

According to the third embodiment of the present disclosure, there is provided a program for, when being executed by a processor, causing the processor to perform the above-described methods.

Advantageous Effects of Invention

According to the first embodiment of the present disclosure, there can be provided an aerosol generation device capable of observing a cooling process of a heater at a low cost and with high accuracy, and further capable of detecting insufficiency or depletion of an aerosol source at a low cost and with high accuracy, and a method and a program for operating the same.

According to the second embodiment of the present disclosure, there can be provided an aerosol generation device capable of detecting insufficiency or depletion of an aerosol source at a low cost and with high accuracy, and a method and a program for operating the same.

According to the third embodiment of the present disclosure, there can be provided an aerosol generation device capable of detecting insufficiency or depletion of an aerosol source at a low cost and with high accuracy, and a method and a program for operating the same.

BRIEF DESCRIPTION OF DRAWINGS

FIG. 30 is a flowchart of processing according to an embodiment of the present disclosure, in connection with FIG. 29.

FIG. 31 shows a table indicating oxidation-reduction potentials and the ease of forming an oxide film of various metals that can be used for manufacturing of the load.

FIG. 32 conceptually shows a method of determining whether the depletion of the aerosol source has occurred, in an embodiment of the present disclosure.

FIG. 33 is a flowchart of processing according to an embodiment of the present disclosure, in connection with FIG. 32.

FIG. 34 conceptually shows a method of determining whether the depletion of the aerosol source has occurred, in an embodiment of the present disclosure.

FIG. 35 is a flowchart of processing according to an embodiment of the present disclosure, in connection with FIG. 32.

DESCRIPTION OF EMBODIMENTS

Hereinafter, embodiments of the present disclosure will be described in detail with reference to the drawings. Note that the embodiments of the present disclosure include an electronic cigarette, a heated cigarette, and a nebulizer, but are not limited to the electronic cigarette, the heated cigarette, and the nebulizer. The embodiments of the present disclosure can include various aerosol generation devices for generating aerosol to be inhaled by a user.

FIG. 1A is a schematic block diagram of a configuration of an aerosol generation device 100A according to an embodiment of the present disclosure. It should be noted that FIG. 1A schematically and conceptually illustrates components included in the aerosol generation device 100A and does not illustrate strict disposition, shapes, dimensions, positional relations, and the like of the components and the aerosol generation device 100A.

As illustrated in FIG. 1A, the aerosol generation device 100A includes a first member 102 (hereinafter, referred to as a "main body 102") and a second member 104A (hereinafter, referred to as a "cartridge 104A"). As illustrated in the figure, as an example, the main body 102 may include a control unit 106, a notifying unit 108, a power source 110, a sensor 112, and a memory 114. The aerosol generation device 100A may include sensors such as a flow sensor, a pressure sensor, a voltage sensor, an electric resistance sensor, and a temperature sensor, and these sensors are collectively referred to as the "sensor 112" in the present disclosure. The main body 102 may also include a circuit 134 described later. As an example, the cartridge 104A may include a storage unit 116A, an atomizing unit 118A, an air intake channel 120, an aerosol flow path 121, a mouthpiece unit 122, a retention unit 130, and a load 132. Some of the components included in the main body 102 may be included in the cartridge 104A. Some of the components included in the cartridge 104A may be included in the main body 102. The cartridge 104A may be configured to be detachably attached to the main body 102. Alternatively, all the components included in the main body 102 and the cartridge 104A may be included in the same housing instead of the main body 102 and the cartridge 104A.

Figure 1A:
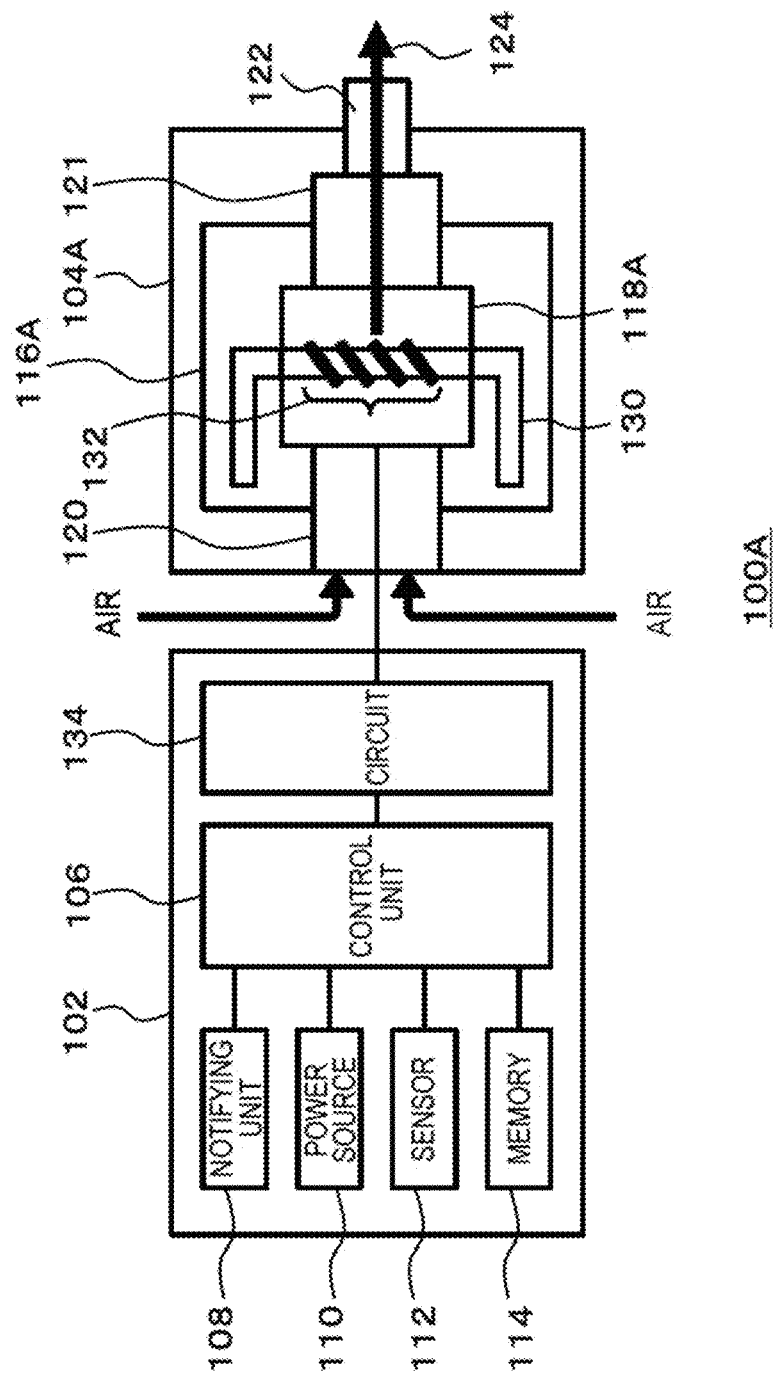
FIG. 1A is a schematic block diagram of a configuration of an aerosol generation device according to an embodiment of the present disclosure.

The storage unit 116A may be configured as a tank that stores an aerosol source. In this case, the aerosol source is liquid, for example, polyalcohol such as glycerin or propylene glycol, or water. When the aerosol generation device 100A is an electronic cigarette, the aerosol source in the storage unit 116A may include a tobacco raw material that emits an inhaling flavor component by being heated or an extract deriving from the tobacco raw material. The retention unit 130 retains the aerosol source. For example, the retention unit 130 is formed of a fibrous or porous material, and retains the aerosol source, which is liquid, in gaps among fibers or thin holes of a porous material. For example, cotton, glass fiber, a tobacco raw material or the like can be used as the above-mentioned fibrous or porous material. When the aerosol generation device 100A is a medical inhaler such as a nebulizer, the aerosol source may also include a drug to be inhaled by a patient. As another example, the storage unit 116A may have a configuration in which a consumed aerosol source can be replenished. Alternatively, the storage unit 116A itself may be configured to be replaceable when the aerosol source is consumed. The aerosol source is not limited to liquid, and may be solid. When the aerosol source is solid, the storage unit 116A may be a hollow container.

The atomizing unit 118A is configured to atomize the aerosol source and generate aerosol. When an inhaling operation is detected by the sensor 112, the atomizing unit 118A generates the aerosol. For example, the inhaling operation may be detected by the flow sensor or a flow rate sensor. In this case, if an absolute value or an amount of change of a flow rate or a flow velocity of air in the air intake channel 120 satisfies a predetermined condition, the air being generated in the air intake channel 120 when the user holds the mouthpiece unit 112 in the user's mouth and performs the inhalation, the flow sensor or the flow rate sensor may detect the inhaling operation. Alternatively, for example, the inhaling operation may be detected by the pressure sensor. In this case, if a predetermined condition is satisfied such as the pressure inside the air intake channel 120 becomes negative when the user holds the mouthpiece unit 112 in the user's mouth and performs the inhalation, the pressure sensor may detect the inhaling operation. Note that the flow sensor, the flow rate sensor and the pressure sensor may be configured to only output a flow rate, a flow velocity, and a pressure in the air intake channel 120, respectively, so that the control unit 106 detects the inhaling operation based on the output.

Alternatively, the atomizing unit 118A may generate the aerosol or the atomizing unit 118A may receive the electric power from the power source 110 with the use of, for example, a push button, a touch panel, or an acceleration sensor, so that it is unnecessary to detect the inhaling operation or wait detection of the inhaling operation. Such a configuration enables the atomizing unit 118A to appropriately generate the aerosol at timing when the user actually inhales the aerosol even when the thermal capacity of the retention unit 130 and the load 132 that form the atomizing unit 118A or the thermal capacity of the aerosol source itself is large, for example. Note that the sensor 112 may include a sensor that detects the operation on the push button or the touch panel, or the acceleration sensor.

For example, the retention unit 130 is provided to couple the storage unit 116A and the atomizing unit 118A. In this case, a part of the retention unit 130 communicates with the inside of the storage unit 116A and is in contact with the aerosol source. Another part of the retention unit 130 extends to the atomizing unit 118A. Note that the other part of the retention unit 130 extending to the atomizing unit 118A may be accommodated in the atomizing unit 118A, or may communicate with the inside of the storage unit 116A again through the atomizing unit 118A. The aerosol source is carried from the storage unit 116A to the atomizing unit 118A by a capillary effect of the retention unit 131). As an example, the atomizing unit 118A includes a heater including the load 132 that is electrically connected to the power source 110. The heater is disposed in contact with or in close contact with the retention unit 130. When an inhaling operation is detected, the control unit 106 controls the heater of the atomizing unit 118A or the power supply to the heater, and heats the aerosol source carried through the retention unit 130 to thereby atomize the aerosol source. Another example of the atomizing unit 118A may be an ultrasonic atomizer that atomizes the aerosol source by ultrasonic vibration. The air intake channel 120 is connected to the atomizing unit 118A, and communicates with the outside of the aerosol generation device 100A. The aerosol generated in the atomizing unit 118A is mixed with air taken in via the air intake channel 120. Mixed fluid of the aerosol and the air is delivered to the aerosol flow path 121 as indicated by an arrow 124. The aerosol flow path 121 has a tubular structure for transporting, to the mouthpiece unit 122, the mixed fluid of the aerosol generated in the atomizing unit 118A and the air.

The mouthpiece unit 122 is located at a terminal end of the aerosol flow path 121, and is configured to open the aerosol flow path 121 to the outside of the aerosol generation device 100A. The user holds the mouthpiece unit 122 in the user's mouth and performs the inhalation to thereby take the air containing the aerosol in the user's mouth.

The notifying unit 108 may include a light emitting element such as an LED, a display, a speaker, a vibrator, or the like. The notifying unit 108 is configured to perform some notification to the user with light emission, display, sound production, vibration, or the like according to necessity.

The power source 110 supplies electric power to the components such as the notifying unit 108, the sensor 112, the memory 114, the load 132, and the circuit 134 of the aerosol generation device 100A. The power source 110 can also be charged by being connected to an external power source via a predetermined port (not illustrated) of the aerosol generation device 100A. Only the power source 110 may be detachable from the main body 102 or the aerosol generation device 100A, or may be replaceable with a new power source 110. The power source 110 may be replaceable with a new power source 110 by replacing the entire main body 102 with a new main body 102.

The sensor 112 may also include one or more sensors that are used to acquire a value of a voltage applied to all or a specific portion in the circuit 134, a value related to a resistance value of the load 132 or a value related to a temperature of the load 132, or the like. The sensor 112 may be incorporated in the circuit 134. The function of the sensor 112 may be incorporated in the control unit 106. The sensor 112 may also include the pressure sensor that detects fluctuation in pressure in the air intake channel 120 and/or the aerosol flow path 121 or the flow sensor that detects a flow rate in the air intake channel 120 and/or the aerosol flow path 121. The sensor 112 may also include a weight sensor that detects a weight of a component such as the storage unit 116A. The sensor 112 may be also configured to count the number of times that the user puffs using the aerosol generation device 100A. The sensor 112 may be also configured to integrate an energization time to the atomizing unit 118A. The sensor 112 may be also configured to detect a height of a liquid surface in the storage unit 116A. The control unit 106 and the sensor 112 may be also configured to obtain or detect an SOC (State of Charge), a current integrated value, a voltage and the like of the power source 110. The SOC may be obtained by a current integration method (coulomb counting method), an SOC-OCV (Open Circuit Voltage) method, or the like. The sensor 112 may be also an operation button or the like that is operable by the user.

The control unit 106 may be an electronic circuit module configured as a microprocessor or a microcomputer. The control unit 106 may be also configured to control the operation of the aerosol generation device 100A according to computer executable instructions stored in the memory 114. The memory 114 is a storage medium such as a ROM, a RAM or a flash memory. In the memory 114, in addition to the above-mentioned computer executable instructions, setting data required for controlling the aerosol generation device 100A and the like may be stored. For example, the memory 114 may store various pieces of data such as a control program of the notifying unit 108 (aspects, etc. of light emission, sound production, vibration, etc.), a control program of the atomizing unit 118A, a value acquired and/or detected by the sensor 112, and a heating history of the atomizing unit 118A. The control unit 106 reads the data from the memory 114 according to necessity to use it for control of the aerosol generation device 100A, and stores the data in the memory 114 according to necessity.

Figure 1B:
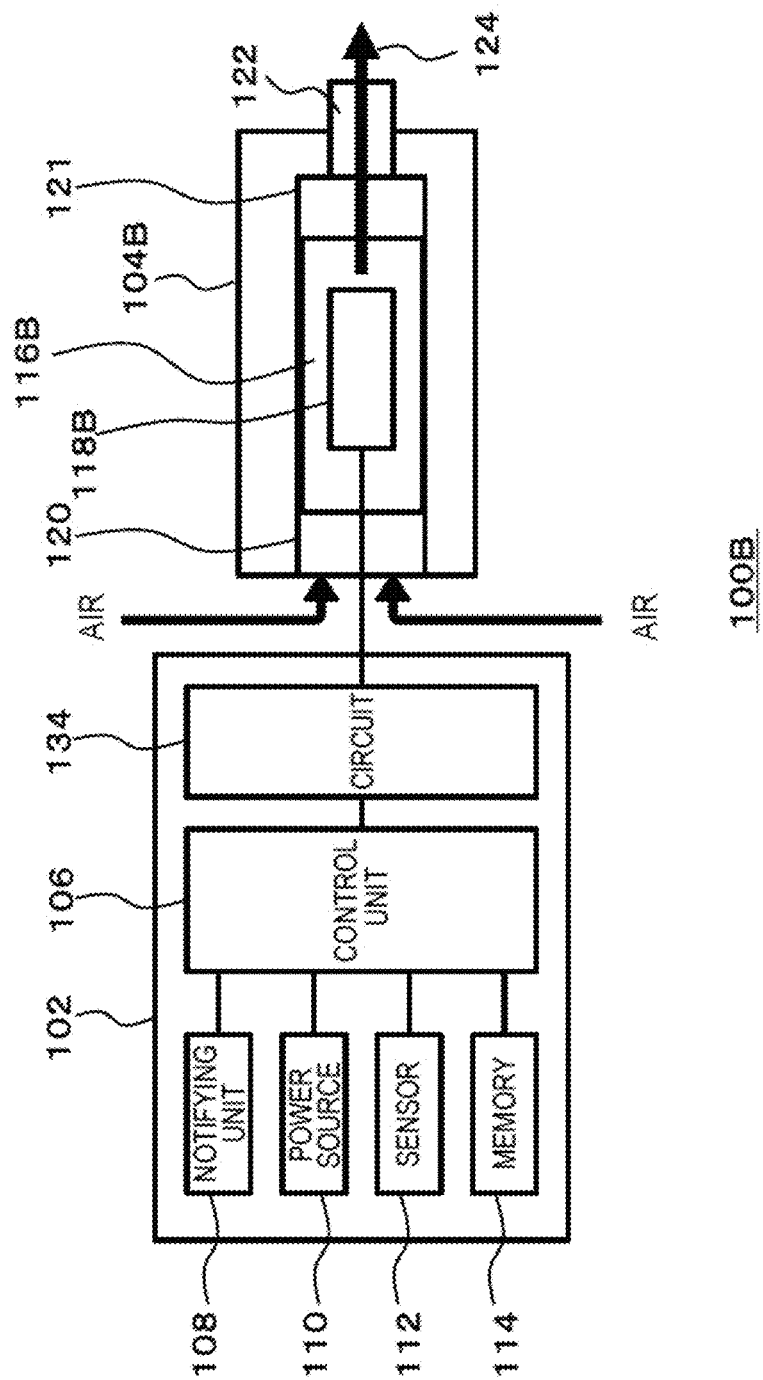
FIG. 1B is a schematic block diagram of a configuration of an aerosol generation device according to an embodiment of the present disclosure.

FIG. 1B is a schematic block diagram of a configuration of an aerosol generation device 100B according to an embodiment of the present disclosure.

As illustrated in the figure, the aerosol generation device 100B has a configuration similar to that of the aerosol generation device 100A of FIG. 1A. Note that a configuration of a second member 104B (hereinafter, referred to as an "aerosol generating article 104B" or a "stick 104B") is different from that of the first member 104A. As an example, the aerosol generating article 104B may include an aerosol base material 116B, an atomizing unit 118B, an air intake channel 120, an aerosol flow path 121, and a mouthpiece unit 122. Some of the components included in the main body 102 may be included in the aerosol generating article 104B. Some of the components included in the aerosol generating article 104B may be included in the main body 102. The aerosol generating article 104E may be configured to be insertable/extractable into/from the main body 102. Alternatively, all the components included in the main body 102 and the aerosol generating article 104B may be included in the same housing instead of the main body 102 and the aerosol generating article 104B.

The aerosol base material 116B may be configured as a solid carrying the aerosol source. As in the case of the storage unit 116A in FIG. 1A, the aerosol source may be liquid, for example, polyalcohol such as glycerin or propylene glycol, or water. The aerosol source in the aerosol base material 116B may include a tobacco raw material that emits an inhaling flavor component by being heated or an extract deriving from the tobacco raw material. When the aerosol generation device 100A is a medical inhaler such as a nebulizer, the aerosol source may also include a drug to be inhaled by a patient. The aerosol base material 116B itself may be configured to be replaceable when the aerosol source is consumed. The aerosol source is not limited to liquid, and may be a solid.

The atomizing unit 118B is configured to atomize the aerosol source and generate aerosol. When an inhaling operation is detected by the sensor 112, the atomizing unit 118B generates the aerosol. The atomizing unit 118B includes a heater (not illustrated) including a load that is electrically connected to the power source 110. When an inhaling operation is detected, the control unit 106 controls the heater of the atomizing unit 118B or the power supply to the heater, and heats the aerosol source carried in the aerosol base material 116B to thereby atomize the aerosol source. Another example of the atomizing unit 118B may be an ultrasonic atomizer that atomizes the aerosol source by ultrasonic vibration. The air intake channel 120 is connected to the atomizing unit 118B, and communicates with the outside of the aerosol generation device 100B. The aerosol generated in the atomizing unit 118E is mixed with air taken in via the air intake channel 120. Mixed fluid of the aerosol and the air is delivered to the aerosol flow path 121 as indicated by an arrow 124. The aerosol flow path 121 has a tubular structure for transporting, to the mouthpiece unit 122, the mixed fluid of the aerosol generated in the atomizing unit 118B and the air. Note that in the aerosol generation device 100B, the aerosol generating article 104B is configured to be heated from the inside by the atomizing unit 118B that is located in the aerosol generating article 104B or is inserted into the inside of the aerosol generating article 104B. Alternatively, the aerosol generating article 104B may be also configured to be heated from the outside by the atomizing unit 118B configured to surround or accommodate the aerosol generating article 104B.

The control unit 106 is configured to control the aerosol generation devices 100A and 100B (hereinafter also generically referred to as an "aerosol generation device 100") according to the embodiment of the present disclosure in various methods.

In the aerosol generation device, if the user performs the inhalation when the aerosol source is insufficient in quantity, a sufficient quantity of aerosol cannot be supplied to the user. In addition, in the case of the electronic cigarette or the heated cigarette, the aerosol having an unintended inhaling flavor may be emitted (hereinafter, such a phenomenon is also referred to as "unintended behavior"). The inventors of the present application have invented an aerosol generation device that performs an appropriate control when an aerosol source is depleted or insufficient in quantity, and a method and a program for operating the same, Hereinafter, each embodiment of the present disclosure will be described in detail, while mainly assuming the case where the aerosol generation device has a configuration illustrated in FIG. 1A. However, the case where the aerosol generation device has a configuration illustrated in FIG. 1B is also described according to necessity. It will be apparent to those skilled in the art that the embodiment of the present disclosure is also applicable to the case where the aerosol generation device has various configurations other than those illustrated in FIG. 1A and FIG. 1B.

First Embodiment

Figure 2:
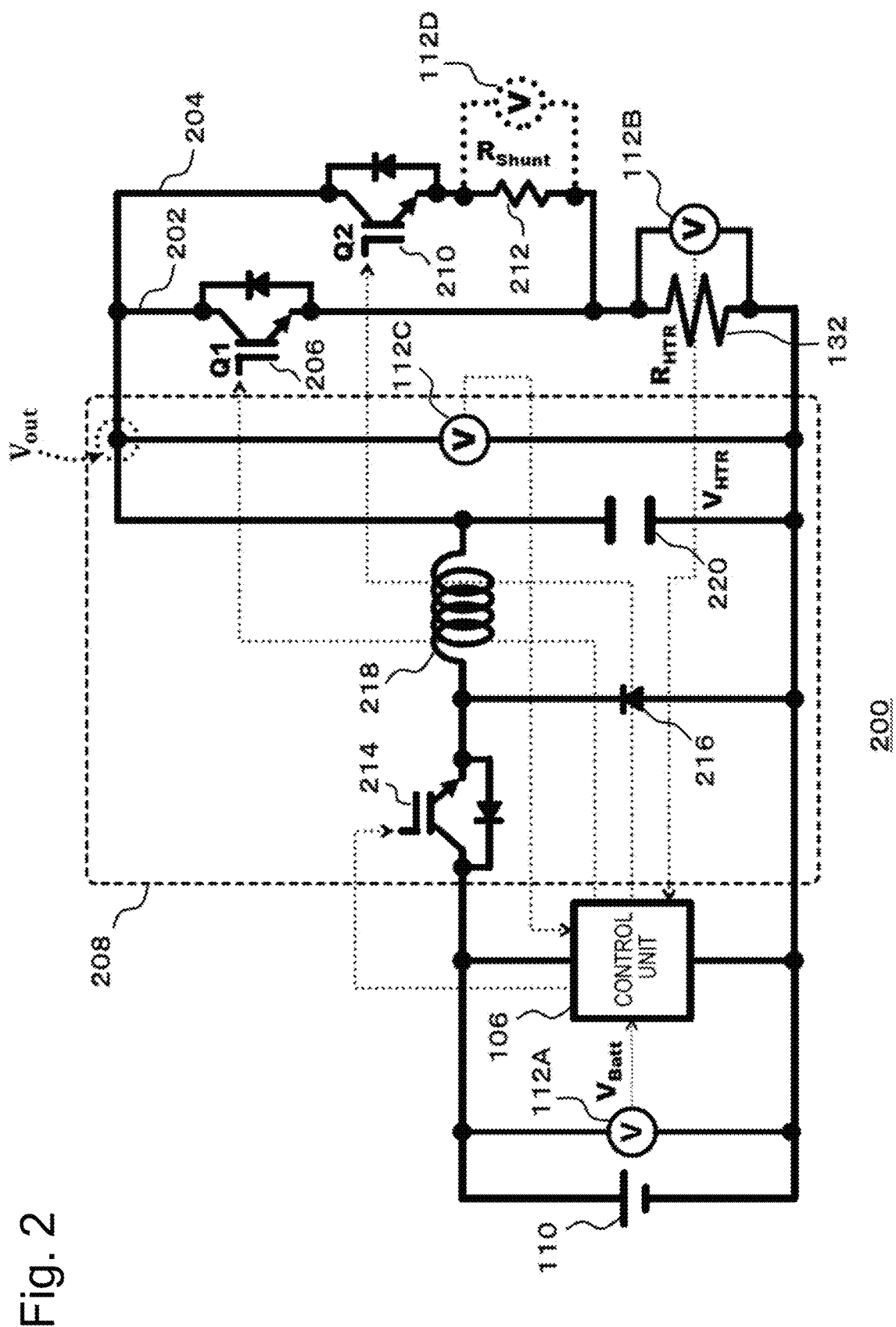
FIG. 2 is a diagram illustrating an exemplary circuit configuration of a portion of an aerosol generation device according to an embodiment of the present disclosure.

FIG. 2 is a diagram illustrating an exemplary circuit configuration of a portion of the aerosol generation device 100A according to a first embodiment of the present disclosure.

A circuit 200 illustrated in FIG. 2 includes the power source 110, the control unit 106, the sensors 112A to 112D (hereinafter also collectively referred to as the "sensor 112"), the load 132 (hereinafter also referred to as a "healer resistor"), a first circuit 202, a second circuit 204, a switch Q1 including a first field emission transistor (FET) 206, a conversion part 208, a switch Q2 including a second FET 210, and a resistor 212 (hereinafter, also referred to as a "shunt resistor"). Note that the sensor 112 may be embedded in the other component such as the control unit 106 or the conversion part 208. The electric resistance value of the load 132 changes in response to the temperature by using, for example, a positive temperature coefficient (PTC) heater or a negative temperature coefficient (NTC) heater. The shunt resistor 212 is connected in series with the load 132, and has a known electric resistance value. The electric resistance value of the shunt resistor 212 may be substantially invariant to the temperature. The shunt resistor 212 has an electric resistance value larger than that of the load 132. Depending on the embodiment, the sensors 112C and 112D may be omitted. It will be apparent to those skilled in the art that not only FET but also various elements such as an iGBT and a contactor can be used as the switches Q1 and Q2.

The conversion part 208 may be, for example, a switching converter, and may include a FET 214, a diode 216, an inductance 218, and a capacitor 220. The control unit 106 may control the conversion part 208 so that the conversion part 208 converts an output voltage of the power source 110 to apply the converted output voltage to the entire circuit. Instead of a step-down type switching converter illustrated in FIG. 2, a step-up type switching converter, a step-up/step-down type switching converter, a linear dropout (LDO) regulator, or the like may be used. Note that the conversion part 208 is not an essential component, and can be omitted. Furthermore, a control unit (not illustrated) provided separately from the control unit 106 may be configured to control the conversion part 208. This not-illustrated control unit may be embedded in the conversion part 208.

The circuit 134 illustrated in FIG. 1A may be electrically connected to the power source 110 and the load 132, and may include the first circuit 202 and the second circuit 204. The first circuit 202 and the second circuit 204 are connected in parallel to the power source 110 and the load 132. The first circuit 202 may include the switch Q1. The second circuit 204 may include the switch Q2 and the resistor 212 (and optionally the sensor 112D). The first circuit 202 may have a resistance value smaller than that of the second circuit 204. In this example, the sensors 112B and 112D are voltage sensors, and are configured to detect a voltage value across the load 132 and a voltage value across the resistor 212, respectively. However, a configuration of the sensor 112 is not limited thereto. For example, the sensor 112 may be a current sensor using a known resistor or a hall element, and may detect a value of a current flowing through the load 132 and/or the resistor 212.

As indicated by dotted-line arrows in FIG. 2, the control unit 106 can control the switch Q1, the switch Q2, and the like, and can acquire a value detected by the sensor 112. The control unit 106 may be configured to switch the switch Q1 from an off state to an on state to cause the first circuit 202 to function and configured to switch the switch Q2 from the off state to the on state to cause the second circuit 204 to function. The control unit 106 may be configured to alternately switch the switches Q1 and Q2 to alternately cause the first circuit 202 and the second circuit 204 to function.

The first circuit 202 is used to atomize the aerosol source. When the switch Q1 is switched to the on state to cause the first circuit 202 to function, the electric power is supplied to the heater (or the load 132 in the heater), and the load 132 is heated. The aerosol source retained in the retention unit 130 in the atomizing unit 118A (in the case of the aerosol generation device 100B of FIG. 1B, the aerosol source carried in the aerosol base material 116B) is atomized through heating by the load 132, whereby the aerosol is generated.

The second circuit 204 is used to acquire a value of a voltage applied to the load 132, a value related to a resistance value of the load 132, a value related to a temperature of the load 132, a value of a voltage applied to the resistor 212, and the like. As an example, it is assumed that the sensors 112B and 112D are voltage sensors as illustrated in FIG. 2. When the switch Q2 is on and the second circuit 204 is functioning, the current flows through the switch Q2, the resistor 212, and the load 132. A value of the voltage applied to the load 132 and/or a value of the voltage applied to the resistor 212 can be obtained by the sensors 112B and 112D, respectively. In addition, a value of a current flowing through the load 132 can be obtained using the value of the voltage applied to the resistor 212 that has been acquired by the sensor 112D and a known resistance value $R_{shunt}$ of the resistor 212. Since a total value of the resistance values of the resistor 212 and the load 132 can be obtained based on an output voltage $V_{out}$ of the conversion part 208 and the obtained current value, a resistance value $R_{HTR}$ of the load 132 can be obtained by subtracting the known resistance value $R_{shunt}$ from the total value. When the load 132 has a positive or negative temperature coefficient characteristic in which the resistance value changes in response to the temperature, the temperature of the load 132 can be estimated based on a relationship between the pre-known resistance value of the load 132 and the temperature of the load 132, and the resistance value $R_{HTR}$ of the load 132 that is obtained as described above. It will be appreciated by those skilled in the art that the resistance value and the temperature of the load 132 can be estimated using a value of the current flowing through the resistor 212 instead of the value of the current flowing through the load 132. The value related to the resistance value of the load 132 in this example may include a voltage value, a current value and the like of the load 132. A specific example of the sensors 112B and 112D is not limited to the voltage sensor, and may include the other elements such as a current sensor (for example, a hall element).

The sensor 112A detects an output voltage during discharging or in a no-load state of the power source 110. The sensor 112C detects an output voltage of the conversion part 208. Alternatively, the output voltage of the conversion part 208 may be a predetermined target voltage. These voltages are voltages applied to the entire circuit.

The resistance value $R_{HTR}$ of the load 132 when the temperature of the load 132 is "$T_{HTR}$" can be expressed as follows.

$$R_{HTR}(T_{HTR})=(V_{HRT} \times R_{shunt})/(V_{Batt}-V_{HTR})$$

Where $V_{Batt}$ is a voltage applied to the entire circuit. When the conversion part 208 is not used, "$V_{Batt}$" is an output voltage of the power source 110. When the conversion part 208 is used, "$V_{Batt}$" corresponds to the target voltage of the conversion part 208. "$V_{HTR}$" is a voltage applied to the heater. Instead of "$V_{HTR}$," the voltage applied to the shunt resistor 212 may be used.

Figure 3:
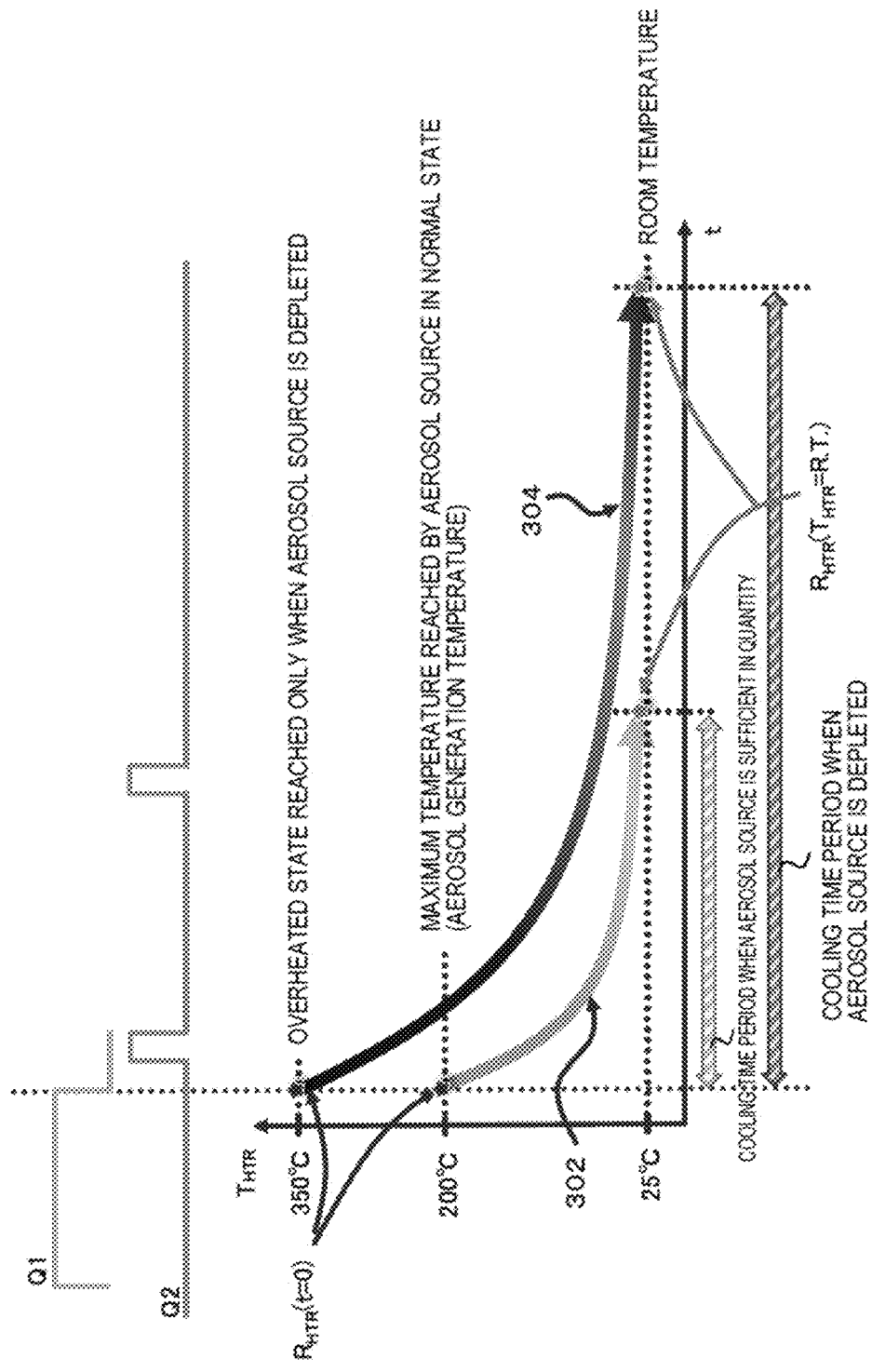
FIG. 3 schematically shows a cooling process of a load after the power supply to the load is stopped in each of states in which an aerosol source in a storage unit or an aerosol base material is sufficient in quantity and the aerosol source is depleted.

FIG. 3 schematically shows a cooling process of the load 132 after the switch Q1 is turned off and the power supply to the load 132 (heater) is stopped in each of a state in which the aerosol source in the storage unit 116A (or the aerosol base material 116B) is sufficient in quantity and a state in which the aerosol source is depleted. The horizontal axis represents time, and the vertical axis represents a temperature of the load 132.

A curve 302 represents a cooling curve of the load 132 when the aerosol source is sufficient in quantity. As long as the aerosol source is sufficient in quantity, the temperature of the load 132 is converged near a certain temperature (hereinafter, also referred to as a "maximum temperature reached by the aerosol source in a normal state" or a "aerosol generation temperature") even when the power supply from the power source 110 to the load 132 is continued. That is, the temperature of the load 132 when the power supply to the load 132 is stopped is the maximum temperature reached by the aerosol source in the normal state. This is a phenomenon resulting from a fact that thermal energy used for temperature increase of the load 132 and the aerosol source is used for evaporation (phase transition) of the aerosol source. When the aerosol source is formed from a single solvent, the maximum temperature reached by the aerosol source in the normal state coincides with a boiling point of the solvent. On the other hand, when the aerosol source is formed from a mixed solvent, the maximum temperature reached by the aerosol source in the normal state changes in response to composition of various solvents included in the mixed solvent and the molar ratio thereof. The maximum temperature reached by the aerosol source in the normal state in the mixed solvent may be obtained by an experiment, or may be analytically obtained using the Raoult's law, or the like. As an example, as shown in FIG. 3, the temperature of the load 132 when the switch Q1 is turned off and the power supply to the load 132 is stopped is about 200° C. The temperature of the load 132 decreases with an elapse of time, and reaches a room temperature (here, 25° C.), as indicated by the curve 302.

A curve 304 represents a cooling curve of the load 132 when the aerosol source is depleted (or is insufficient in quantity). Since the aerosol source is depleted, the temperature of the load 132 is higher than the aerosol generation temperature when the power supply to the load 132 is stopped. Therefore, the load 132 is in an overheated state. As an example, as shown in FIG. 3, the temperature of the load 132 may reach 350° C. When the power supply is stopped, the temperature of the load 132 decreases with an elapse of time, and then reaches the room temperature, as indicated by the curve 304.

"$R_{HTR}(t=0)$" represents an electric resistance value of the load 132 when the power supply to the load 132 is stopped. "$R_{HTR}(T_{HTR}=R.T.)$" represents an electric resistance value of the load 132 when the temperature of the load 132 reaches the room temperature.

As shown in FIG. 3, a time period required for the temperature of the load 132 to decrease to the room temperature when the aerosol source is depleted is longer than the time period required for the temperature of the load 132 to decrease to the room temperature when the aerosol source is sufficient in quantity. This is because although the load 132 is cooled mainly by an air-cooling effect, the temperature of the load 132 when the switch Q1 is turned off and the power supply to the load 132 is stopped is higher when the aerosol source is depleted than when the aerosol source is sufficient in quantity, Note that since, when the aerosol source is sufficient in quantity, the load 132 can be cooled by the aerosol source having a temperature lower than that of the load 132 and the aerosol source newly supplied from the storage unit 116A, a difference in the time period required for the temperature of the load 132 to decrease to the room temperature easily occurs between when the aerosol source is depleted and when the aerosol source is sufficient in quantity.

Figure 4:
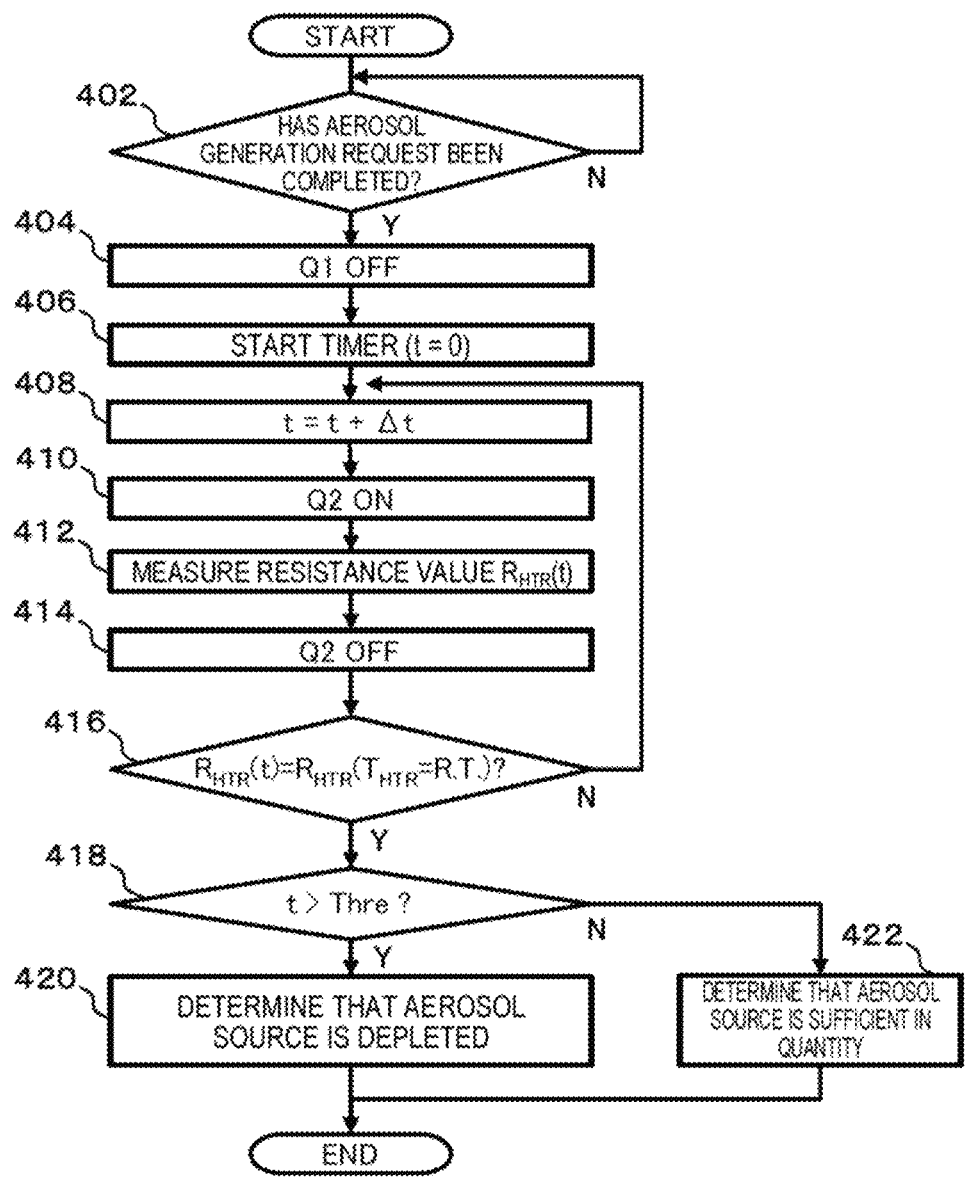
FIG. 4 is a flowchart of processing for monitoring a cooling process of the load and determining whether the aerosol source is depleted, according to an embodiment of the present disclosure.

FIG. 4 is a flowchart of processing for monitoring a cooling process of the load 132 and determining whether the aerosol source is depleted, according to an embodiment of the present disclosure. Here, all the steps will be described as being performed by the control unit 106. However, it should be noted that some of the steps may be performed by another component in the aerosol generation device 100.

An aerosol generation request by the user is continued up to a point prior to the processing of FIG. 4. The process starts at step 402, and the control unit 106 determines whether the aerosol generation request has been completed. As an example, the control unit 106 may determine whether user's inhalation has been completed, based on output of the pressure sensor, and the like. In another example, the control unit 106 may determine whether the aerosol generation request has been completed, based on whether a button provided in the aerosol generation device 100 to supply the electric power to the load 132 is no longer pressed. In still another example, the control unit 106 may determine whether the aerosol generation request has been completed, based on whether a predetermined time period has elapsed since detection of an operation on a user interface such as pressing the button provided in the aerosol generation device 100 to supply the electric power to the load 132.

When the aerosol generation request is continued ("N" in step 402), the process returns to before step 402. When the aerosol generation request is completed ("Y" in step 402), the process proceeds to step 404. In step 404, the control unit 106 turns off the switch Q1, and stops the power supply to the load 132.

The process proceeds to step 406, and the control unit 106 starts a timer. The control unit 106 may set a value of the timer to an initial value t=0.

The process proceeds to step 408, and the control unit 106 waits until the time is advanced by a predetermined value $\Delta t$. As another example, when the process proceeds from step 416 (described later) back to step 408, the control unit 106 may add (increment), to "t", the time period $\Delta t$ elapsed since the latest time when step 416 is performed.

The process proceeds to step 410, and the control unit 106 turns on the switch Q2 to cause the second circuit 204 to function. The control unit 106 can measure an electric resistance value $R_{HTR}(t)$ of the load 132 in a method described in connection with FIG. 2. In step 412, the control unit 106 may acquire the electric resistance value from the sensor that detects the electric resistance value of the load 132. Alternatively, the control unit 106 may obtain the electric resistance value using a value acquired from the sensor that detects an electric value (a current value or the like) related to the electric resistance. Next, in step 414, the control unit 106 turns off the switch Q2.

The process proceeds to step 416, and the control unit 106 determines whether the value $R_{HTR}(t)$ obtained in step 412 is equal to a predetermined value $R_{HTR}(T_{HTR}=R.T.)$. As shown in FIG. 3, when the load 132 is a PTC heater, the resistance value of the load 132 decreases with an elapse of time from the value $R_{HTR}(t=0)$ corresponding to the temperature at a time point when the switch Q1 is turned off. When the temperature of the load 132 reaches the room temperature, the resistance value of the load 132 becomes $R_{HTR}(T_{HTR}=R.T.)$. Accordingly, the above-described determination as to the resistance value of the load 132 that is made in step 416 enables determination as to whether the temperature of the load 132 has decreased to the room temperature.

When the resistance value of the load 132 does not reach the predetermined value ("N" in step 416), the process returns to before step 408. When the resistance value of the load 132 reaches the predetermined value ("Y" in step 416), the process proceeds to step 418. In step 418, the control unit 106 determines whether a value t of the timer (i.e., a time period elapsed since turning off of the switch Q1) at this time exceeds a predetermined threshold Thre. As shown in FIG. 3, "Thre" represents a cooling time period required until the temperature of the load 132 decreases to the room temperature when the aerosol source is sufficient in quantity.

When the value of the timer exceeds the threshold ("Y" in step 418), the process proceeds to step 420. This means that the time period until the temperature of the load 132 decreases to the room temperature requires a time period exceeding the threshold Thre, and therefore, as can be understood from the description of FIG. 3, it is appreciated that the load 132 is in the overheated state at a time point when the switch Q1 is turned off. Accordingly, in step 420, the control unit 106 determines that the aerosol source is depleted.

When the value of the timer is equal to or smaller than the threshold ("N" in step 418), the process proceeds to step 422. In step 422, the control unit 106 determines that the aerosol source is sufficient in quantity.

According to the embodiment of FIG. 4, the control unit 106 can monitor the cooling process of the load after the temperature of the load increases up to a temperature in which the aerosol source can be atomized or higher, based on a time-series change in the value detected by the sensor 112. This monitoring is performed in a manner that retains the correlation between the time-series change in the value detected by the sensor 112 and the decrease in the temperature of the load. For example, when the load 132 is a PTC heater, the time-series change in the electric resistance value of the load 132 is correlated with the temperature of the load 132. Therefore, when the temperature of the load 132 decreases with an elapse of time, the electric resistance value of the load 132 also decreases. According to such a configuration, the cooling process of the load (heater) can be observed with high accuracy even without using a dedicated temperature sensor.

In addition, according to the embodiment of FIG. 4, the control unit 106 is configured to determine, based on the cooling process, whether the depletion of the aerosol source has occurred in the storage unit 116A or the aerosol base material 116B. Accordingly, the depletion of the aerosol source can be detected in a state in which disturbance such as a user's inhalation is low.

Figure 5:
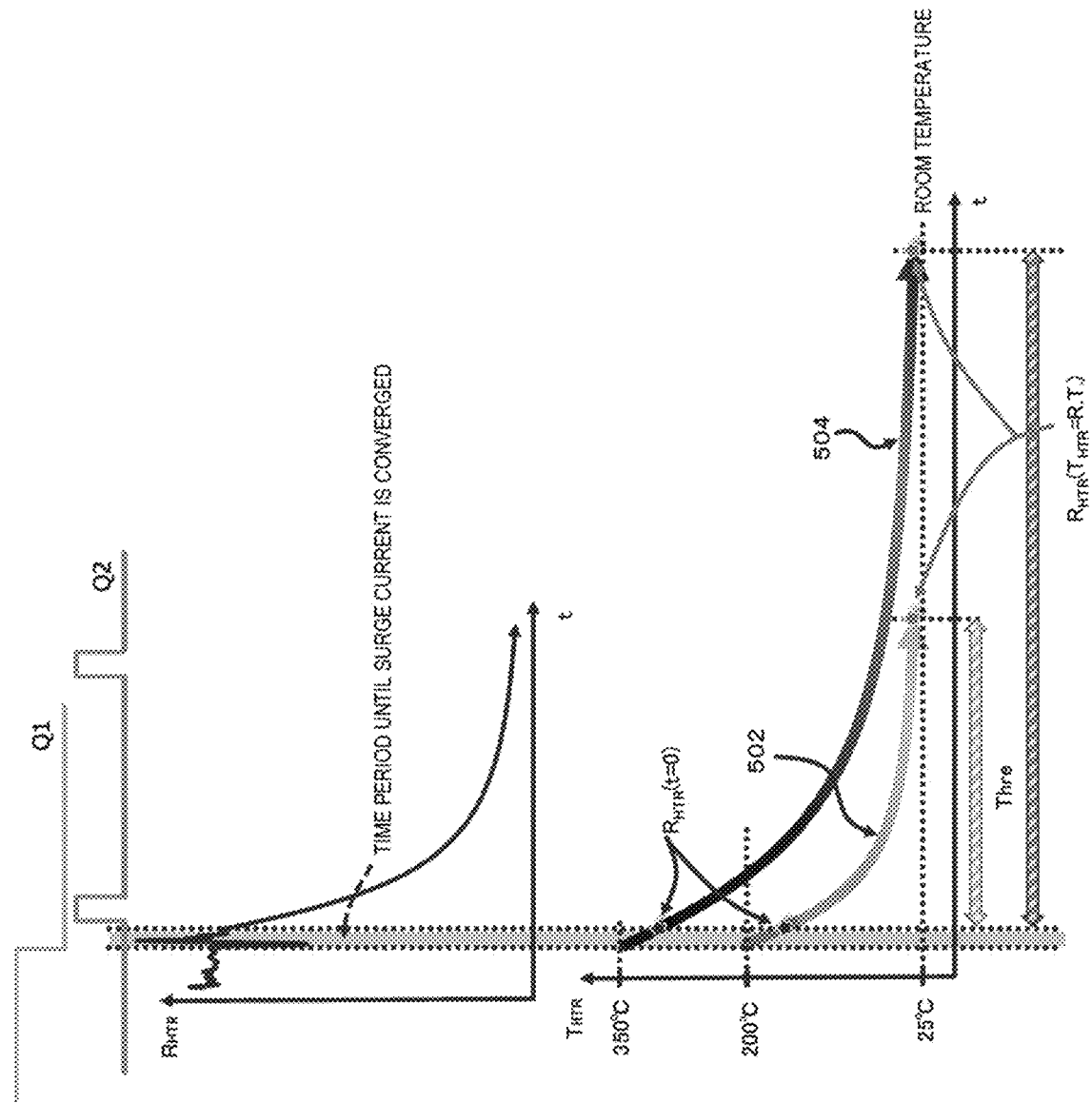
FIG. 5 shows that the measured resistance value of the load may change largely due to generation of a surge current.

FIG. 5 shows that the measured resistance value of the load 132 may fluctuate largely due to generation of a surge current (or a residual current). A curve 502 represents a cooling curve of the load 132 when the aerosol source is sufficient in quantity. A curve 504 represents a cooling curve of the load 132 when the aerosol source is depleted (or is insufficient in quantity). Reference numeral 506 denotes a time period required for the surge current (or the residual current) to be converged. Since the circuit 134 includes at least an inductor (inductive) component, the current flowing through the first circuit 202 changes suddenly immediately after the switch Q1 is turned off, resulting in generation of the surge current having a magnitude corresponding to a product of a degree of the sudden change of the current (time differential value) and inductance. Accordingly, when the switch Q2 is turned on immediately after the switch Q1 is turned off, and the resistance value of the load 132 is measured, the surge current is superimposed on a current for measuring the resistance value. This causes inconvenience that the measured resistance value of the load 132 fluctuates largely, or the like. In other words, the change in the electric resistance value of the load 132 and the temperature of the load 132 may diverge from each other without being able to have the above-described correlation therebetween. Accordingly, it becomes difficult to observe the cooling process of the load 132 with high accuracy and accurately measure the time period until the temperature of the load 132 reaches the room temperature. Note that since the circuit 134 includes at least a capacitor (capacitive) component in addition to the inductor component, the residual current flowing through the circuit after the switch Q1 is turned off may cause inconvenience in a similar manner to the surge current.

Figure 6:
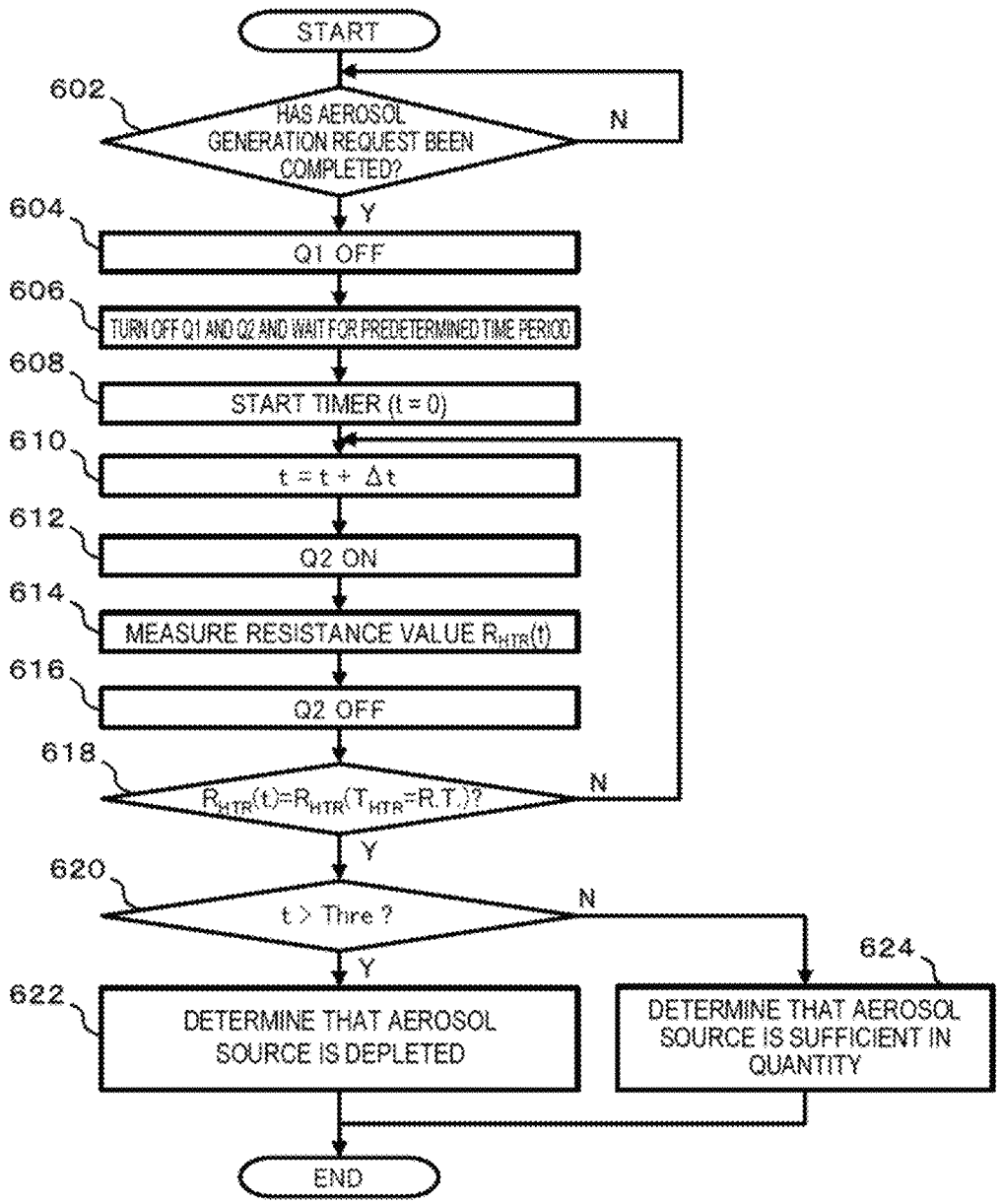
FIG. 6 is a flowchart illustrating processing according to an embodiment of the present disclosure.

FIG. 6 is a flowchart illustrating processing according to an embodiment of the present disclosure, capable of solving the above-described problem. The processes in steps 602 and 604 are the same as the processes in steps 402 and 404 in FIG. 4, and therefore, the description thereof is omitted.

In step 606, the control unit 106 waits for a predetermined time period (e.g., 10 ms) in a state in which both of the switch Q1 and the switch Q2 are off. That is, a dead zone in which the cooling process is not monitored or the determination, based on the monitored cooling process, as to whether the depletion has occurred is not made is provided when or immediately after the cooling process of the load 132 starts. At this time, the predetermined time period may be, for example, a time period 506 until the surge current is converged, as shown in FIG. 5. As described above, the surge current has the magnitude corresponding to the degree of supply of the current (time differential value), and therefore, the surge current decreases gradually with an elapse of time. Similarly, the residual current also decreases gradually with an elapse of time. The information on the time may be prestored in the memory 114 or may be variably set according to an output value of the sensor 112. When the dead zone is provided, the timing when the switch Q2 is turned on is delayed by the above-described predetermined time period, as shown in FIG. 5. The processes in steps 608 to 624 are the same as the processes in steps 406 to 422 in FIG. 4, and therefore, the description thereof is omitted. Note that the process in step 608 may be performed before step 606.

According to the embodiment of FIG. 6, the control unit 106 is configured to provide a dead zone in which the cooling process is not monitored or the determination, based on the monitored cooling process, as to whether the depletion of the aerosol source has occurred is not made, when or immediately after the cooling process starts. Accordingly, since it is less likely to observe fluctuation in the output value of the sensor 112 that may occur when the resistance value of the load 132 is measured when or immediately after the cooling process starts, the observation accuracy of the cooling process of the load is improved.

The dead zone may be provided until a current value of at least one of the residual current and the surge current that are generated at the end of the power supply becomes equal to or smaller than the threshold. As an example, the control unit 106 may be configured to cause a magnetic sensor included in the sensor 112 to observe electromagnetic noise generated by the residual current and the surge current, and determine the current value of at least one of the residual current and the surge current based on magnitude of the observed noise. This can prevent the cooling process from being observed in a state in which the residual current and the surge current are superimposed on the output value of the sensor 112, whereby the observation accuracy is improved.

The time period of the dead zone may be shorter than the time period until the cooling process is completed in the state in which the depletion of the aerosol source does not occur. As an example, the time period of the dead zone may be shorter than "Thre" shown in FIG. 5. This can prevent the dead zone from being set to be excessively long, thereby allowing unimpeded observation of the cooling process.

Figure 7:
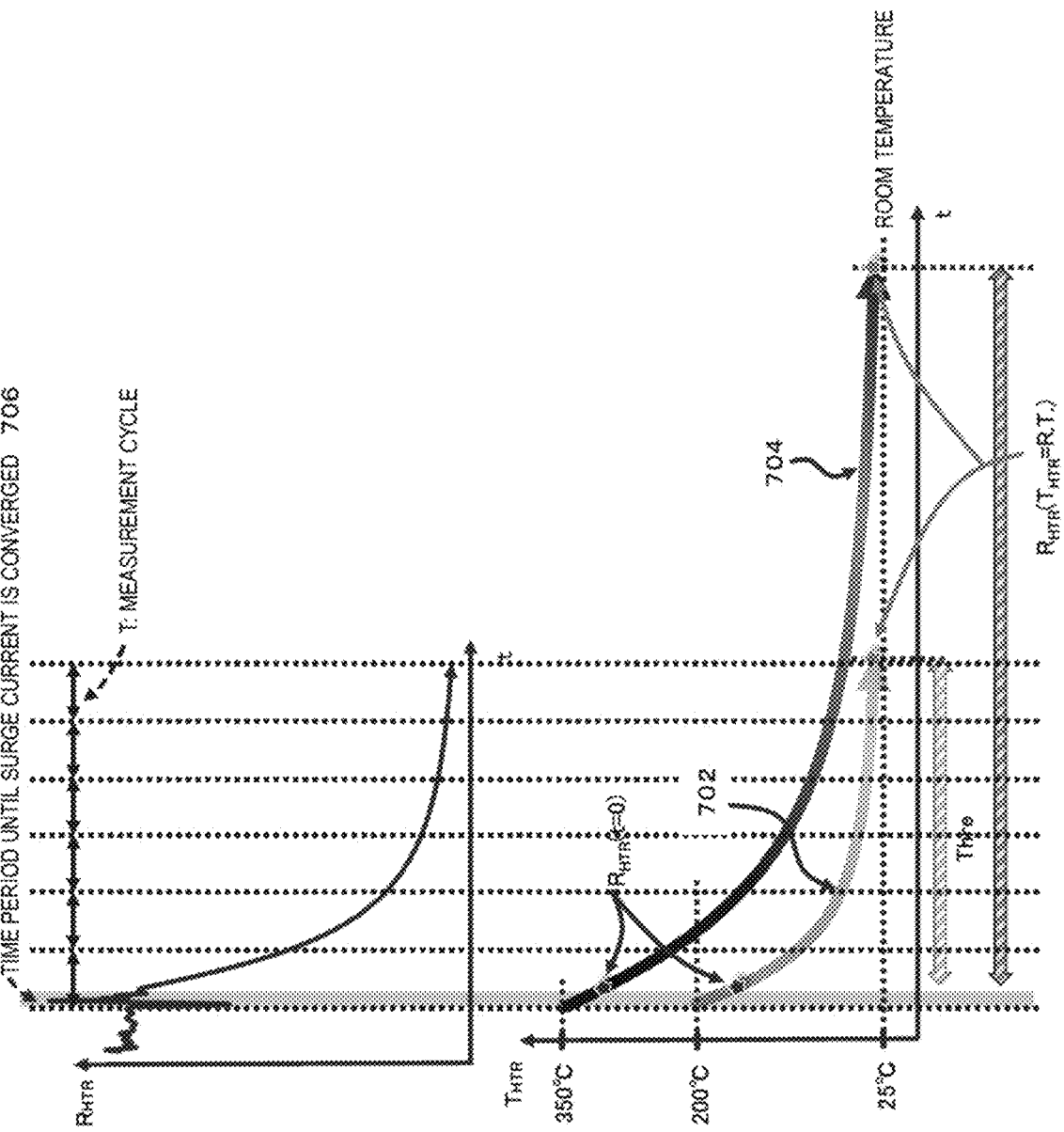
FIG. 7 conceptually shows an embodiment of the present disclosure for reducing an influence of generation of a surge current.

FIG. 7 conceptually shows an embodiment of the present disclosure for reducing an influence of generation of a surge current (or a residual current). A curve 702 represents a cooling curve of the load 132 when the aerosol source is sufficient in quantity. A curve 704 represents a cooling curve of the load 132 when the aerosol source is depleted (or is insufficient in quantity). Reference numeral 706 denotes a time period until the surge current (or residual current) is converged. In this example, a value related to an electric resistance value of the load 132 is detected by the sensor 112 during monitoring of the cooling process, in a cycle T longer than a time period (the time period denoted by reference numeral 706) required until the current value of at least one of the residual current and the surge current that are generated at the end of the power supply to the load 132 becomes equal to or smaller than the threshold. Note that the above-described detection may or may not be performed at a time point indicated by the left-most dotted line (a time point when the surge current is generated).

Figure 8:
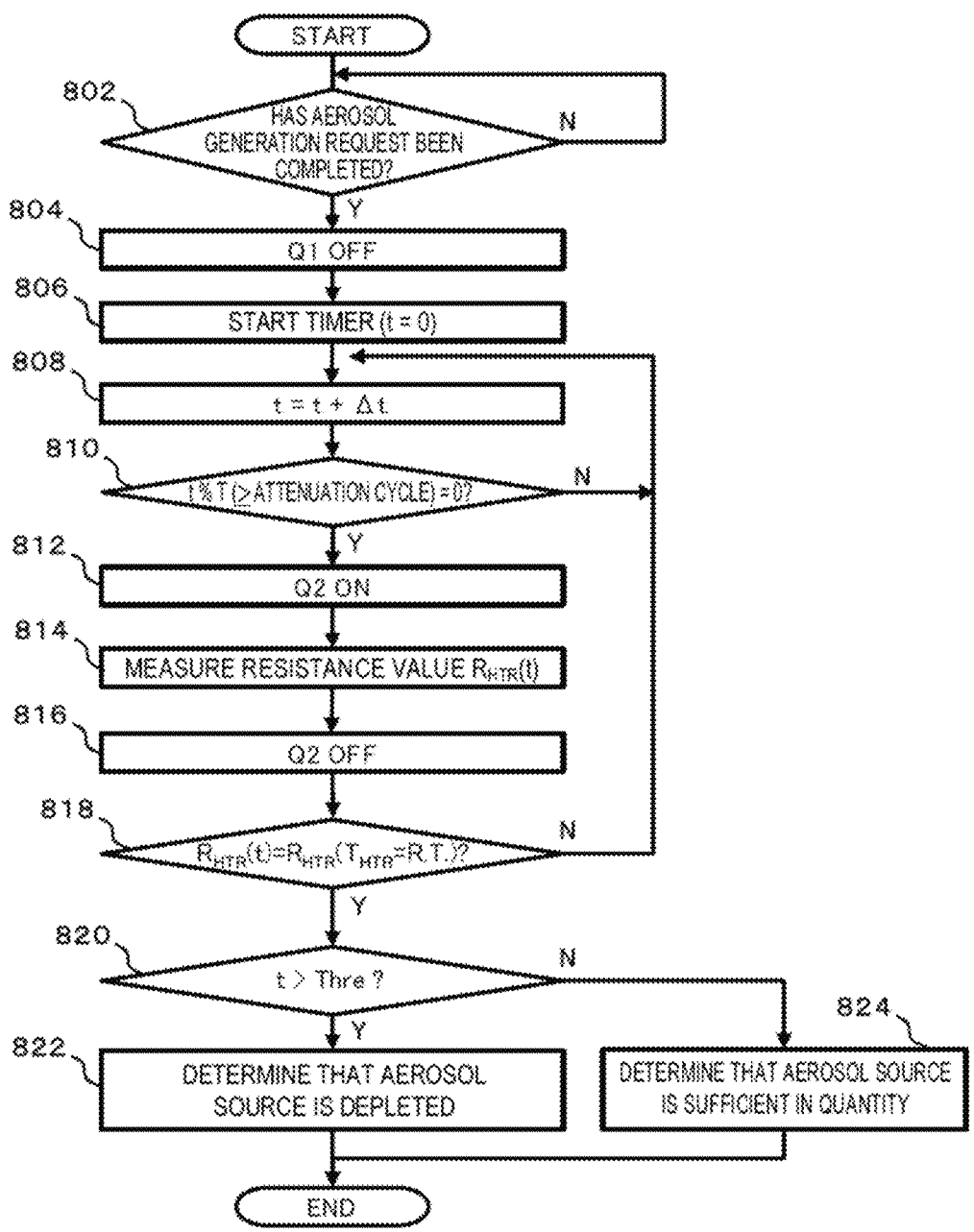
FIG. 8 is a flowchart of processing according to an embodiment of the present disclosure in connection with FIG. 7.

FIG. 8 is a flowchart of processing according to an embodiment of the present disclosure in connection with FIG. 7. The processes in steps 802 to 808 are the same as the processes in steps 402 to 408 in FIG. 4.

In step 810, the control unit 106 determines whether a time t indicated by the timer is an integer multiple of the above-described cycle T. When "t" is not an integer multiple of "T" ("N" in step 810), the process returns to before step 808.

When "t" is an integer multiple of "T" ("Y" in step 810), "t" is regarded as having reached timing of measurement indicated by the dotted line in FIG. 7. The process proceeds to step 812, the switch Q2 is turned on, and an electric resistance value of the load 132 or a value related to the electric resistance is measured. The processes in steps 812 to 824 are the same as the processes in steps 410 to 422 in FIG. 4.

According to the embodiment of FIG. 7 and FIG. 8, the control unit 106 is configured to detect the value related to the electric resistance value by the sensor 112 during monitoring of the cooling process, in a cycle longer than the time period required until the current value of at least one of the residual current and the surge current that are generated at the end of the power supply becomes equal to or smaller than the threshold. Accordingly, since it is less likely to observe fluctuation in the output value of the sensor 112 that may occur when the resistance value of the load 132 is measured when or immediately after the cooling of the load 132 starts, the observation accuracy of the cooling process is improved.

Figure 9:
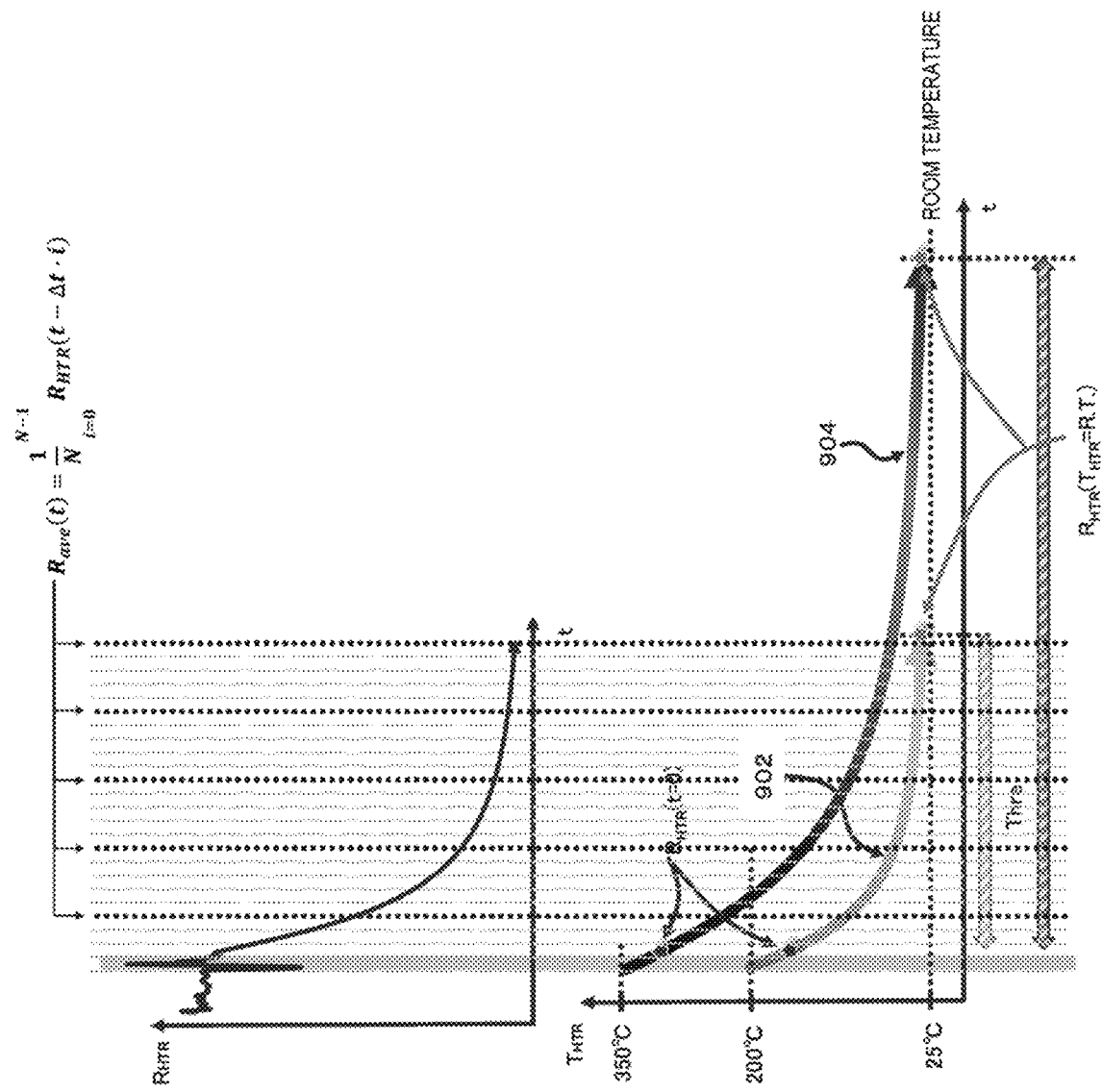
FIG. 9 conceptually shows an embodiment of the present disclosure for reducing an influence of generation of a surge current.

FIG. 9 conceptually shows an embodiment of the present disclosure for reducing an influence of generation of a surge current. A curve 902 represents a cooling curve of the load 132 when the aerosol source is sufficient in quantity. A curve 904 represents a cooling curve of the load 132 when the aerosol source is depleted (or is insufficient in quantity). In this example, a value detected by the sensor 112 when or immediately after the cooling process starts is corrected by smoothing a time-series change in the value. In an example, as represented by an expression in FIG. 9, an average value of the resistance values of the load 132 that are measured at measurement time points from a certain time point to another certain time point may be determined as a resistance value of the load 132 at the measurement time point. For example, assuming that N=5 in the expression represented in FIG. 9, the resistance value at a time point corresponding to the last dotted line among the five dotted lines shown in FIG. 9 may be obtained as an average value of the five resistance values measured at the five time points including the above-described time point and the previous four time points. Note that the average value of the resistance values of the load 132 that are measured at the measurement time points from a certain time point (a start point) to another certain time point (an end point) may be obtained not as the resistance value at the end point but as the resistance value at the start point, or may be obtained as the resistance value at the time point included between the start point and the end point.

Figure 10:
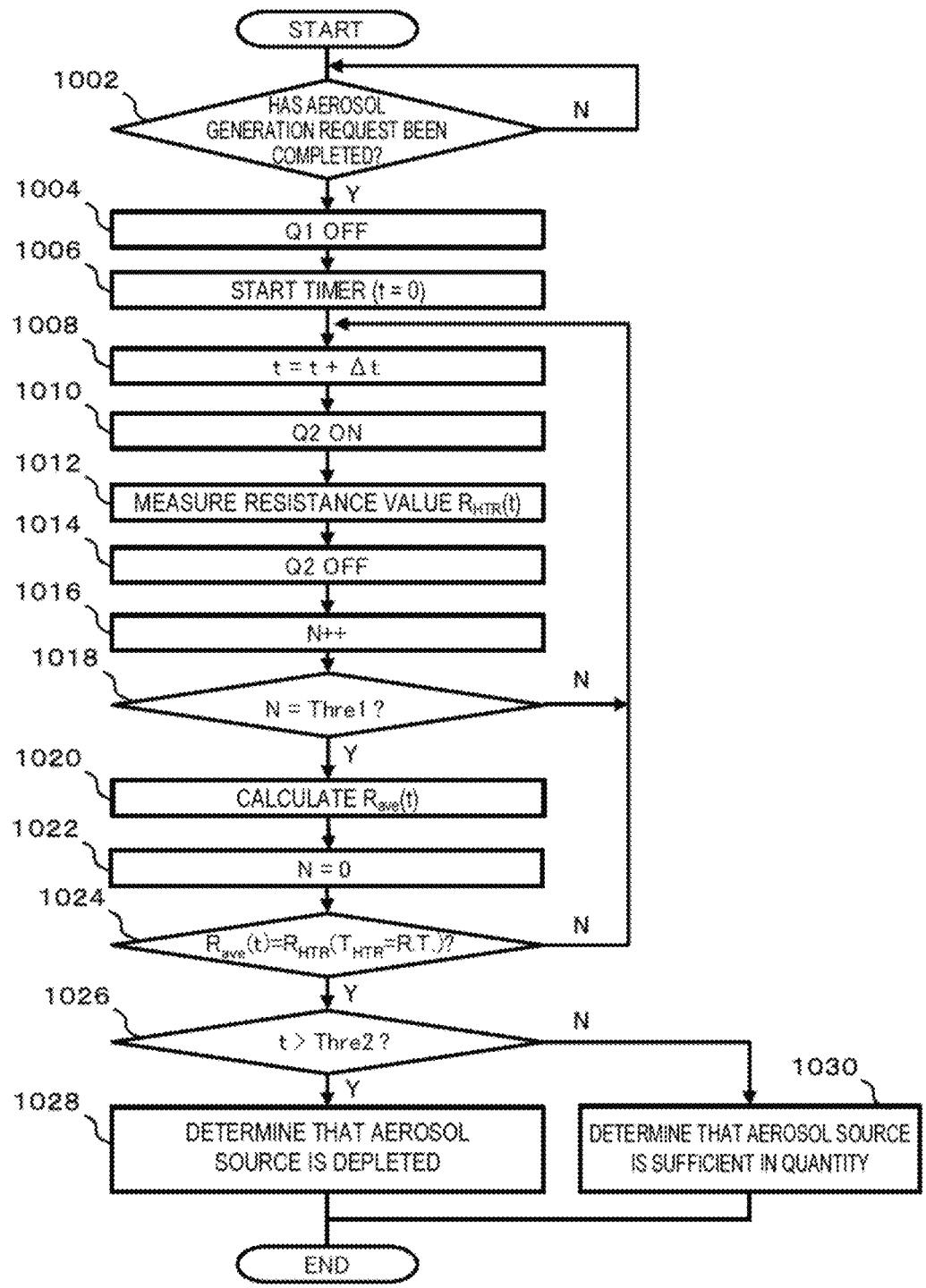
FIG. 10 is a flowchart of processing according to an embodiment of the present disclosure in connection with FIG. 9.

FIG. 10 is a flowchart of processing according to an embodiment of the present disclosure in connection with FIG. 9. The processes in steps 1002 to 1014 are the same as the processes in steps 402 to 414 in FIG. 4.

In step 1016, the control unit 106 increases (increments) a predetermined integer N. An initial value of "N" may be zero, and in step 1016, the value of "N" may be increased by 1. The "N" corresponds to "N" appearing on the right side of the expression indicated in FIG. 9.

The process proceeds to step 1018, and the control unit 106 determines whether "N" is equal to a predetermined threshold Thre1. In an example, when the average value of the five measured resistance values is used as a resistance value used for control, "N" is 5.

When "N" does not reach the threshold ("N" in step 1018), the process returns to before step 1008. When "N" reaches the threshold ("Y" in step 1018), the process proceeds to step 1020. In step 1020, the control unit 106 calculates "$R_{ave}(t)$" based on the expression indicated in FIG. 9, for example. The process proceeds to step 1022, and the control unit 106 resets "N" to zero. The subsequent processes in steps 1024 to 1030 are the same as the processes in steps 416 to 422 in FIG. 4.

According to the embodiment of FIG. 9 and FIG. 10, the control unit 106 is configured to correct the value detected by the sensor 112 when or immediately after the cooling process starts by smoothing the time-series change in the value detected by the sensor 112, and monitor the cooling process based on the corrected value. In the example of FIG. 9 and FIG. 10, a plurality of obtained values are simply averaged, but in another example, moving average of a plurality of measurement values may be obtained. According to these configurations, the depletion of the aerosol source can be detected in a state in which an influence of disturbance such as a user's inhalation is low. In addition, the control unit 106 may be configured to correct the value detected by the sensor 112 using at least one of an average process and a low-pass filter. This makes it possible to achieve the smoothing process in a simpler method.

Proper measurement timing of the values for monitoring the cooling process of the load will be described with reference to FIG. 11 to FIG. 15. According to a method of measuring an electric resistance value of the load 132 as described in connection with FIG. 2, the cooling process of the load 132 can be monitored without using a dedicated temperature sensor. However, since it is necessary to energize the circuit 134 to measure the electric resistance value of the load 132, the load 132 at least generates heat by a current flowing through the load 132 every time the electric resistance value of the load 132 is measured. Accordingly, monitoring the cooling process of the load at improper measurement timing causes disturbance, resulting that the observation accuracy of the cooling process of the load may be reduced.

Figure 11:
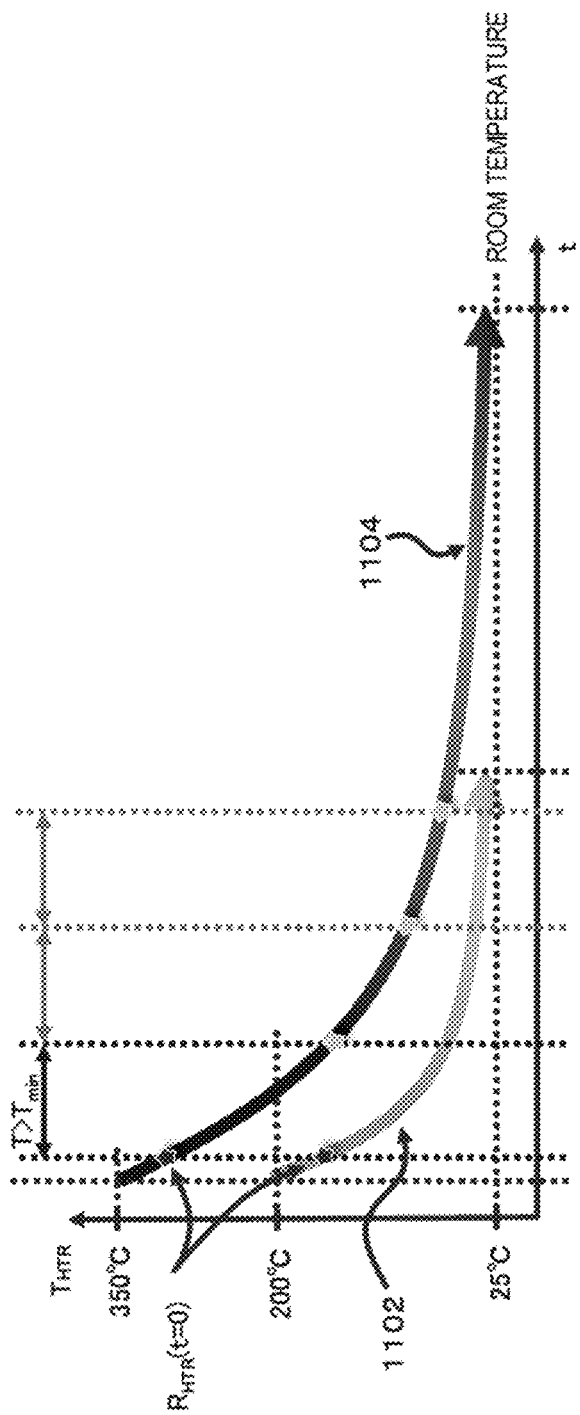
FIG. 11 conceptually shows measurement timing of values for monitoring the cooling process of the load, according to an embodiment of the present disclosure.

FIG. 11 conceptually shows measurement timing of values for monitoring the cooling process of the load, according to an embodiment of the present disclosure. A curve 1102 represents a cooling curve of the load 132 when the aerosol source is sufficient in quantity. A curve 1104 represents a cooling curve of the load 132 when the aerosol source is depleted (or is insufficient in quantity). Similarly to the embodiment of FIG. 4, the cooling process can be monitored in a manner that retains the correlation between the time-series change in the value detected by the sensor 112 and the decrease in the temperature of the load 132. For example, when the load 132 is a PTC heater, the time-series change in the electric resistance value of the load 132 is correlated with the temperature of the load 132. Therefore, when the temperature of the load 132 decreases with an elapse of time, the electric resistance value of the load 132 also decreases. At this time, in an example, as shown in FIG. 11, a cycle T in which the sensor 112 detects a value of an electric resistance or an electric value related to the electric resistance during monitoring of the cooling process may be larger than a minimum value $T_{min}$ achievable by the control unit 106. The monitoring of the cooling process may be started after an elapse of a predetermined time period since the end of power supply, and the predetermined time period may be larger than the minimum value $T_{min}$ achievable by the control unit 106. According to such a configuration, the measurement timing of the values for monitoring the cooling process of the load becomes proper, whereby the cooling process of the load can be observed with high accuracy even without using the dedicated temperature sensor.

Figure 12:
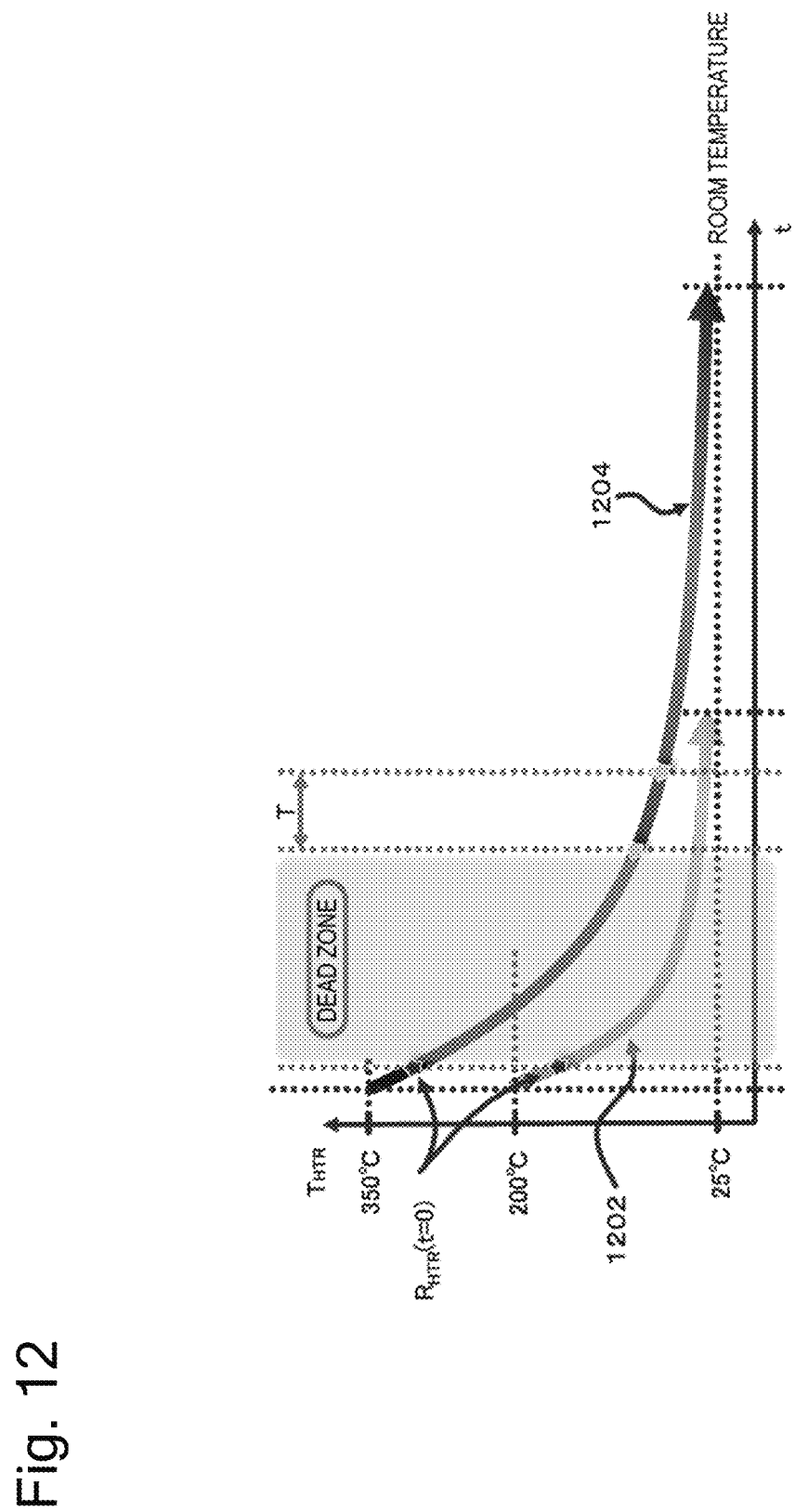
FIG. 12 conceptually shows measurement timing of values for monitoring the cooling process of the load, according to an embodiment of the present disclosure.

FIG. 12 conceptually shows measurement timing of values for monitoring the cooling process of the load, according to an embodiment of the present disclosure. A curve 1202 represents a cooling curve of the load 132 when the aerosol source is sufficient in quantity. A curve 1204 represents a cooling curve of the load 132 when the aerosol source is depleted (or is insufficient in quantity). As shown in the figure, a dead zone for a predetermined time period may be provided after a value of an electric resistance of the load 132 or an electric value related to the electric resistance is measured at a time t=0, and the value may be measured again after the end of the dead zone. The value need not be measured during the dead zone. Alternatively, although the value is measured also during the dead zone, the value measured during the dead zone need not be used for determination as to whether the aerosol source has been depleted. The cycle T in which the value is measured after the end of the dead zone may be larger than the minimum value $T_{min}$ achievable by the control unit 106, or may be $T_{min}$. Furthermore, the monitoring of the cooling process may be started after an elapse of a predetermined time since the end of power supply.

Figure 13:
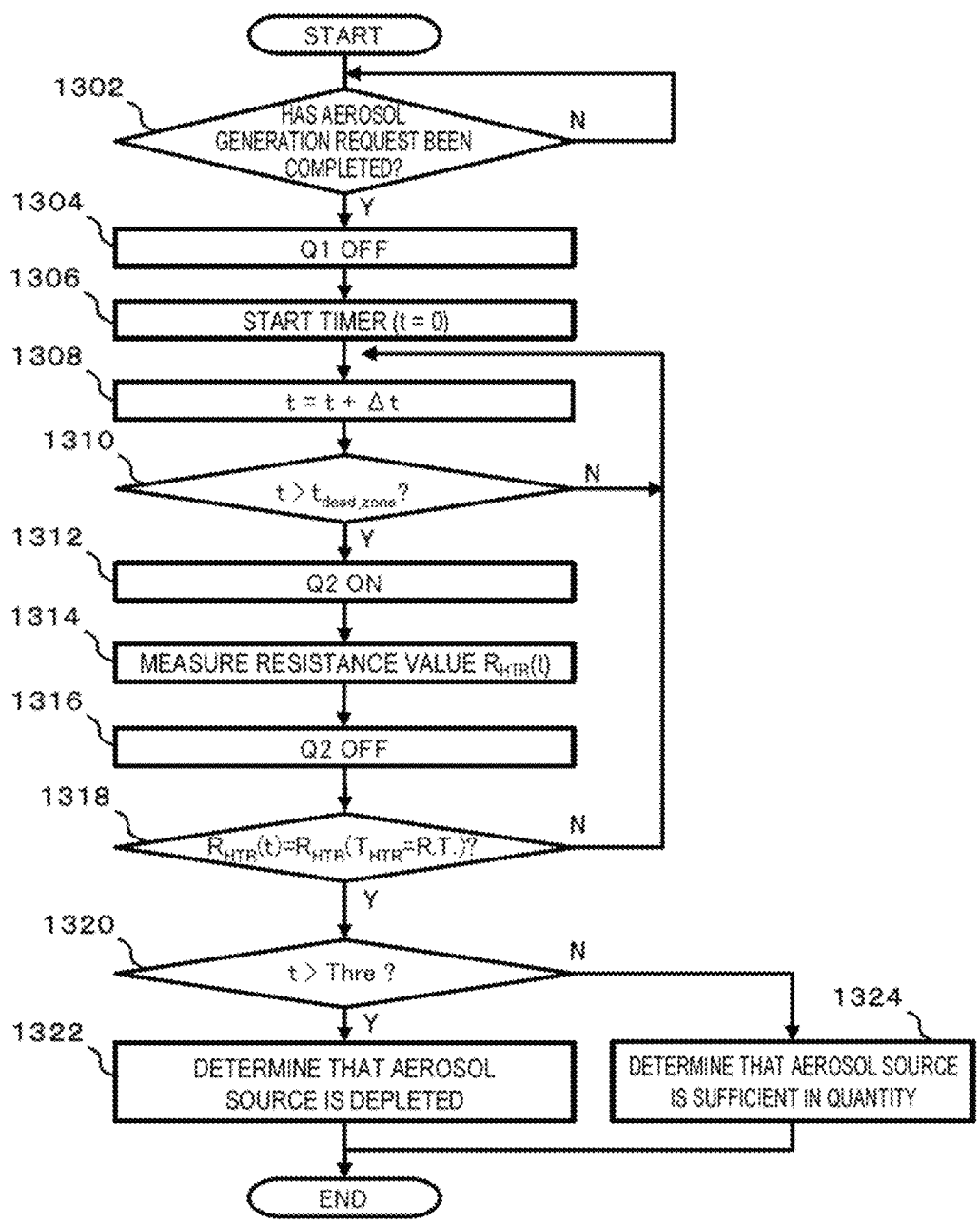
FIG. 13 is a flowchart of processing according to an embodiment of the present disclosure in connection with FIG. 12.

FIG. 13 is a flowchart of processing according to an embodiment of the present disclosure in connection with FIG. 12. The processes in steps 1302 to 1308 are the same as the processes in steps 402 to 408 in FIG. 4.

In step 1310, the control unit 106 determines whether a time indicated by the timer exceeds a predetermined time period $t_{dead\_zone}$ of the dead zone (i.e., whether the dead zone has been completed). When the dead zone has not been completed ("N" in step 1310), the process returns to before step 1308. When the dead zone has been completed ("Y" in step 1310), the process proceeds to step 1312. The processes in steps 1312 to 1324 are the same as the processes in steps 410 to 422 in FIG. 4. According to the embodiment of FIG. 12 and FIG. 13, when the dead zone is provided, the measurement timing of the values for monitoring the cooling process of the load becomes proper, whereby the cooling process of the load can be observed with high accuracy even without using the dedicated temperature sensor.

Figure 14:
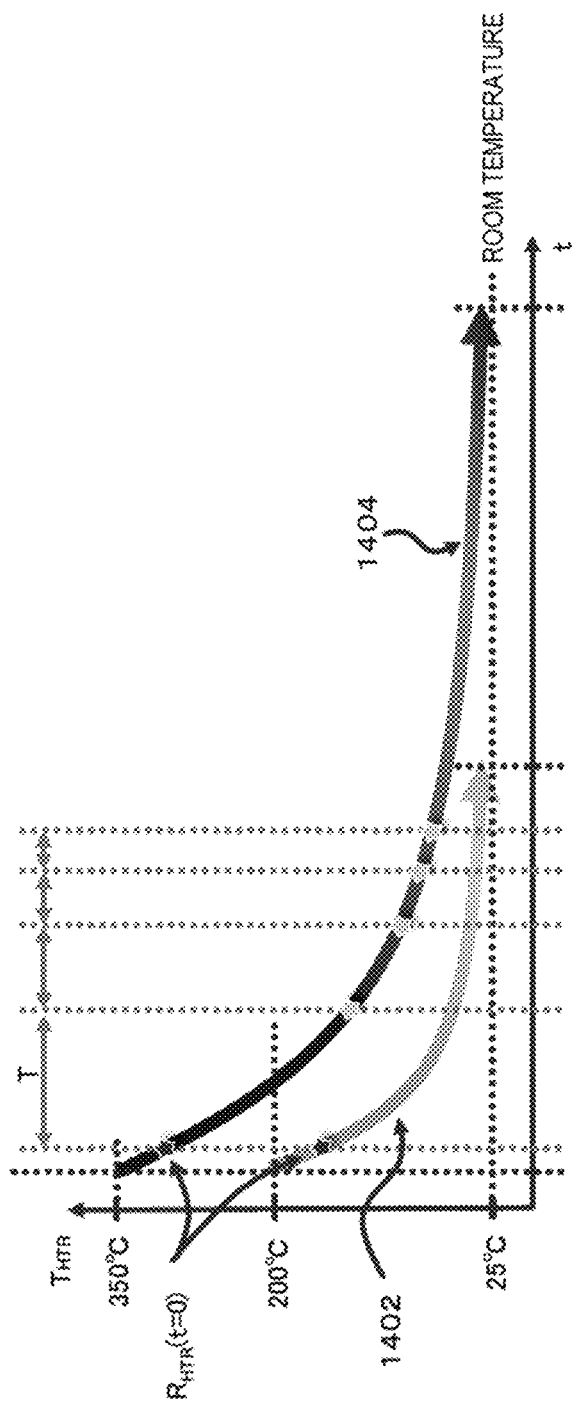
FIG. 14 conceptually shows measurement timing of values for monitoring the cooling process of the load, according to an embodiment of the present disclosure.

FIG. 14 conceptually shows measurement timing of values for monitoring the cooling process of the load, according to an embodiment of the present disclosure. A curve 1402 represents a cooling curve of the load 132 when the aerosol source is sufficient in quantity. A curve 1404 represents a cooling curve of the load 132 when the aerosol source is depleted (or is insufficient in quantity). As shown in the figure, the time period from when a value of an electric resistance of the load 132 or an electric value related to the electric resistance is measured for the first time at a time t=0 until the value is measured for the second time may be longer than the time period between the second measurement time point and the third measurement time point. As shown in the figure, after that, the time period between the adjacent measurement time points may be set to become gradually shorter as time goes on.

Figure 15:
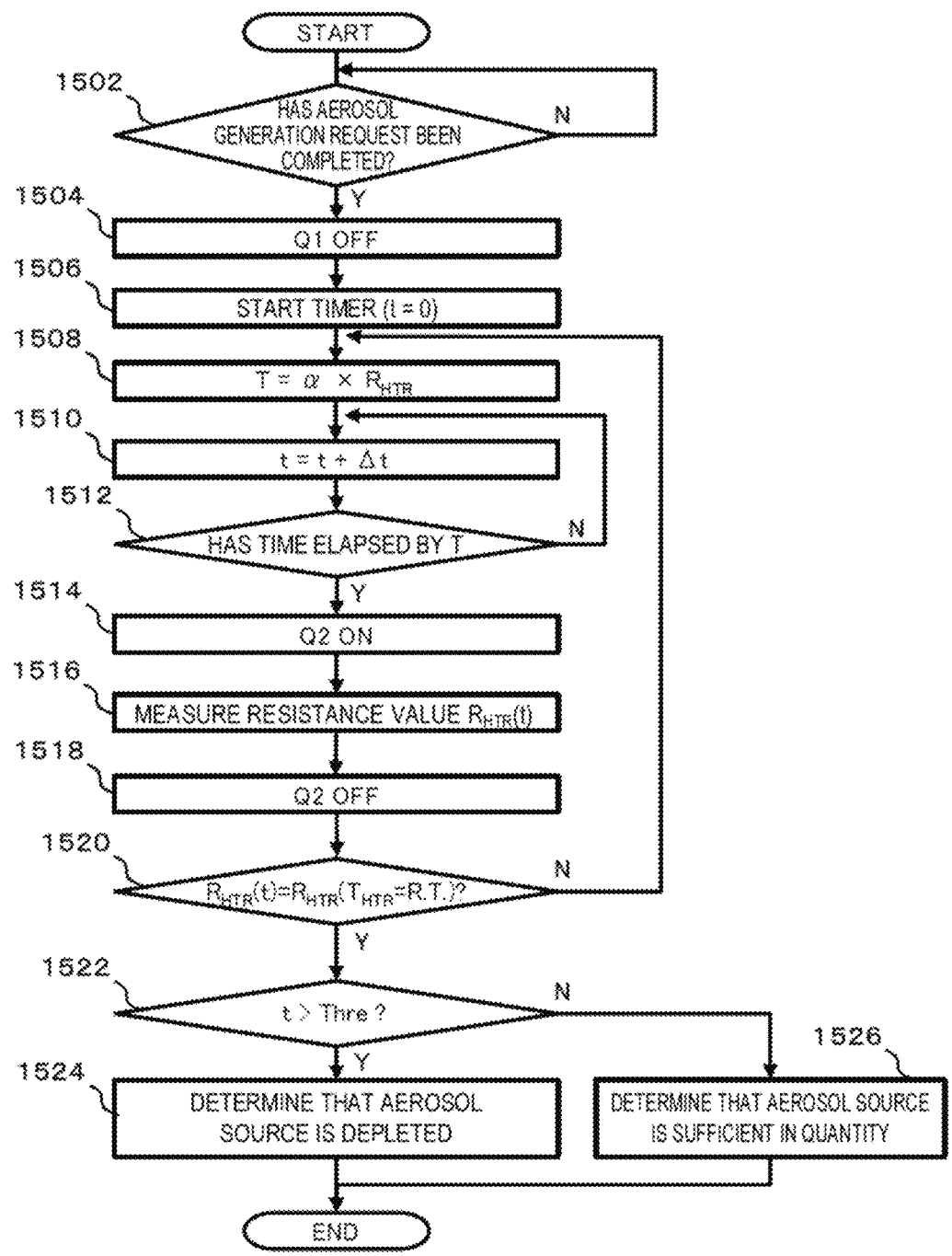
FIG. 15 is a flowchart of processing according to an embodiment of the present disclosure in connection with FIG. 14.

FIG. 15 is a flowchart of processing according to an embodiment of the present disclosure in connection with FIG. 14. The processes in steps 1502 to 1506 are the same as the processes in steps 402 to 406 in FIG. 4.

In step 1508, the control unit 106 determines a value of the measurement cycle T shown in FIG. 14. In an example, as illustrated in step 1508, the measurement cycle T may be obtained as a product of a predetermined coefficient α and the resistance value of the load 132 at that time. When the load 132 is a PTC heater, the resistance value of the load 132 is reduced as the temperature of the load 132 decreases. Therefore, according to the above-described example, "T" is shorter every time the value is measured. The above-described method of calculating "T" is illustrative only. As another example, the measurement cycle T may be calculated to be inversely proportional to the time period elapsed since the start of the cooling process, or may be calculated to be inversely proportional to the number of times of measurement that has already been made.

The process in step 1510 is the same as the process in step 408. The process proceeds to step 1512, and the control unit 106 determines whether the time has elapsed by the updated "T" after "T" has been updated in step 1508. When the time has not elapsed by "T" ("N" in step 1512), the process returns to before step 1510. When the time has elapsed by "T" ("Y" in step 1512), the process proceeds to step 1514. The processes in steps 1514 to 1520 are the same as the processes in steps 410 to 416.

When it is determined that the load 132 does not reach the room temperature ("N" in step 1520), the process returns to before step 1508, and new "T" is set, and the processes from steps 1508 to 1520 are repeated. When it is determined that the load 132 has reached the room temperature ("Y" in step 1520), the process proceeds to step 1522. The processes in steps 1522 to 1526 are the same as the processes in steps 418 to 422.

According to the embodiment of FIG. 14 and FIG. 15, the control unit 106 may be configured to shorten in a stepped manner the cycle in which a value of an electric resistance or an electric value related to the electric resistance is detected by the sensor 112 during monitoring of the cooling process. The control unit 106 may be configured to shorten the cycle in which a value of an electric resistance or an electric value related to the electric resistance is detected by the sensor 112 during monitoring of the cooling process, as the temperature of the load 132 corresponding to the value detected by the sensor 112 is low. With such features, the frequency of measurements can be appropriately set, whereby the influence on the cooling process of the load 132 becomes small.

Figure 16:
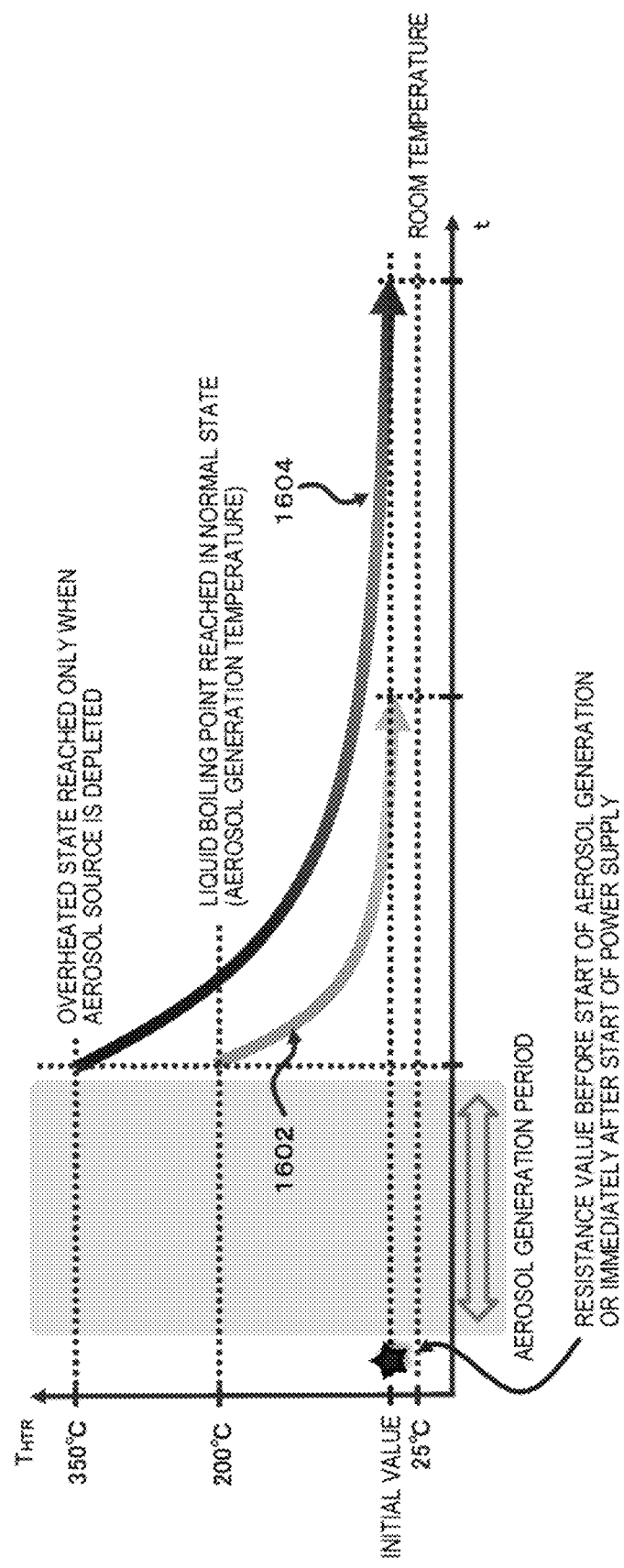
FIG. 16 schematically shows the power supply to the load and the cooling process of the load after stop of the power supply, according to an embodiment of the present disclosure.

FIG. 16 schematically shows the power supply to the load and the cooling process of the load after stop of the power supply, according to an embodiment of the present disclosure. A curve 1602 represents a cooling curve of the load 132 when the aerosol source is sufficient in quantity. A curve 1604 represents a cooling curve of the load 132 when the aerosol source is depleted (or is insufficient in quantity). An asterisk in FIG. 16 indicates a temperature of the load 132 corresponding to the resistance value of the load 132 before the aerosol generation starts or immediately after the power supply starts.

Figure 17:
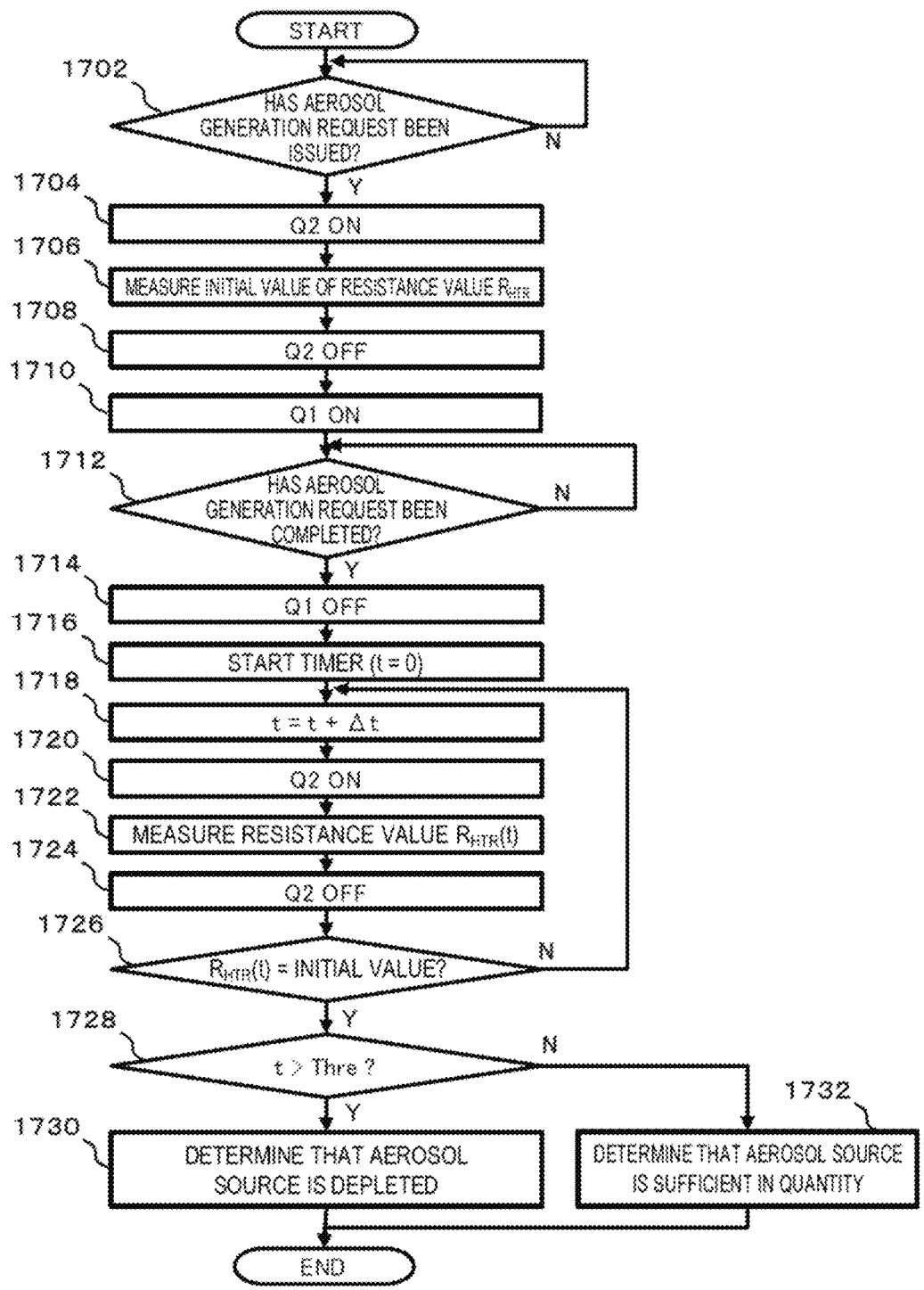
FIG. 17 is a flowchart of processing according to an embodiment of the present disclosure in connection with FIG. 16.

FIG. 17 is a flowchart of processing according to an embodiment of the present disclosure in connection with FIG. 16. In step 1702, the control unit 106 determines whether the aerosol generation request is issued. As an example, the control unit 106 may determine whether the user's inhalation is started, based on the output of the pressure sensor, or the like. In another example, the control unit 106 may determine whether the button provided in the aerosol generation device 100 to supply the electric power to the load 132 has been pressed.

The process proceeds to step 1704, and the control unit 106 turns on the switch Q2 before turning on the switch Q1. Next, in step 1706, the control unit 106 measures an electric resistance value of the load 132 or an electric value related to the electric resistance, in the above-described various methods. Here, the description will be made below assuming that the electric resistance value of the load 132 is measured. The control unit 106 stores, as an initial value, the electric resistance value measured in step 1706. In step 1708, the control unit 106 turns off the switch Q2. The process proceeds to step 1710, and the control unit 106 turns on the switch Q1 to start the power supply to the load 132.

The processes in steps 1712 to 1724 are the same as the processes in steps 402 to 414.

The process proceeds to step 1726, and the control unit 106 determines whether the resistance value $R_{HTR}(t)$ measured in step 1722 is equal to the initial value measured in step 1706. When both are not equal to each other ("N" in step 1726), the process returns to before step 1718. When both are equal to each other ("Y" in step 1726), the process proceeds to step 1728. The processes in steps 1728 to 1732 are the same as the processes in steps 418 to 422.

According to the embodiment of FIG. 16 and FIG. 17, the control unit 106 is configured to determine whether the depletion of the aerosol source has occurred, based on the cooling process until the value detected by the sensor 112 reaches a steady state. The cooling process is observed until the temperature of the load 132 reaches the steady state, and therefore the cooling process can be monitored until a proper end point. In an example, the control unit 106 may be configured to determine whether the value detected by the sensor 112 has reached the steady state, based on a comparison between the value detected by the sensor 112 before the electric power is supplied and the value detected by the sensor 112 in the cooling process. In this way, it is determined whether the value has reached the steady state based on the resistance value before the aerosol generation. Accordingly, the individual differences in the load 132 can be reflected as compared to the case where the determination is made based on the predetermined threshold, whereby the accuracy of the determination as to whether the value has reached the steady state is improved. In addition, even when the temperature in the use environment of the aerosol generation device 100 is different from a typical room temperature (e.g., 25° C.), the end point of the cooling process can be observed precisely.

Note that, instead of the above-described embodiment, in step 1726, the control unit 106 may determine whether the resistance value $R_{HTR}(t)$ measured in step 1722 is equal to a value obtained by adding an infinitesimal predetermined value Δ to the initial value measured in step 1706 or the value detected by the sensor 112 before the electric power is supplied, to reflect a measurement error of the sensor 112.

Figure 18:
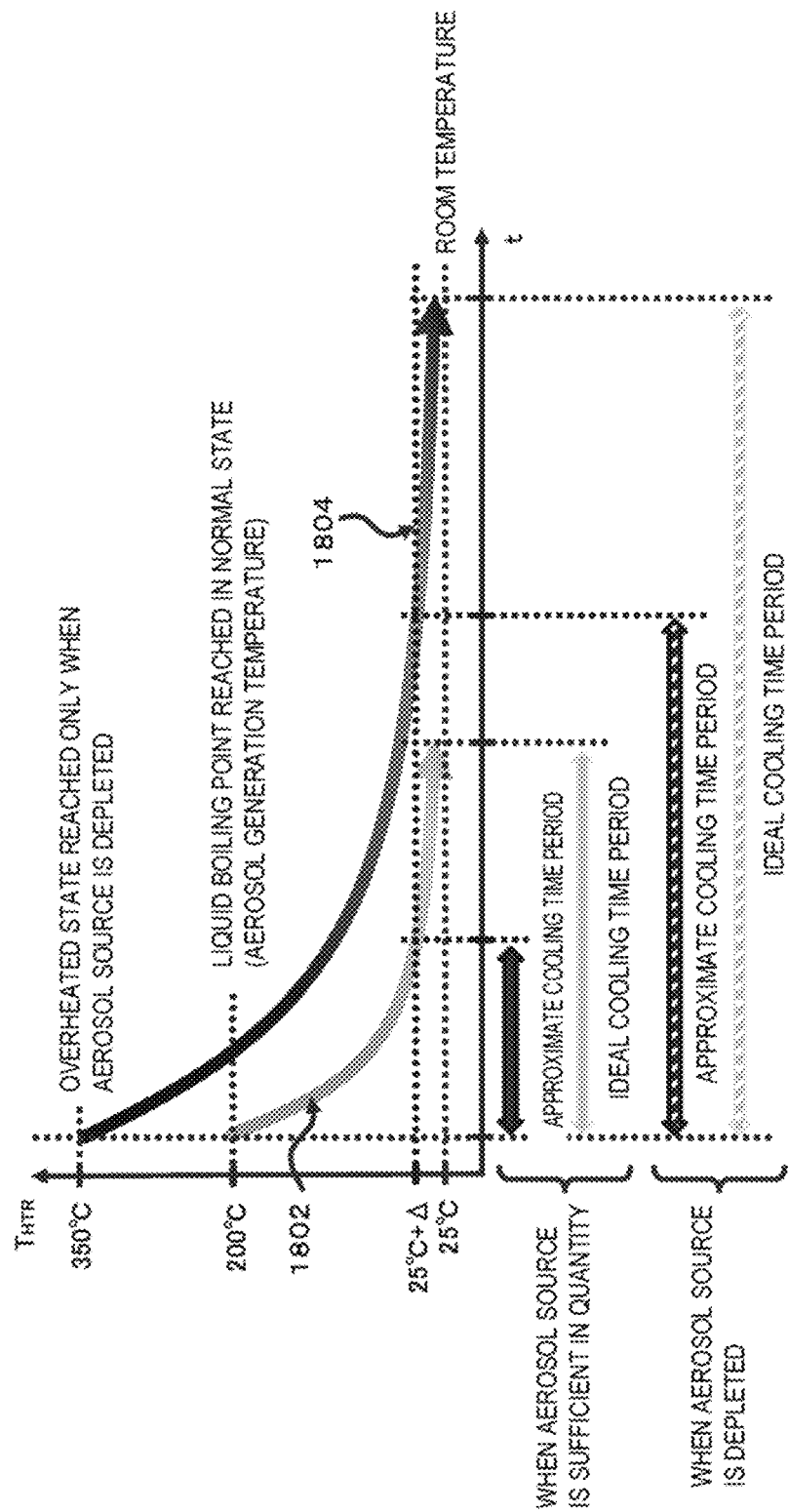
FIG. 18 conceptually shows a method of monitoring the cooling process of the load according to an embodiment of the present disclosure.

FIG. 18 conceptually shows a method of monitoring the cooling process of the load according to an embodiment of the present disclosure. A curve 1802 represents a cooling curve of the load 132 when the aerosol source is sufficient in quantity. A curve 1804 represents a cooling curve of the load 132 when the aerosol source is depleted (or is insufficient in quantity). In this example, instead of an ideal cooling period during which the temperature of the load 132 completely decreases to the room temperature (e.g., 25° C.), an approximate cooling period during which the temperature of the load 132 decreases to a temperature (e.g., 25° C.+Δ) higher than the room temperature is used as a time period until the value has reached the steady state.

Figure 19:
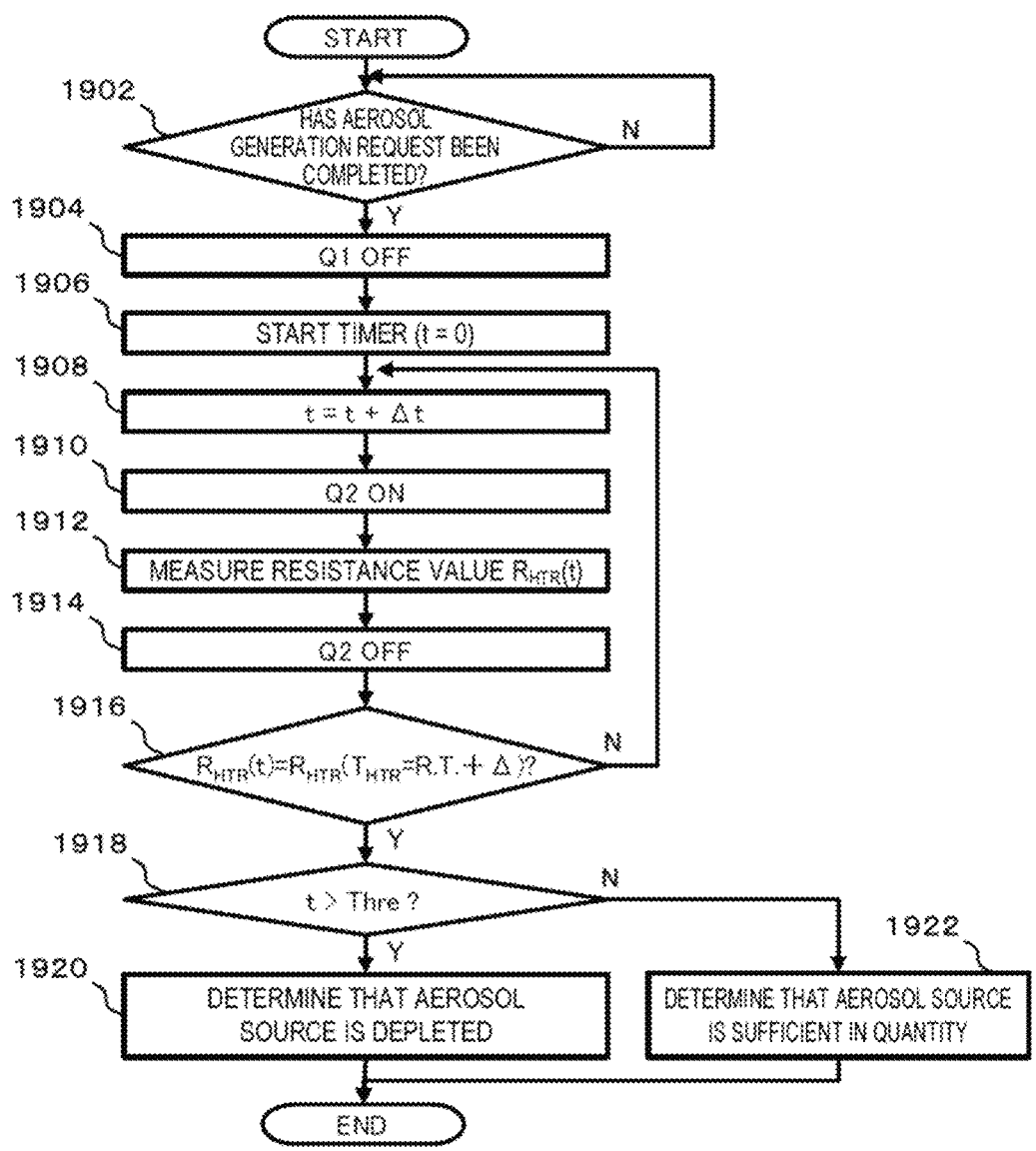
FIG. 19 is a flowchart of processing according to an embodiment of the present disclosure in connection with FIG. 18.

FIG. 19 is a flowchart of processing according to an embodiment of the present disclosure in connection with FIG. 18. The processes in steps 1902 to 1914 are the same as the processes in steps 402 to 414.

In step 1916, the control unit 106 compares the resistance value of the load 132 measured in step 1912 with the resistance value $(R_{HTR}(T_{HTR}=R.T.+\Delta))$ of the load 132 after all elapse of the above-described approximate cooling period, and determines whether both coincide with each other. The latter resistance value may be prestored in the memory 114. When both do not coincide with each other ("N" in step 1916), the process returns to before step 1908. When bath coincide with each other ("Y" in step 1916), the process proceeds to step 1918. The processes in steps 1918 to 1922 are the same as the processes in steps 418 to 422.

According to the embodiment of FIG. 18 and FIG. 19, the control unit 106 is configured to determine whether the depletion of the aerosol source has occurred, based on the cooling process until the value detected by the sensor 112 reaches a steady state. In an example, the control unit 106 is configured to determine whether the value detected by the sensor has reached the steady state, based on a comparison between the value detected by the sensor 112 corresponding to the temperature higher than the room temperature by a predetermined value and the value detected by the sensor 112 in the cooling process.

The value of Δ used in the embodiment of FIG. 18 and FIG. 19 may be set to be larger than an error in the temperature of the load obtained from the value detected by the sensor 112, the error being caused by an error of the sensor 112. As an example, when the sensor 112 is a voltage sensor, an error in the resistance value that can be measured using the voltage sensor can be obtained from the values of the measurement errors such as a gain error, an offset error, and a hysteresis error that are known for the voltage sensor. Furthermore, the error in the temperature that can be estimated for the load 132 can be obtained from an error in the resistance value that can be measured and an error in the temperature-resistance characteristic that is known for the load 132. In this case, it is only required that "Δ" is set to be larger than the error in the temperature that can be estimated for the load 132. This makes it possible to reflect the individual differences in the load 132 as compared to the case where the determination is made based on the predetermined threshold such as 25° C. corresponding to the room temperature, whereby the accuracy of the determination as to whether the value has reached the steady state is improved.

Figure 20:
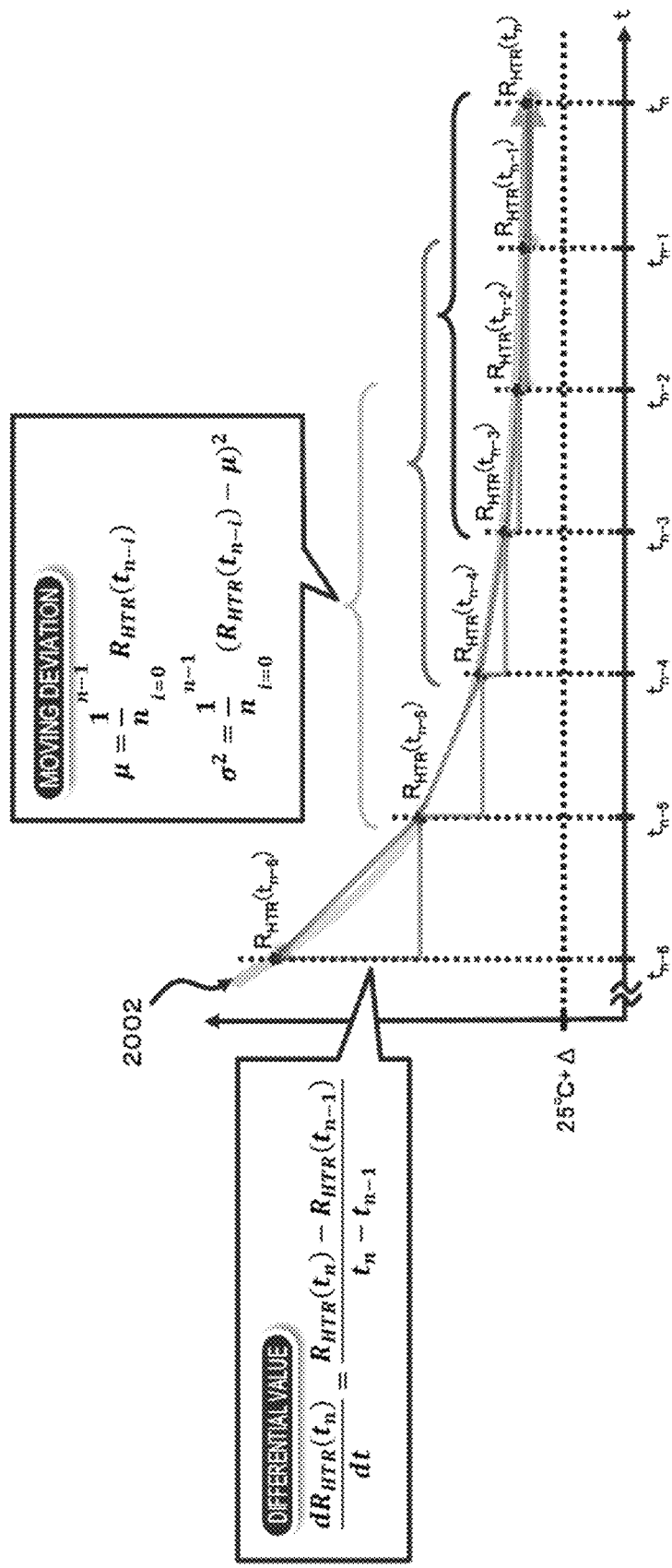
FIG. 20 conceptually shows a method of monitoring the cooling process of the load according to an embodiment of the present disclosure.

FIG. 20 conceptually shows a method of monitoring the cooling process of the load according to an embodiment of the present disclosure. A curve 2002 represents a cooling curve of the load 132. "$R_{HTR}(t_{n-6})$, $R_{HTR}(t_{n-5})$, . . . , and $R_{HTR}(t_n)$ represent resistance values of the load 132 measured at time points $t_{n-6}$, $t_{n-5}$, . . . , and $t_n$, respectively. Instead of the resistance values, electric values related to the resistances of the load 132 may be used. A time differential value, deviation, and variance of each of these values measured for the load 132 can be calculated using expressions shown in FIG. 20, for example. In this example, even when the estimated temperature of the load 132 has not reached the room temperature+Δ yet, it is determined whether the resistance value of the load 132 or the electric value related to the resistance value has reached the steady state, based on whether the above-described time differential value, deviation, or variance satisfies a predetermined condition.

Figure 21:
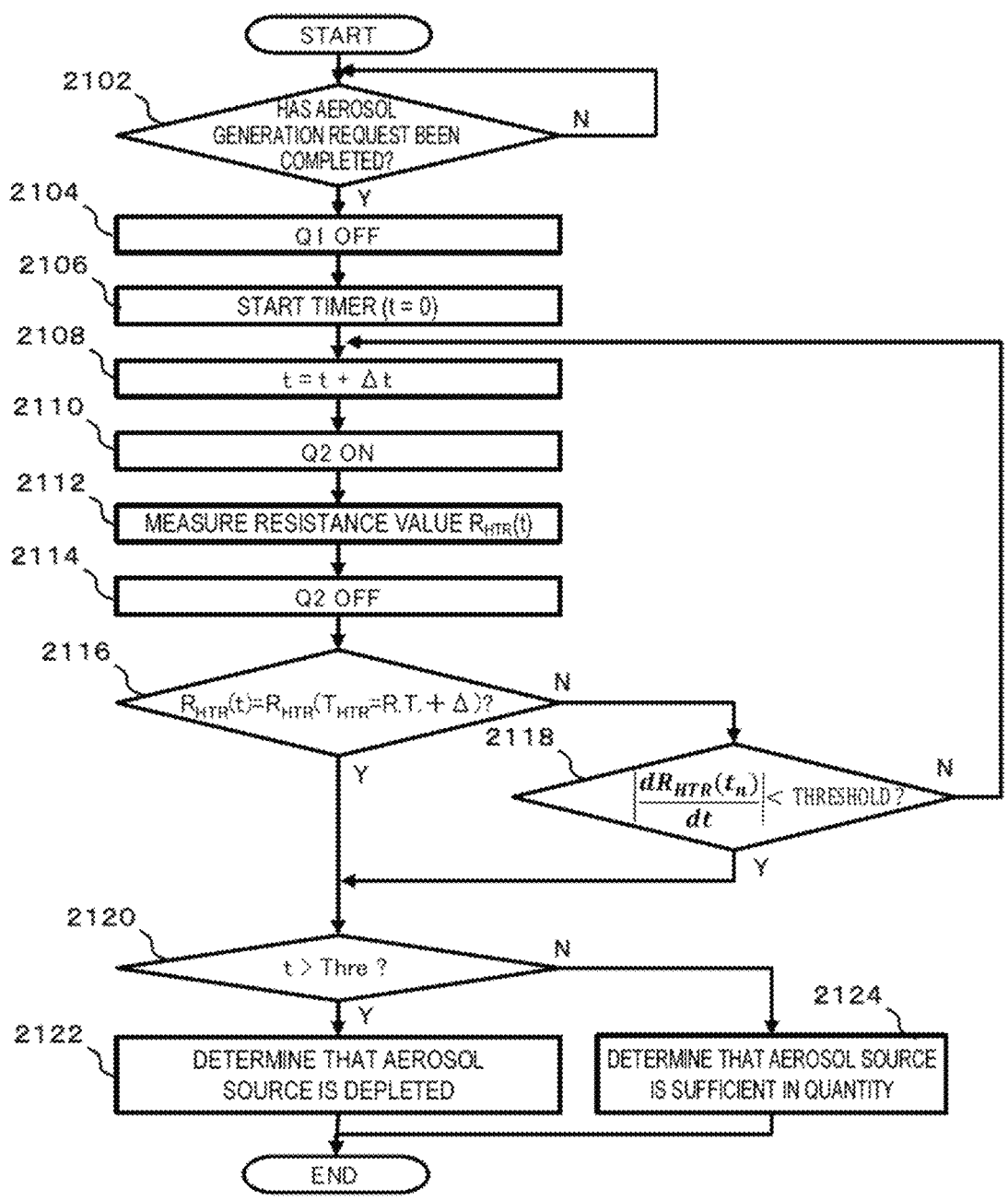
FIG. 21 is a flowchart of processing according to an embodiment of the present disclosure in connection with FIG. 20.

FIG. 21 is a flowchart of processing according to an embodiment of the present disclosure in connection with FIG. 20. The processes in steps 2102 to 2116 are the same as the processes in steps 1902 to 1916 in FIG. 19.

When in step 2116, it is determined that the load 132 does not reach the predetermined steady state ("N" in step 2116), the process proceeds to step 2118. In step 2118, the control unit 106 determines whether an absolute value of the time differential value of the resistance value (or the electric value related to the resistance value) of the load 132 is smaller than a predetermined threshold. When the absolute value is equal to or larger than the threshold ("N" in step 2118), the process returns to before step 2108. When the absolute value is smaller than the threshold ("Y" in step 2118), the process proceeds to step 2120. Note that the condition in step 2118 may further include a condition where the above-described time differential value is equal to or smaller than zero. This can avoid erroneously determining that the value has reached the steady state when the cooling curve 2002 vibrates and the slope of the curve 2002 is positive. The processes in steps 2120 to 2124 are the same as the processes in steps 1918 to 1922.

Figure 22:
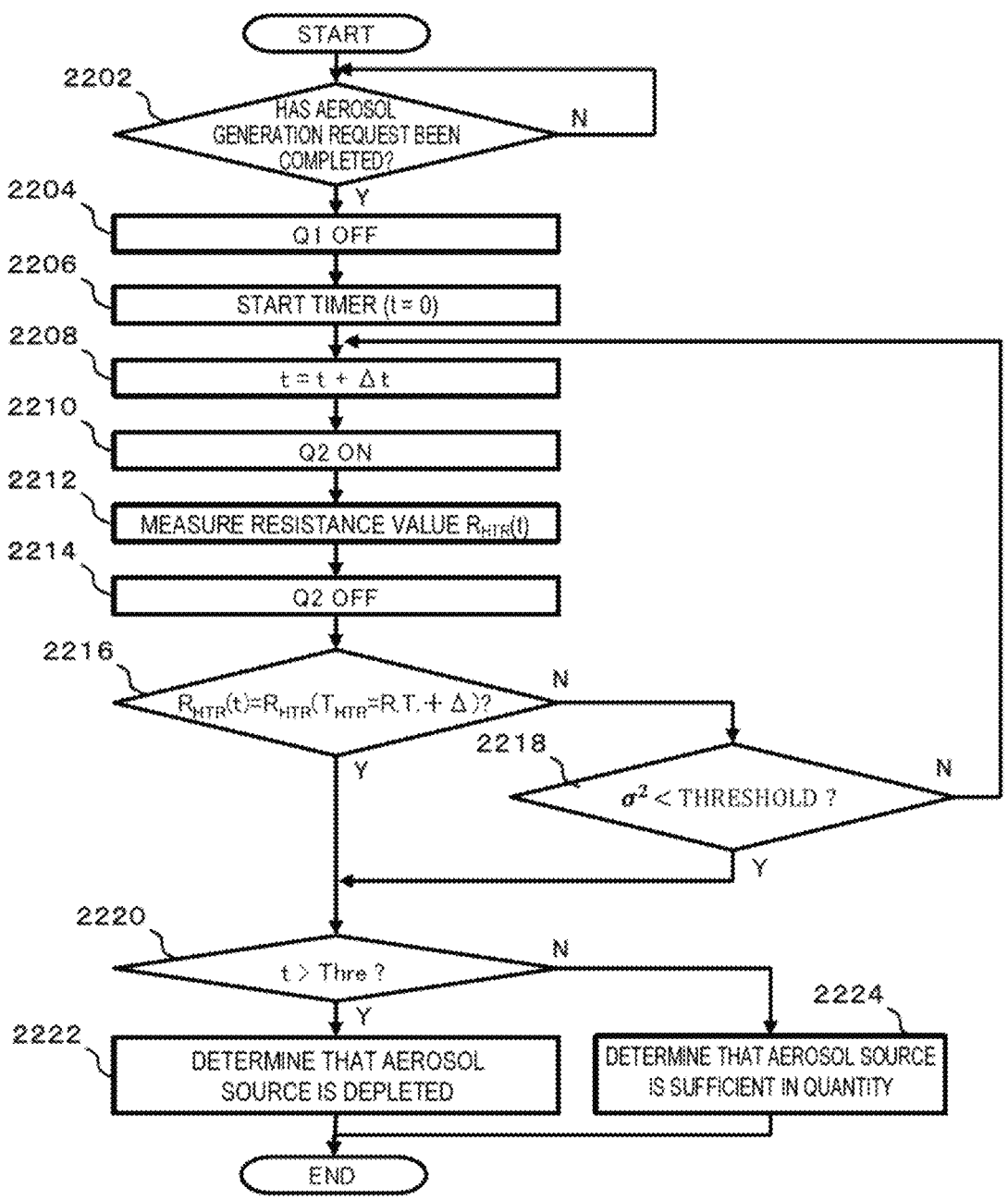
FIG. 22 is a flowchart of processing according to an embodiment of the present disclosure in connection with FIG. 20.

FIG. 22 is a flowchart of processing according to an embodiment of the present disclosure in connection with FIG. 20. The processes in steps 2202 to 2216 are the same as the processes in steps 2102 to 2116 in FIG. 21.

When in step 2216, it is determined that the load 132 does not reach the predetermined steady state ("N" in step 2216), the process proceeds to step 2218. In step 2218, the control unit 106 determines whether the variance of the resistance value (or the electric value related to the resistance value) of the load 132 is smaller than a predetermined threshold. Instead of the variance, the deviation may be used for the determination. When the variance is equal to or larger than the threshold ("N" in step 2218), the process returns to before step 2208. When the variance is smaller than the threshold ("Y" in step 2218), the process proceeds to step 2220. The processes in steps 2220 to 2224 are the same as the processes in steps 2120 to 2124.

According to the embodiment of FIG. 20, FIG. 21, and FIG. 22, the control unit 106 is configured to determine whether the value detected by the sensor 112 has reached the steady state, based on the time differential value, the deviation, or the variance of the value detected by the sensor 112. The time-series change in the value is reflected as compared to the case where the value itself detected by the sensor 112 is used, which makes it easy to determine that the value has reached the steady state.

As described above, according to the first embodiment of the present disclosure, the control unit 106 can be configured to cause the sensor 112 to detect the value during monitoring of the cooling process at timing when the temperature of the load 132 does not diverge from the value of the electric resistance of the load 132 or the electric value related to the electric resistance, or with a frequency that does not interfere with the cooling of the load 132 in the cooling process. Accordingly, the cooling process of the load can be observed with high accuracy even without using the dedicated temperature sensor.

In addition, according to the first embodiment of the present disclosure, the control unit 106 can be configured to determine whether the depletion of the aerosol source in the storage unit 116A or the aerosol base material 116B has occurred, based on the time-series change in the value detected by the sensor 112 in the cooling process after a point when or immediately after the cooling of the load 132 starts and before a point when the load 132 reaches the room temperature. In an example, the control unit 106 can be configured to determine whether the value detected by the sensor 112 has reached the steady state, based on the value detected by the sensor 112 or the time-series change in the value, and determine whether the depletion has occurred, based on the cooling process until the value detected by the sensor 112 reaches the steady state. Accordingly, the cooling process of the load can be observed with high accuracy even without using the dedicated temperature sensor.

In the above description, the first embodiment of the present disclosure has been described as an aerosol generation device and a method of operating the aerosol generation device. However, it will be appreciated that the present disclosure, when being executed by a processor, can be implemented as a program that causes the processor to perform the method or as a computer readable storage medium storing the same program.

Second Embodiment

When the load 132 (or the heater) is cooled, the following expression is established using Newton's law of cooling, for convenience assuming that heat is exchanged only among the load 132, a member (e.g., the retention unit 130, and hereinafter, referred to as a "wick") that carries the aerosol source from the storage unit 116A to the load 132 using a capillary effect and the aerosol source retained in the wick, and the atmosphere.

[Formula 1]

$$-\frac{dQ_{HTR}}{dt} = \alpha_{wick}S_{wick}(T_{HTR} - T_{wick}) + \alpha_{liquid}S_{liquid}(T_{HTR} - T_{liquid}) + \alpha_{air}S_{air}(T_{HTR} - T_{air}) \quad (1)$$

Where "$Q_{HTR}$" represents an amount of heat of the load 132. "$\alpha_{wick}$," "$\alpha_{liquid}$," and "$\alpha_{air}$" are thermal conductivities of the wick, the aerosol source retained in the wick, and the atmosphere, respectively. "$S_{wick}$," "$S_{liquid}$," and "$S_{air}$" are surface areas of the load 132 with respect to the wick, the aerosol source retained in the wick, and the atmosphere, respectively. "$T_{HTR}$," "$T_{wick}$," "$T_{liquid}$," and "$T_{air}$" are temperatures of the load 132, the wick, the aerosol source retained in the wick, and the atmosphere, respectively.

In addition, the following expression is established for the amount of heat of the load 132.

[Formula 2]

$$\frac{dQ_{HTR}}{dt} = C_{HTR}\frac{dT_{HTR}}{dt} \quad (2)$$

Where "$C_{HTR}$" represents a thermal capacity of the load 132.

Summarizing the expression (1) and the expression (2), the following expression is established.

[Formula 3]

$$C_{HTR}\frac{dT_{HTR}}{dt} = -\alpha_{wick}S_{wick}(T_{HTR} - T_{wick}) - \quad (3)$$
$$\alpha_{liquid}S_{liquid}(T_{HTR} - T_{liquid}) - \alpha_{air}S_{air}(T_{HTR} - T_{air})$$
$$\frac{dT_{HTR}}{dT} = -\frac{\alpha_{wick}S_{wick}}{C_{HTR}}(T_{HTR} - T_{wick}) -$$
$$\frac{\alpha_{liquid}S_{liquid}}{C_{HTR}}(T_{HTR} - T_{liquid}) - \frac{\alpha_{air}S_{air}}{C_{HTR}}(T_{HTR} - T_{air})$$

For the sake of simplicity, relaxation times r are defined by the following expressions (4) to (6).

[Formula 4]

$$\tau_{wick} \equiv \left(\frac{\alpha_{wick}S_{wick}}{C_{HTR}}\right)^{-1} \quad (4)$$

$$\tau_{liquid} \equiv \left(\frac{\alpha_{liquid}S_{liquid}}{C_{HTR}}\right)^{-1} \quad (5)$$

$$\tau_{air} \equiv \left(\frac{\alpha_{air}S_{air}}{C_{HTR}}\right)^{-1} \quad (6)$$

The expression (3) can be rewritten as follows using the expressions (4) to (6).

[Formula 5]

$$\frac{dT_{HTR}}{dt} = -\frac{T_{HTR} - T_{wick}}{\tau_{wick}} - \frac{T_{HTR} - T_{liquid}}{\tau_{liquid}} - \frac{T_{HTR} - T_{air}}{\tau_{air}}\frac{dT_{HTR}}{dt} = \quad (7)$$
$$-\left(\frac{1}{\tau_{wick}} + \frac{1}{\tau_{liquid}} + \frac{1}{\tau_{air}}\right)T_{HTR} + \frac{T_{wick}}{\tau_{wick}} + \frac{T_{liquid}}{\tau_{liquid}} + \frac{T_{air}}{\tau_{air}}$$

For the sake of further simplicity, the expression (7) is rewritten as follows.

[Formula 6]

$$\frac{dT_{HTR}}{dt} = -\sum_{i}^{coolant}\frac{1}{\tau_i} \cdot T_{HTR} + \sum_{i}^{coolant}\frac{T_i}{\tau_i} \quad (8)$$

Note that the mathematical expressions defined by the following expression (9) and expression (10) are used for the above rewriting of the expression.

[Formula 7]

$$\sum_{i}^{coolant}\frac{1}{\tau_i} \equiv \frac{1}{\tau_{wick}} + \frac{1}{\tau_{liquid}} + \frac{1}{\tau_{air}} \quad (9)$$

$$\sum_{i}^{coolant}\frac{T_i}{\tau_i} \equiv \frac{T_{wick}}{\tau_{wick}} + \frac{T_{liquid}}{\tau_{liquid}} + \frac{T_{air}}{\tau_{air}} \quad (10)$$

To solve the differential expression (8), a new variable $T_1$ is introduced using the following expression (11).

[Formula 8]

$$T_1 \equiv -\sum_{i}^{coolant}\frac{1}{\tau_i} \cdot T_{HTR} + \sum_{i}^{coolant}\frac{T_i}{\tau_i} \quad (11)$$

The variable transformation is applied to the differential expression (8) using the expression (11).

[Formula 9]

$$\frac{d}{dt}\left\{\left(\sum_{i}^{coolant}\frac{1}{\tau_i}\right)^{-1}\left(\sum_{i}^{coolant}\frac{T_i}{\tau_i} - T_1\right)\right\} = \quad (12)$$
$$-\sum_{i}^{coolant}\frac{1}{\tau_i} \cdot \left(\sum_{i}^{coolant}\frac{1}{\tau_i}\right)^{-1} \cdot \left(\sum_{i}^{coolant}\frac{T_i}{\tau_i} - T_1\right) + \sum_{i}^{coolant}\frac{T_i}{\tau_i}$$
$$\left(\sum_{i}^{coolant}\frac{1}{\tau_i}\right)^{-1}\left(\frac{d}{dt}\sum_{i}^{coolant}\frac{T_i}{\tau_i} - \frac{d}{dt}T_1\right) = -\sum_{i}^{coolant}\frac{T_i}{\tau_i} + T_1 + \sum_{i}^{coolant}\frac{T_i}{\tau_i}$$
$$\left(\frac{d}{dt}\sum_{i}^{coolant}\frac{T_i}{\tau_i} - \frac{d}{dt}T_1\right) = \sum_{i}^{coolant}\frac{1}{\tau_i} \cdot T_1$$

Assuming that each of the wick, the aerosol source retained in the wick, and the atmosphere has a sufficient large thermal capacity with respect to the load 132 in the cooling process of the load 132, the temperature changes of the wick, the aerosol source retained in the wick, and the atmosphere in the cooling process of the load 132 are negligibly small. Accordingly, the first term of the left side of the differential expression (12) can be regarded as zero, and therefore the differential expression (12) can be modified as follows.

[Formula 10]

$$-\frac{d}{dt}T_1 \cong \sum_{i}^{coolant}\frac{1}{\tau_i} \cdot T_1 \quad (13)$$

The following expression is obtained by solving the differential expression (13) using the separation of variables.

[Formula 11]

$$\frac{1}{T_1}dT_1 \cong -\sum_{i}^{coolant}\frac{1}{\tau_i} \cdot dt \quad (14)$$

$$\int \frac{1}{T_1} dT_1 \cong -\sum_i^{coolant} \frac{1}{\tau_i} \int dt$$

$$\log T_1 \cong -\sum_i^{coolant} \frac{1}{\tau_i} \cdot t + C$$

$$T_1(t) \cong e^C \cdot \exp\left(-\sum_i^{coolant} \frac{1}{\tau_i} \cdot t\right)$$

Where "C" represents an integral constant.

When a value at t=0 is obtained by regarding the expression (11) as a function of time t, the following expression is obtained.

[Formula 12]

$$T_1(0) = -\sum_i^{coolant} \frac{1}{\tau_i} \cdot T_{HTR}(0) + \sum_i^{coolant} \frac{T_i}{\tau_i} \quad (15)$$

Where "$T_{HTR}(0)$" represents a temperature of the load 132 at t=0, i.e., when the cooling process of the load 132 starts. When the expression (15) is used for a boundary condition of the expression (14), the following expression is established.

[Formula 13]

$$e^C = -\sum_i^{coolant} \frac{1}{\tau_i} \cdot T_{HTR}(0) + \sum_i^{coolant} \frac{T_i}{\tau_i} \quad (16)$$

The expression (14) can be solved for "$T_{HTR}(t)$" as follows, using the expression (11) and the expression (16).

[Formula 14]

$$T_1(t) \cong \left(-\sum_i^{coolant} \frac{1}{\tau_i} \cdot T_{HTR}(0) + \sum_i^{coolant} \frac{T_i}{\tau_i}\right) \cdot \exp\left(-\sum_i^{coolant} \frac{1}{\tau_i} \cdot t\right) - \quad (17)$$

$$\sum_i^{coolant} \frac{1}{\tau_i} \cdot T_{HTR} + \sum_i^{coolant} \frac{T_i}{\tau_i} \cong$$

$$\left(-\sum_i^{coolant} \frac{1}{\tau_i} \cdot T_{HTR}(0) + \sum_i^{coolant} \frac{T_i}{\tau_i}\right) \cdot \exp\left(-\sum_i^{coolant} \frac{1}{\tau_i} \cdot t\right) -$$

$$\sum_i^{coolant} \frac{1}{\tau_i} \cdot T_{HTR} \cong$$

$$\left(-\sum_i^{coolant} \frac{1}{\tau_i} \cdot T_{HTR}(0) + \sum_i^{coolant} \frac{T_i}{\tau_i}\right) \cdot \exp\left(-\sum_i^{coolant} \frac{1}{\tau_i} \cdot t\right) - \sum_i^{coolant} \frac{T_i}{\tau_i}$$

$$T_{HTR} \cong$$

$$-\left(\sum_i^{coolant} \frac{1}{\tau_i}\right)^{-1} \left(-\sum_i^{coolant} \frac{1}{\tau_i} \cdot T_{HTR}(0) + \sum_i^{coolant} \frac{T_i}{\tau_i}\right) \cdot \exp\left(-\sum_i^{coolant} \frac{1}{\tau_i} \cdot t\right) +$$

$$\left(\sum_i^{coolant} \frac{1}{\tau_i}\right)^{-1} \sum_i^{coolant} \frac{T_i}{\tau_i}$$

The inventors of the present application have discovered that when the expression (17) is differentiated with respect to time, the time differential of the temperature of the load 132 (cooling rate) can be approximated by the following expression.

[Formula 15]

$$\frac{d}{dt} T_{HTR} \cong -\frac{d}{dt}\left(\sum_i^{coolant} \frac{1}{\tau_i}\right)^{-1} \quad (18)$$

$$\left(-\sum_i^{coolant} \frac{1}{\tau_i} \cdot T_{HTR}(0) + \sum_i^{coolant} \frac{T_i}{\tau_i}\right) \cdot \exp\left(-\sum_i^{coolant} \frac{1}{\tau_i} \cdot t\right) +$$

$$\frac{d}{dt}\left(\sum_i^{coolant} \frac{1}{\tau_i}\right)^{-1} \sum_i^{coolant} \frac{T_i}{\tau_i}$$

$$\frac{d}{dt} T_{HTR} \cong -\left(\sum_i^{coolant} \frac{1}{\tau_i}\right)^{-1}\left(-\sum_i^{coolant} \frac{1}{\tau_i} \cdot T_{HTR}(0) + \sum_i^{coolant} \frac{T_i}{\tau_i}\right) \cdot \frac{d}{dt}$$

$$\exp\left(-\sum_i^{coolant} \frac{1}{\tau_i} \cdot t\right) + 0$$

$$\frac{d}{dt} T_{HTR} \cong \left(-\sum_i^{coolant} \frac{1}{\tau_i} \cdot T_{HTR}(0) + \sum_i^{coolant} \frac{T_i}{\tau_i}\right) \cdot \exp\left(-\sum_i^{coolant} \frac{1}{\tau_i} \cdot t\right)$$

As described above, if the temperature changes of the wick, the aerosol source retained in the wick, and the atmosphere in the cooling process of the load 132 are negligibly small, the time-series change in the temperature of the load is largely affected by "$T_{HTR}(0)$". That is, it can be understood that the higher the temperature of the load when the cooling process starts is, the easier it is to decrease the temperature of the load.

From the above considerations, the inventors of the present application arrived at the technical idea in which the cooling rate of the load 132 is used to determine whether the aerosol source has been depleted.

Figure 23:
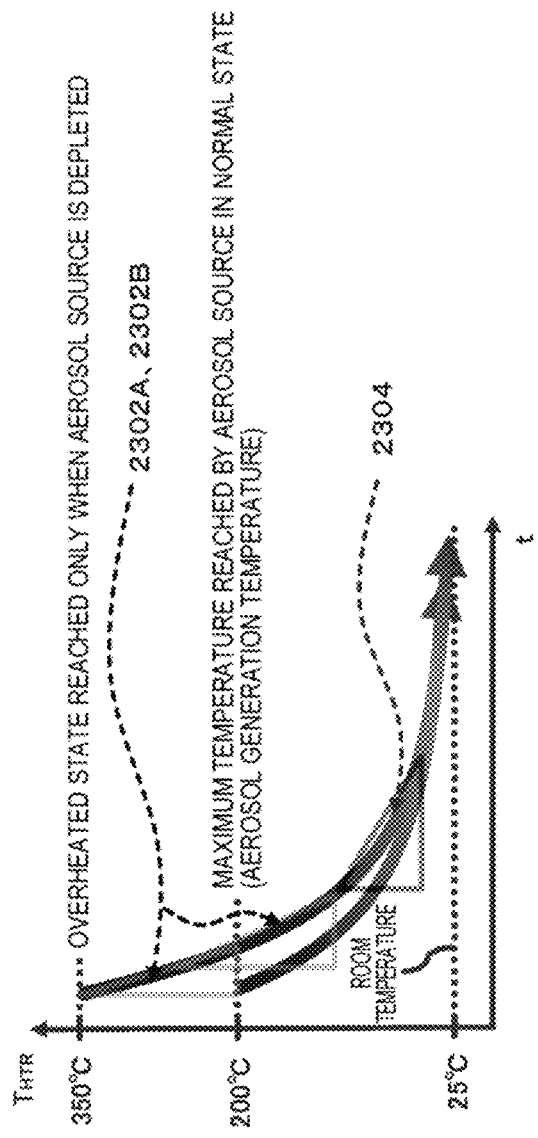
FIG. 23 is a graph schematically showing the cooling process of the load after the power supply to the load is stopped in the aerosol generation device.

FIG. 23 is a graph schematically showing the cooling process of the load 132 after the power supply to the load 132 is stopped in the aerosol generation device 100. The horizontal axis represents time, and the vertical axis represents a temperature of the load. Here, it is assumed that the maximum temperature reached by the aerosol source in the normal state is 200° C., and the temperature reached by the load 132 in the overheated state due to depletion of the aerosol source is 350° C. as an example.

As described above, the higher the temperature of the load 132 is, the larger the decrease rate of the temperature of the load 132 is. Accordingly, in the example of FIG. 23, in order to detect the depletion of the aerosol source, it is desirable that the rate of change in the temperature of the load 132 is measured in regions, such as regions 2302A and 2302B, including the temperature exceeding the maximum temperature reached by the aerosol source in the normal state. Conversely, a region, such as a region 2304, including the temperature equal to or lower than the maximum temperature reached by the aerosol source in the normal state is not suitable to measure the rate of change in the temperature of the load 132 in order to detect the depletion of the aerosol source.

FIG. 24 is a chart showing an actual cooling rate of the load 132. FIG. 24(A) shows a cooling rate when the aerosol source is sufficient in quantity. FIG. 24 (B) shows a cooling rate when the aerosol source is depleted (or is insufficient in quantity). In FIG. 24(A) and FIG. 24(B), the horizontal axis represents time, and the vertical axis represents the cooling rate of the load 132 that is observed via the electric resistance value of the load 132. Note that FIG. 24(A) and FIG. 24(B) have the same scale of the vertical axis.

When the observation of the cooling process of the load 132 is divided into a region 2402, a region 2404, and a region 2406 in a time series order after heating of the load 132 is stopped near about 4.8 seconds, the following can be found.

Since the region 2402 starts immediately after the heating of the load 132 is stopped, the cooling rate of the load 132 is strongly affected by the disturbance such as the above-described surge current and residual current in the region 2402. Accordingly, in the case where the cooling rate is observed via the electric resistance value of the load 132, it is difficult to use the cooling rate of the load 132 in the region 2402 for the determination as to whether the aerosol source has been depleted. Note that it will be apparent to those skilled in the art that such a concern hardly arises in the case where the cooling rate of the load 132 is observed using the dedicated temperature sensor.

Figure 24:
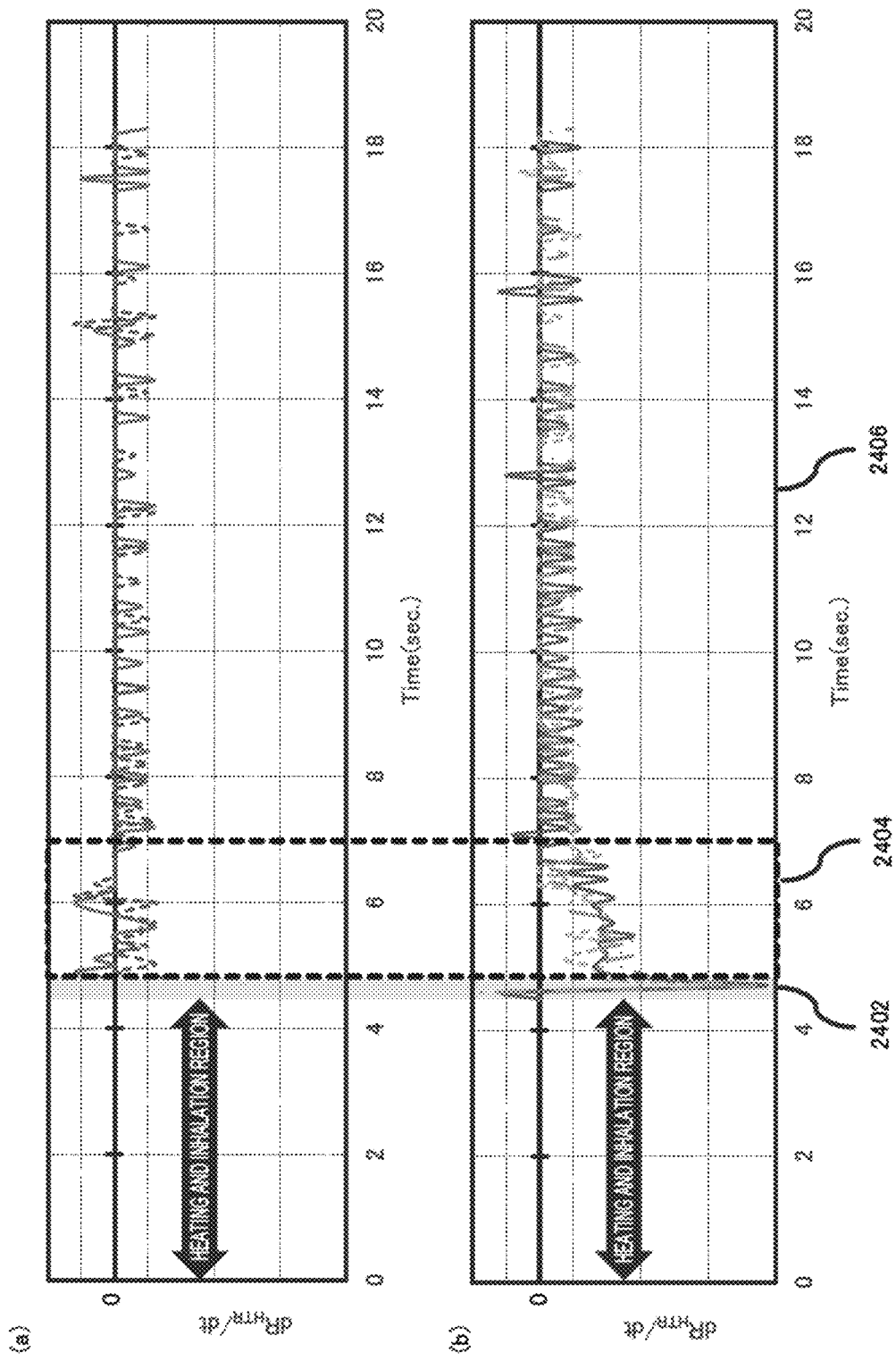
FIG. 24 is a chart showing an actual cooling rate of the load.

In the region 2404, the cooling rate when the aerosol source is sufficient in quantity as shown in FIG. 24(A) is largely different from the cooling rate when the aerosol source is depleted (or is insufficient in quantity) as shown in FIG. 24(B). It is believed that this is because the above-described difference in the temperature of the load causes a significant difference in the cooling rate. Accordingly, the cooling rate of the load 132 in the region 2404 is suitable for the determination as to whether the aerosol source has been depleted.

In the region 2406, the cooling rate when the aerosol source is sufficient in quantity as shown in FIG. 24(A) is almost the same as the cooling rate when the aerosol source is depleted (or is insufficient in quantity) as shown in FIG. 24(B). It is believed that this is because the cooling rate is observed at the temperature equal to or lower than the above-described maximum temperature reached by the aerosol source in the normal state. Accordingly, the cooling rate of the load 132 in the region 2406 is unsuitable for the determination as to whether the aerosol source has been depleted.

Figure 25:
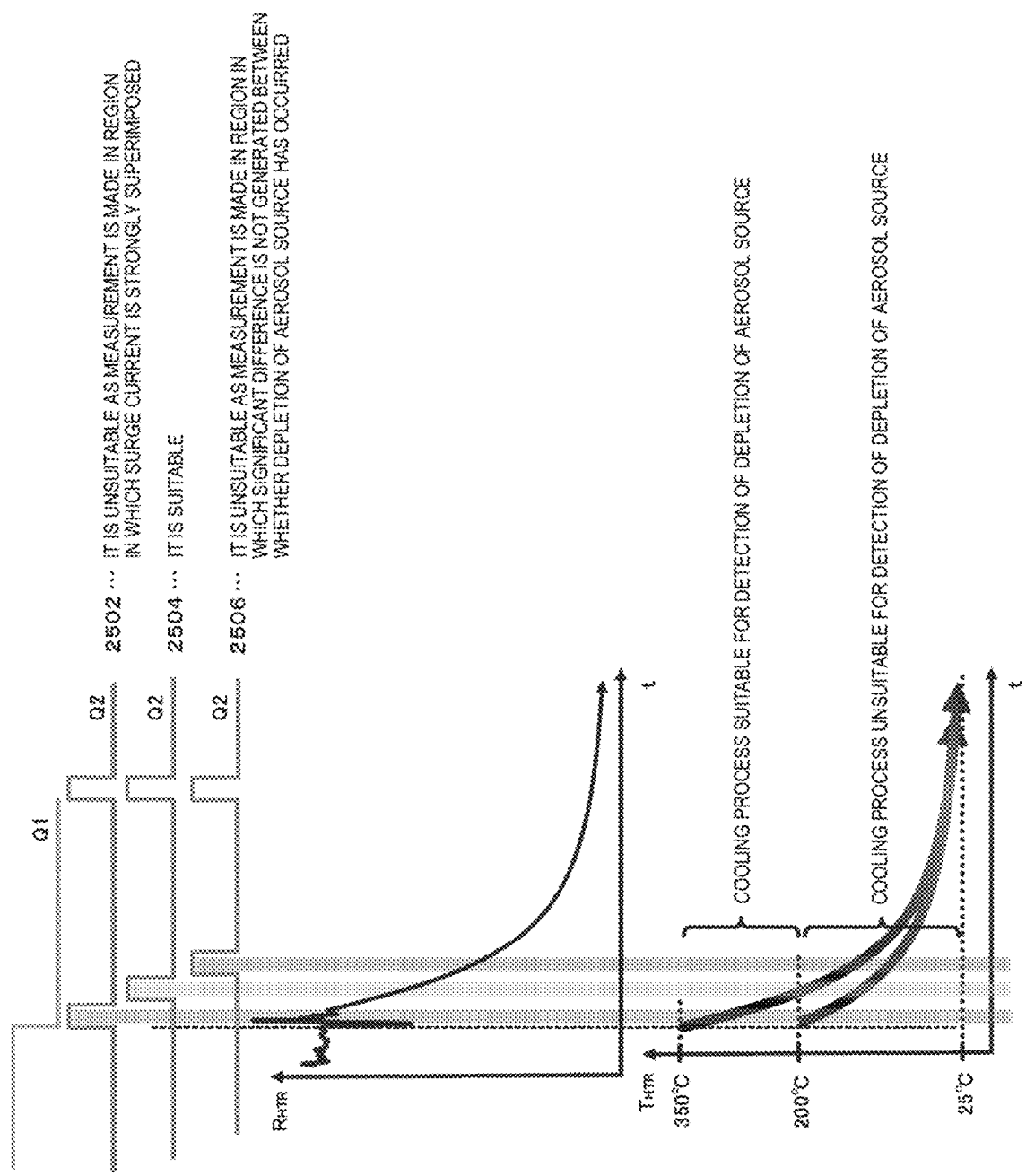
FIG. 25 is a chart tier explaining timing suitable for measuring the cooling rate of the load.

FIG. 25 is a chart for explaining timing suitable for measuring the cooling rate of the load 132. As described in connection with FIG. 23, measuring the cooling rate at the earliest timing possible after the switch Q1 is turned off and the cooling of the load 132 starts allows more accurate determination as to whether the aerosol source has been depleted. However, when the switch Q2 is turned on immediately after the switch Q1 is turned off as indicated by reference numeral 2502, the value related to the measured temperature of the load 132 fluctuates largely due to an influence of the surge current and the like. Accordingly, it is difficult to measure the cooling rate accurately. On the other hand, even when the measurement is made after the switch Q2 is turned on at the timing when the temperature of the load 132 becomes equal to or lower than the boiling point of the aerosol source as indicated by reference numeral 2506, a significant difference hardly occurs between the case where the aerosol source is depleted and the case where the aerosol source is sufficient in quantity. From these, the inventors of the present application have reached the idea that it is desirable that the cooling rate is measured at the timing when the temperature of the load 132 may belong to a temperature range achievable only when the depletion of the aerosol source occurs after an elapse of a predetermined time period since turning off of the switch Q1 (after the set dead zone is passed), as indicated by reference numeral 2504.

Figure 26:
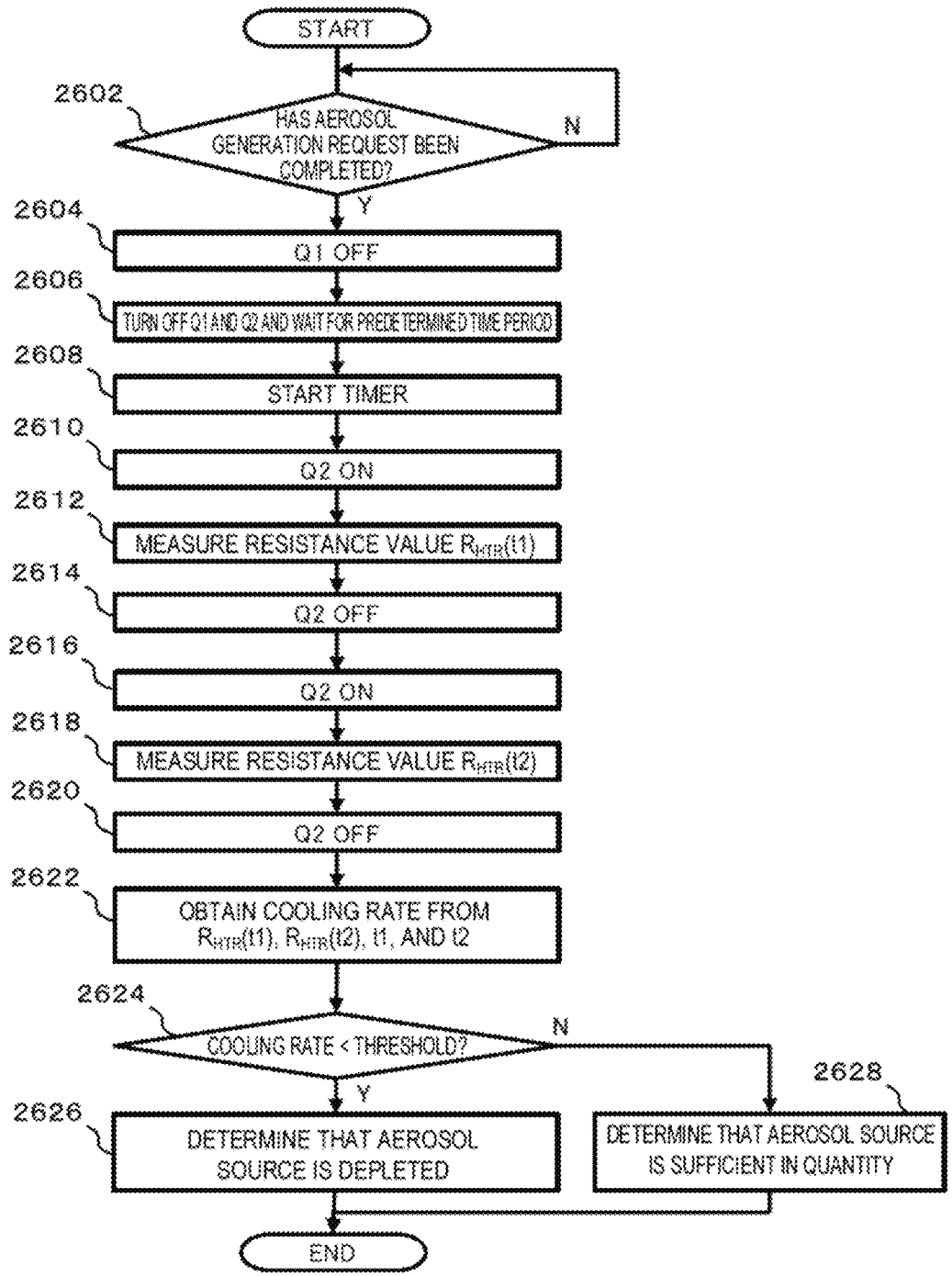
FIG. 26 is a flowchart of processing for detecting the depletion of the aerosol source, according to an embodiment of the present disclosure.

FIG. 26 is a flowchart of processing for detecting the depletion of the aerosol source, according to an embodiment of the present disclosure. Here, all the steps will be described as being performed by the control unit 106. However, it should be noted that some of the steps may be performed by another component in the aerosol generation device 100.

The process starts at step 2602, and the control unit 106 determines Whether the aerosol generation request has been completed. As an example, the control unit 106 may determine whether user's inhalation has been completed, based on output of the pressure sensor, and the like. In another example, the control unit 106 may determine whether the aerosol generation request has been completed, based on whether a button provided in the aerosol generation device 100 to supply the electric power to the load 132 is no longer pressed. In still another example, the control unit 106 may determine whether the aerosol generation request has been completed, based on whether a predetermined time period has elapsed since detection of an operation on a user interface such as pressing the button provided in the aerosol generation device 100 to supply the electric power to the load 132.

When the aerosol generation request is continued ("N" in step 2602), the process returns to before step 2602. When the aerosol generation request is completed ("Y" in step 2602), the process proceeds to step 2604. In step 2604, the control unit 106 turns off the switch Q1, and stops the power supply to the load 132.

The process proceeds to step 2606, and the control unit 106 waits for a predetermined time period in a state in which both of the switch Q1 and the switch Q2 are off. That is, a dead zone in which the cooling process is not monitored or the determination, based on the monitored cooling process, as to whether the depletion has occurred is not made is provided when or immediately after the cooling process of the load 132 starts. The dead zone may be provided until a time point after the surge current is attenuated and a time point before the temperature of the load 132 becomes equal to or lower than the boiling point of the aerosol source.

The process proceeds to step 2608, and the control unit 106 starts a timer. The control unit 106 may set a value of the timer to an initial value t=0.

The process proceeds to step 2610, and the control unit 106 turns on the switch Q2 to cause the second circuit 204 to function. The process proceeds to step 2612, and the control unit 106 measures a value related to the temperature of the load 132 at a time t1 using the sensor 112 or the like. The sensor 112 may be configured to detect and output a temperature, a voltage, a resistance value, and the like of the load 132. Here, an electric resistance value $R_{HTR}(t1)$ of the load 132 is measured. The process proceeds to step 2614, and the control unit 106 turns off the switch Q2.

The process proceeds to step 2616, and the control unit 106 turns on the switch Q2 again to cause the second circuit 204 to function. The process proceeds to step 2518, and the control unit 106 measures the value related to the temperature of the load 132 at a time t2, e.g., an electric resistance value $R_{HTR}(t2)$ of the load 132. The process proceeds to step 2620, and the control unit 106 turns off the switch Q2 again.

The process proceeds to step 2622, and the control unit 106 obtains a cooling rate of the load 132 based on values of $R_{HTR}(t1)$, $R_{HTR}(t2)$, t1, and t2. Next, in step 2624, the control unit 106 compares the obtained cooling rate with a predetermined threshold. When the cooling rate is smaller than the threshold ("Y" in step 2624), the process proceeds to step 2626, and the control unit 106 determines that the aerosol source is depleted. On the other hand, when the cooling rate is equal to or larger than the threshold ("N" in step 2624), the process proceeds to step 2628, and the control unit 106 determines that the aerosol source sufficiently remains.

Thus, according to the embodiment illustrated in FIG. 26, the control unit 106 is configured to determine whether the depletion of the aerosol source in the storage unit 116A or the aerosol base material 116B has occurred, based on the cooling rate derived from the output value of the sensor 112 in the cooling process after the temperature of the load 132 increases up to a temperature in which the aerosol source can be atomized or higher. The control unit 106 can detect whether the depletion of the aerosol source occurs based on the cooling rate and determine rapidly and with high accuracy whether the depletion of the aerosol source occurs. Note that step 2614 and step 2616 may be skipped so that the switch Q2 that is turned on in step 2610 stays on until step 2620.

In addition, according to the above-described embodiment, the control unit 106 is configured to determine whether the depletion has occurred, based on the cooling rate in a time zone in which a difference between the cooling rate when the depletion of the aerosol source occurs and the cooling rate when the depletion of the aerosol source does not occur is equal to or larger than the threshold (e.g., a time zone corresponding to the region 2302A or 2302B in FIG. 23), in the cooling process. Alternatively, the control unit 106 may be configured to determine whether the depletion has occurred, based on the cooling rate in a time zone in which the temperature of the load 132 belongs to a temperature range achievable only when the depletion occurs (e.g., a time zone corresponding to the region 2302A), in the cooling process. It is determined whether the depletion of the aerosol source occurs, based on the cooling rate derived in a period in which a significant difference in the cooling rate is present. Accordingly, the determination as to whether the depletion occurs can be made with higher accuracy.

In addition, according to the above-described embodiment, the control unit 106 may be configured to derive the cooling rate from a plurality of output values of the sensor 112 and acquire at least the earliest value in terms of the time axis among the plurality of output values of the sensor 112, in the time zone in which the temperature of the load 132 belongs to a temperature range achievable only when the depletion occurs, in the cooling process. Alternatively, the control unit 106 may be configured to acquire the plurality of output values of the sensor 112 in the time zone in which the temperature of the load 132 belongs to a temperature range achievable only when the depletion occurs, in the cooling process. According to these configurations, it is only required that only the start point of the measurement period belong to the region in which the significant difference is present, and therefore the dead zone need not to be set precisely, and furthermore, a microcontroller with high performance such as an extremely fast control cycle need not to be used as the control unit 106.

As already described in connection with the first embodiment of the present disclosure, the load 132 may have the electric resistance value that changes in response to the temperature. The sensor 112 may output the value related to the electric resistance value as the value related to the temperature of the load 132. In this case, since the temperature is derived from the resistance value of the load 132, an expensive dedicated temperature sensor becomes unnecessary. In addition, the control unit 106 may be configured to provide the dead zone in which the value related to the electric resistance value is not acquired by the sensor 112 or the cooling rate is not derived, when or immediately after the cooling process starts. Alternatively, the control unit 106 may be configured to derive the cooling rate based on the output value of the sensor 112 when or immediately after the cooling process starts, the output value being corrected by smoothing the time-series change in the output value of the sensor 112. According to this configuration, since the resistance value when or immediately after the cooling starts is not used, it is less likely to observe fluctuation in the output value of the sensor 112, whereby the observation accuracy of the cooling process is improved.

In an example, the control unit 106 may be configured to control the power supply from the power source 110 to the load 132 so that the electric power supplied from the power source 110 to the load 132 before the cooling process decreases in a stepped manner or decreases gradually. This enables the current flowing through the circuit to be reduced at the end of the aerosol generation stage. Accordingly, a period in which the output value fluctuates due to the above-described surge current and residual current, and the like can be shortened, thereby enabling the observation of the period in which more prominent significant difference in the cooling rate is produced.

In an example, the above-described dead zone may be provided to continue until the current value of at least one of the residual current and the surge current that are generated at the end of the power supply becomes equal to or smaller than the threshold. Therefore, the dead zone becomes longer than the time period until the surge current or the residual current disappears or becomes vanishingly small. Accordingly, the cooling process is not observed in a state in which the residual current or the surge current is superimposed on the output value of the sensor, whereby the observation accuracy is improved.

In an example, the dead zone may be shorter than the time period until the cooling process is completed in the case where the depletion does not occur. Thus, the dead zone is shorter than the cooling time period when the aerosol source is sufficient in quantity. Accordingly, an excessively long dead zone is unnecessary, thereby allowing unimpeded observation of the cooling process.

In an example, at least one of the time period from the end of the power supply to the start of acquisition of the value related to the electric resistance value by the sensor 112 and the cycle in which the sensor 112 acquires the value related to the electric resistance value may be larger than the minimum value achievable by the control unit 106. This can intentionally reduce the number of observation timings or the frequency of the observation, when the cooling process of the load 132 is observed via the resistance value. Accordingly, the cooling process of the load can be observed with high accuracy even without using the dedicated temperature sensor.

FIG. 27 is a flowchart of processing for detecting the depletion of the aerosol source, according to an embodiment of the present disclosure. The processes in steps 2702 and 2704 are the same as the processes in steps 2602 and 2604 in FIG. 26.

The process proceeds to step 2706, and the control unit 106 turns on the switch Q2. The switch Q2 may be turned on immediately after the switch Q1 is turned off. Next, in step 2708, the control unit 106 turns off the switch Q2. The current flowing through the load 132 when the switch Q2 is on is smaller than the current flowing through the load 132 when the switch Q1 is on. Accordingly, the surge current generated after the switch Q2 is turned on and off in steps 2706 and 2708 is smaller than the surge current generated in the example indicated by reference numeral 2502 in FIG. 25, Note that steps 2704 to 2708 may be performed before step 2702. Accordingly, the cooling process can be observed immediately after the start.

The processes in steps 2710 to 2732 are the same as the processes in steps 2606 to 2628.

Figure 27:
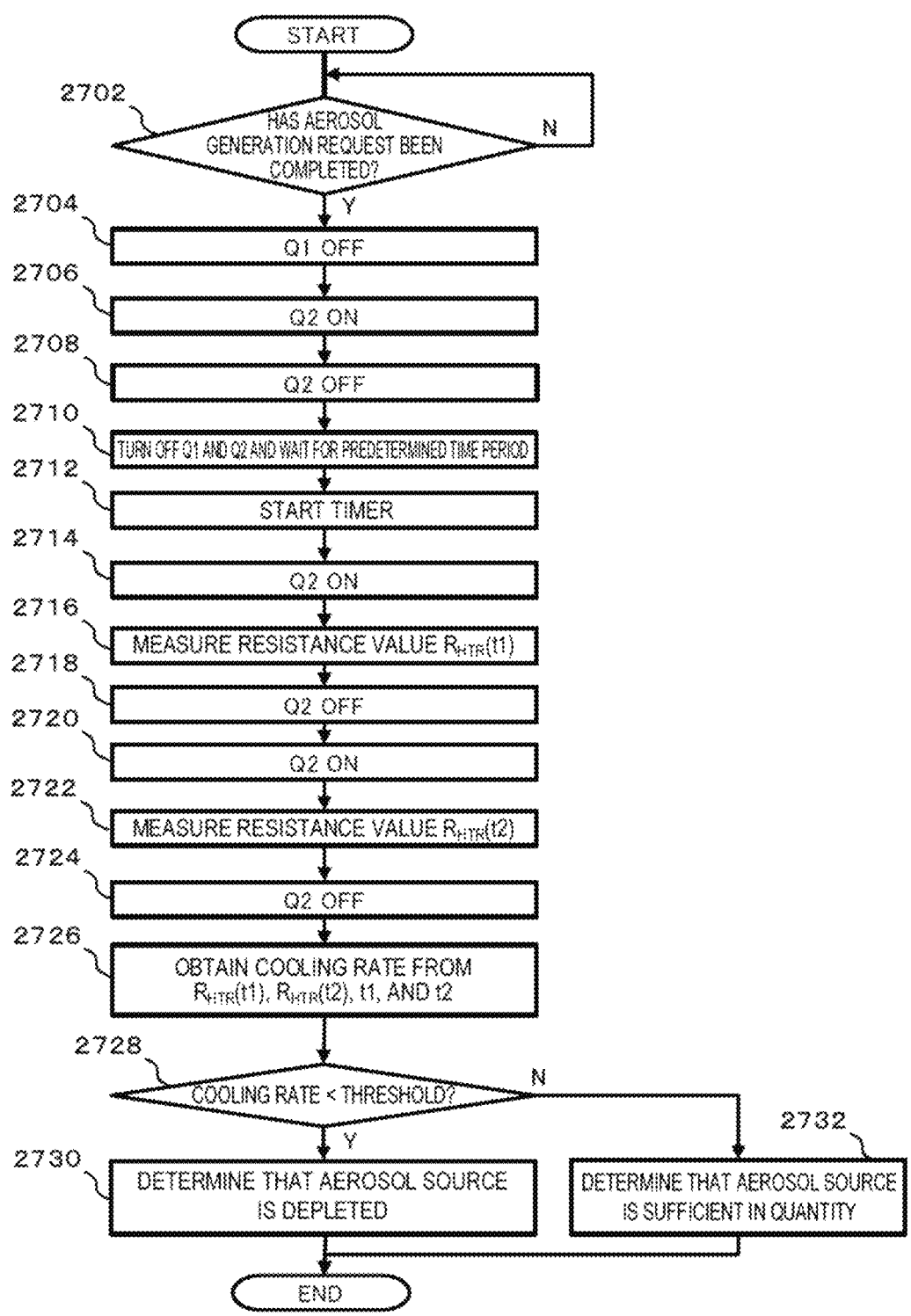
FIG. 27 is a flowchart of processing for detecting the depletion of the aerosol source, according to an embodiment of the present disclosure.

The aerosol generation device according to the second embodiment of the present disclosure may include the circuit 200 illustrated in FIG. 2, in an example. The circuit 200 may include a first circuit 202 that is connected in series between the power source 110 and the load 132 and includes the first switch Q1, and a second circuit 204 that is connected in series between the power source 110 and the load 132, is connected in parallel to the first circuit 202, includes the second switch Q2, and has an electric resistance value larger than that of the first circuit 202. The control unit 106 may be configured to control the first switch Q1 and the second switch Q2, and derive the cooling rate based on the output value of the sensor while only the second switch Q2 of the first switch Q1 and the second switch Q2 is on. This configuration includes a dedicated circuit for measuring a resistance value of a high-resistance resistor. Accordingly, the influence on the cooling process of the load when the resistance value is measured can be reduced. As described in connection with FIG. 27, the control unit 106 may be configured to turn on the second switch Q2 immediately before the cooling process. This alternately turns on the first switch Q1 and the second switch Q2. Accordingly, this can mitigate the surge current and the residual current when the cooling process starts.

Figure 28:
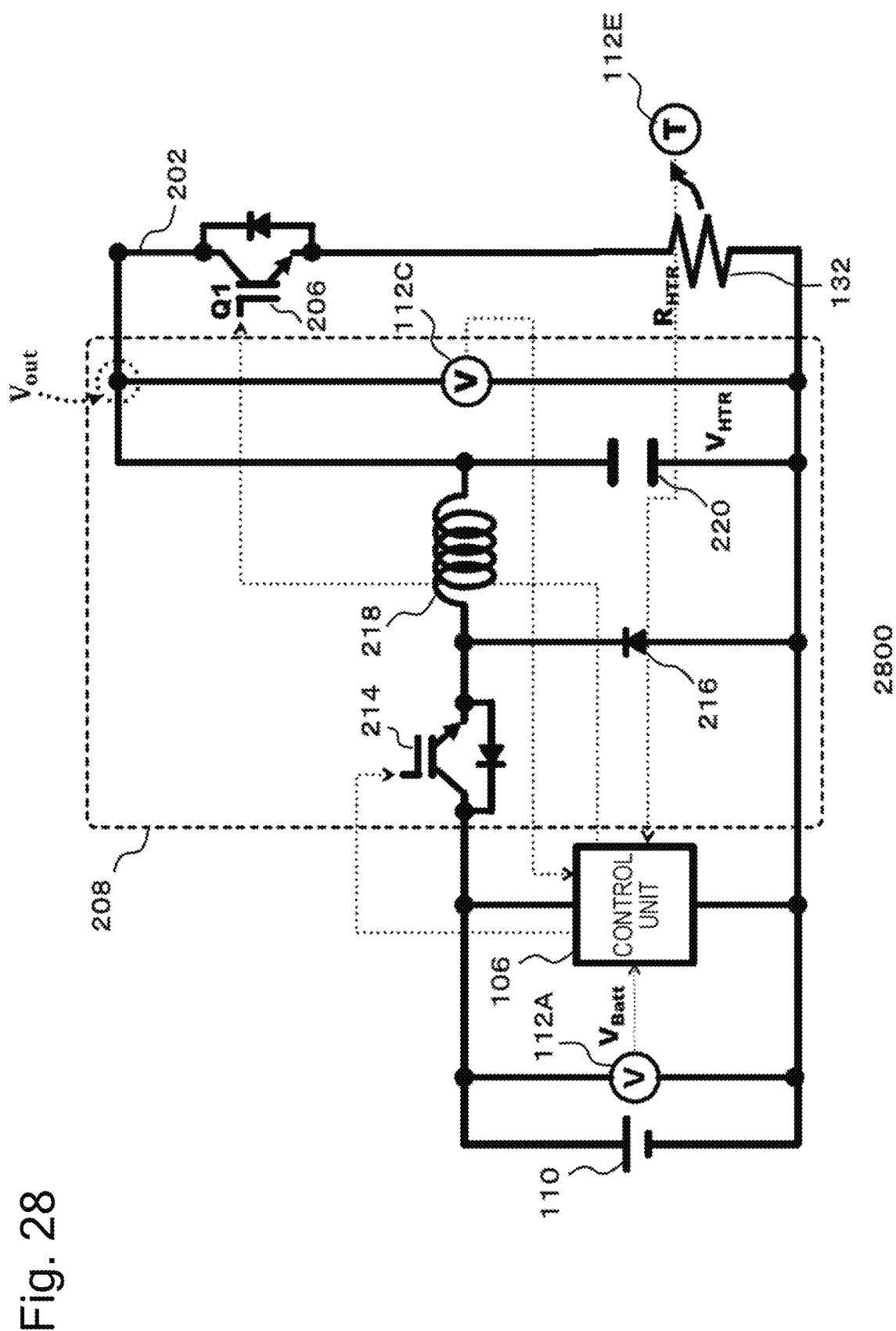
FIG. 28 schematically illustrates a circuit included in the aerosol generation device, according to an embodiment of the present disclosure.

FIG. 28 schematically illustrates a circuit included in the aerosol generation device, according to an embodiment of the present disclosure, A circuit 2800 is different from the circuit 200 in FIG. 2 in that the circuit 2800 does not include the second circuit 204. In the example of FIG. 28, the aerosol generation device may include a temperature sensor 112E that detects and outputs a temperature of the load 132. In this case, for example, the control unit 106 need not perform the processes in steps 2606 to 2622 in FIG. 26, the temperature sensor 112E directly measures the temperatures of the load 132 at the times t1 and t2, and the control unit 106 may obtain the cooling rate based on the measured temperatures.

In still another example, the aerosol generation device may include a circuit having similar configuration to that of the circuit 2800 illustrated in FIG. 28, and may include a voltage sensor 112B that detects a voltage value across the load 132 as illustrated in FIG. 2, instead of the temperature sensor 112E. In this case, the aerosol generation device does not include the switch Q2. The control unit 106 may perform the processing similar to the processing in FIG. 26. Note that in this case, the control unit 106 turns off the switch Q1 and waits for a predetermined time period, instead of performing step 2606. The control unit 106 further turns on the switch Q1 instead of performing steps 2610 and 2616, and turns off the switch Q1 instead of performing steps 2614 and 2620.

In the above description, the second embodiment of the present disclosure has been described as an aerosol generation device and a method of operating the aerosol generation device. However, it will be appreciated that the present disclosure, when being executed by a processor, can be implemented as a program that causes the processor to perform the method or as a computer readable storage medium storing the same program.

Third Embodiment

When the aerosol generation request is issued when the aerosol source in the storage unit 116A or the aerosol base material 116B is depleted, the heater (the load 132) is heated in a state exposed to the atmosphere. Accordingly, the load 132 causes chemical changes depending on the material forming the load 132, and the physical properties thereof may change. In an example, a protective film is formed on a surface of the load 132 by the phenomenon such as oxidation, resulting that the electric resistance value of the load 132 may change. The inventors of the present application arrived at the technical idea in which such a phenomenon such as oxidation is used to detect the occurrence of the depletion of the aerosol source in the aerosol generation device. Hereafter, the present embodiment will be specifically described.

Figure 29:
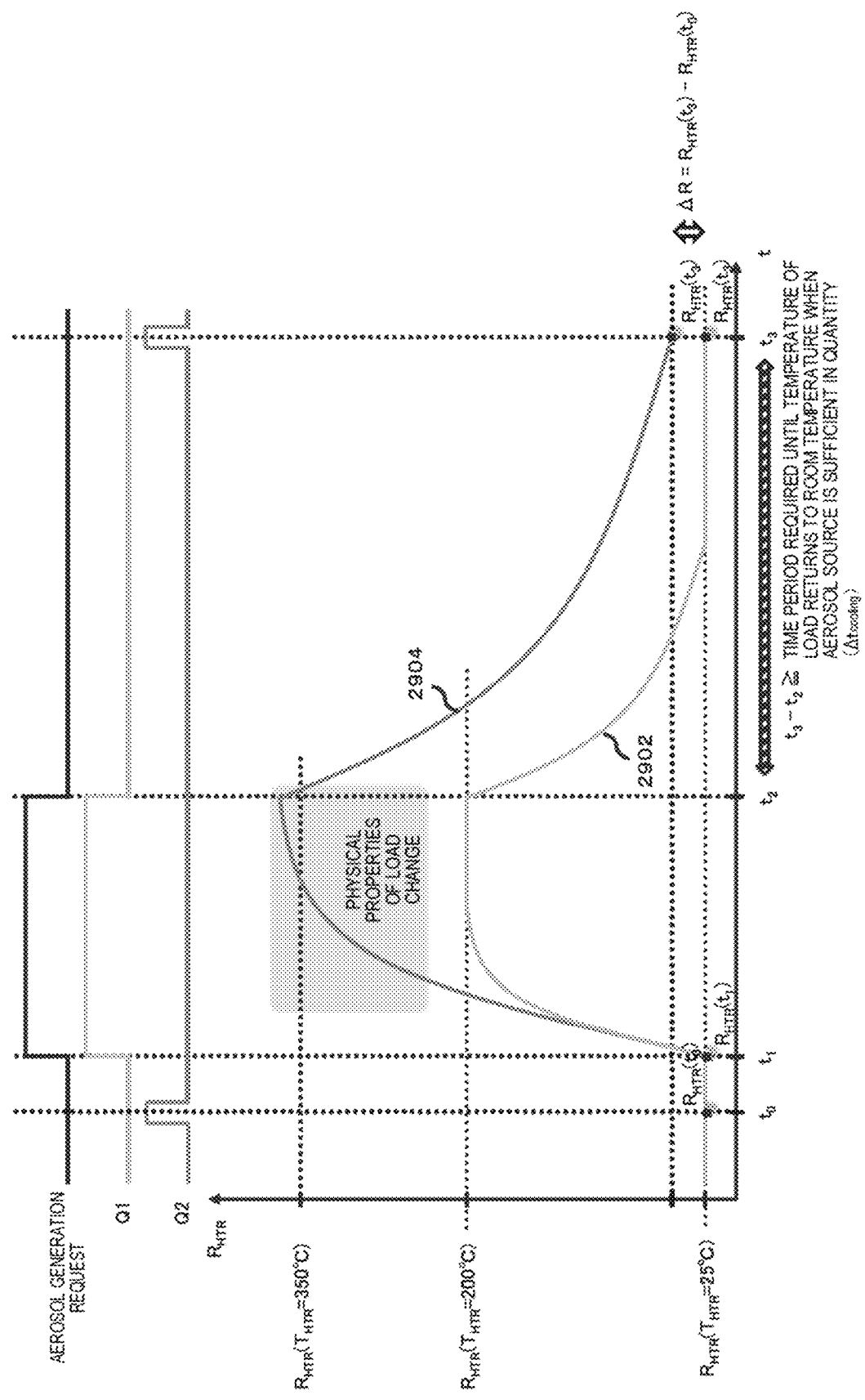
FIG. 29 conceptually shows a method of determining whether the depletion of the aerosol source has occurred, in an embodiment of the present disclosure.

FIG. 29 conceptually shows a method of determining whether the depletion of the aerosol source has occurred, in an embodiment of the present disclosure. The horizontal axis of the graph represents time, and the vertical axis represents an electric resistance value of the load 132. The electric resistance value of the load 132 is merely an example of a value related to the physical properties of the load 132 used in the present embodiment, it will be appreciated by those skilled in the art that the values related to various physical properties of the load 132 that may change due to the depletion of the aerosol source can be used in the present embodiment.

"$R_{HTR}(t_0)$" represents a resistance value of the load 132 at the room temperature (here, 25° C.) (or the steady state) at a time to before the electric power is supplied to the load 132. The "$R_{HTR}(t_0)$" can be measured by turning on the switch Q2 to function the second circuit 204.

In this example, the aerosol generation request is issued at a time $t_1$. The switch Q1 is turned on according to the request, and the power supply to the load 132 is started. As described in connection with the first embodiment and the second embodiment, when the PTC heater is used for the load 132, the resistance value $R_{HTR}$ of the load 132 increases as the temperature of the load 132 increases. A curve 2902 in FIG. 29 shows a change in the resistance value of the load 132 when the aerosol source is sufficient in quantity. A curve 2904 shows a change in the resistance value of the load 132 when the aerosol source is depleted.

In the case where the aerosol source is sufficient in quantity, when the temperature of the load 132 reaches the maximum temperature (here, 200° C.) reached by the aerosol source in the normal state, the resistance value of the load 132 no longer increases, as indicated by the curve 2902. Then, when the aerosol generation request is completed at a time $t_2$ and the switch Q1 is turned off, the temperature of the load 132 decreases, and the resistance value of the load 132 decreases. When the temperature of the load 132 reaches the room temperature (or the steady state), the resistance value returns to the value $R_{HTR}(t_0)$ before heating of the load 132.

In the case where the aerosol source is depleted, when the temperature of the load 132 exceeds the maximum temperature reached by the aerosol source in the normal state, and then further increases to the temperature (e.g., 350° C.) achievable only when the depletion of the aerosol source occurs, as indicated by the curve 2904. At this time, the physical properties of the load 132 may change depending on the material of the load 132. For example, a protective film may be formed on a surface of the load 132. In this example, the temperature of the load 132 at the time $t_2$ has reached up to 350° C. or higher. When the switch Q1 is turned off, the temperature of the load 132 decreases, and the resistance value of the load 132 also decreases accordingly. However, even when the temperature of the load 132 returns to the room temperature (or the steady state) as shown in FIG. 29, the resistance value of the load 132 does not return to the value before heating due to an influence of the changes in the above-described physical properties, and becomes larger than the value before heating. In the present embodiment, it is determined whether the aerosol source is depleted based on whether a difference ΔR between the resistance value $R_{HTR}(t_3)$ of the load 132 at a time $t_3$ and the original resistance value $R_{HTR}(t_0)$ is equal to or larger than a predetermined threshold. Here, "$t_3-t_2$" may be set to be equal to or larger than a time period $\Delta t_{cooling}$ required until the temperature of the load 132 returns to the room temperature (or the steady state) when the aerosol source is sufficient in quantity.

Figure 30:
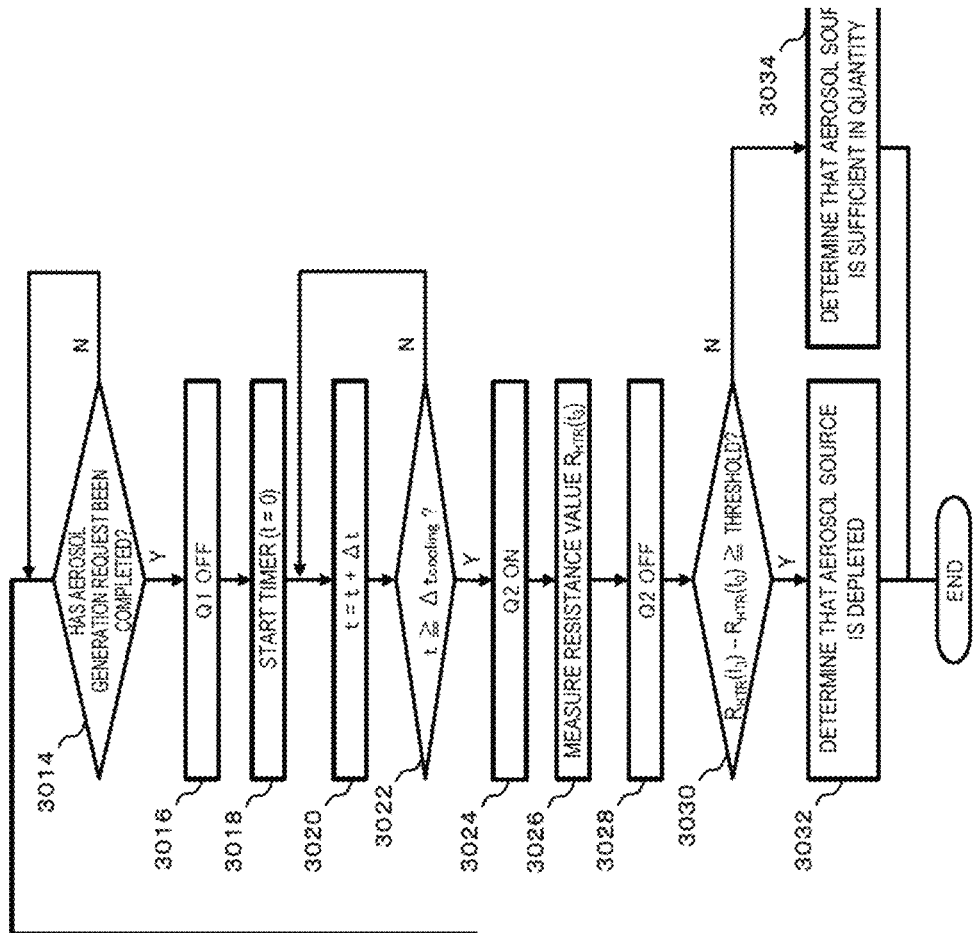
Figure 30:
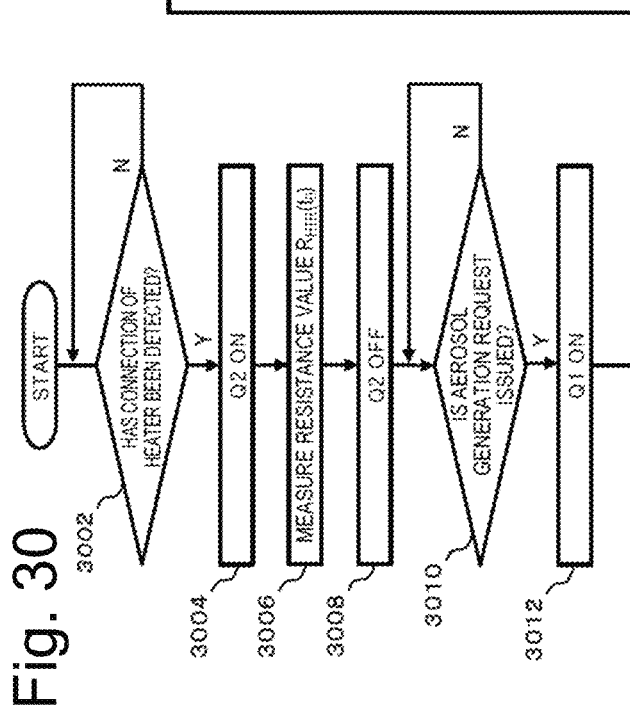

FIG. 30 is a flowchart of processing according to an embodiment of the present disclosure, in connection with FIG. 29. Here, all the steps will be described as being performed by the control unit 106. However, it should be noted that some of the steps may be performed by another component in the aerosol generation device 100.

The process starts at step 3002, and the control unit 106 determines whether the connection of the heater (load) has been detected. For example, when detecting that the cartridge 104A is connected to the main body 102, the control unit 106 determines that the connection of the heater has been detected.

When the connection of the heater is not detected ("N" in step 3002), the process returns to before step 3002. When the connection of the heater has been detected ("Y" ire step 3002), the process proceeds to step 3004. In step 3004, the control unit 106 turns on the switch Q2 to cause the second circuit 204 to function. The timing when the switch Q2 is turned on may be any time point from the time to $t_0$ the time $t_1$ when the aerosol generation is started, as shown in FIG. 28. The timing when the switch Q2 is turned on may be a time point when the aerosol generation request is issued in step 3010 described later.

The process proceeds to step 3006, and the control unit 106 measures a value related to the physical properties of the load 132. For example, the control unit 106 may measure a voltage applied across the load 132 using the voltage sensor, and measure an electric resistance value of the load 132 based on the measured voltage. In the example of FIG. 30, the following description will be made assuming that the resistance value $R_{HTR}(t_0)$ of the load 132 is measured in this manner. The process proceeds to step 3008, and the control unit 106 turns off the switch Q2.

The process proceeds to step 3010, and the control unit 106 determines whether the aerosol generation request is issued. As an example, the control unit 106 may determine whether user's inhalation has been started, based on output of the pressure sensor, and the like. In another example, the control unit 106 may determine whether the button provided in the aerosol generation device 100 to supply the electric power to the load 132 has been pressed. When the aerosol generation request is not issued ("N" in step 3010), the process returns to before step 3010. When the aerosol generation request is issued ("Y" in step 3010), the process proceeds to step 3012. In step 3012, the control unit 106 turns on the switch Q1 to start the power supply to the load 132.

The processes in steps 3014 to 3020 are the same as the processes in steps 402 to 408 in FIG. 4.

The process proceeds to step 3022, and the control unit 106 determines whether the value t of the timer is equal to or larger than $\Delta t_{cooling}$ shown in FIG. 29. When the condition is not satisfied ("N" in step 3022), the process returns to before step 3020. When the condition is satisfied ("Y" in step 3022), the process proceeds to step 3024.

In step 3024, the control unit 106 turns on the switch Q2 to cause the second circuit 204 to function. Next, in step 3026, the control unit 106 measures the resistance value $R_{HTR}(t_3)$ (see FIG. 29) of the load 132. Next, in step 3028, the control unit 106 turns off the switch Q2.

The process proceeds to step 3030, and the control unit 106 determines whether a difference between $R_{HTR}(t_3)$ and $R_{HTR}(t_0)$ is equal to or larger than a predetermined threshold. When the difference is equal to or larger than the threshold ("Y" in step 3030), the process proceeds to step 3032, and the control unit 106 determines that the aerosol source is depleted. On the other hand, when the difference is smaller than the threshold ("N" in step 3030), the process proceeds to step 3034, and the control unit 106 determines that the aerosol source sufficiently remains.

FIG. 31 shows Table 3100 indicating oxidation-reduction potentials and the ease of forming an oxide film of various metals that can be used for manufacturing of the load 132 (heater). The smaller the oxidation-reduction potential is, the easier the formation of the oxide film is. The larger the oxidation-reduction potential is, the less the oxide film is likely to be formed. In Table 3100, "Al" shows that the oxide film is most likely to be formed, and "Au" shows that the oxide film is least likely to be formed. In the present embodiment, a phenomenon in which the physical properties of the load 132 chance at the temperature achievable only when the depletion of the aerosol source occurs is used for detection of the occurrence of depletion of the aerosol source. Accordingly, among the metals shown in Table 3100, Al, Ti, Zr, Ta, Zn, Cr, Fe, Ni, Pb, and Cu that may have the oxide film formed thereon are suitable for manufacturing of the load 132. Accordingly, the load 132 may contain metals having the oxidation-reduction potentials equal to or lower than that of copper. As an example, the load 132 may contain NiCr in the above-described metals. In addition, the load 132 may be configured to have no passivation film formed on the surface thereof not to interfere with oxidation. In other words, it can be said that stainless steel having a passivation film formed on the surface thereof, and the like is unsuitable for manufacturing of the load 132.

Figure 32:
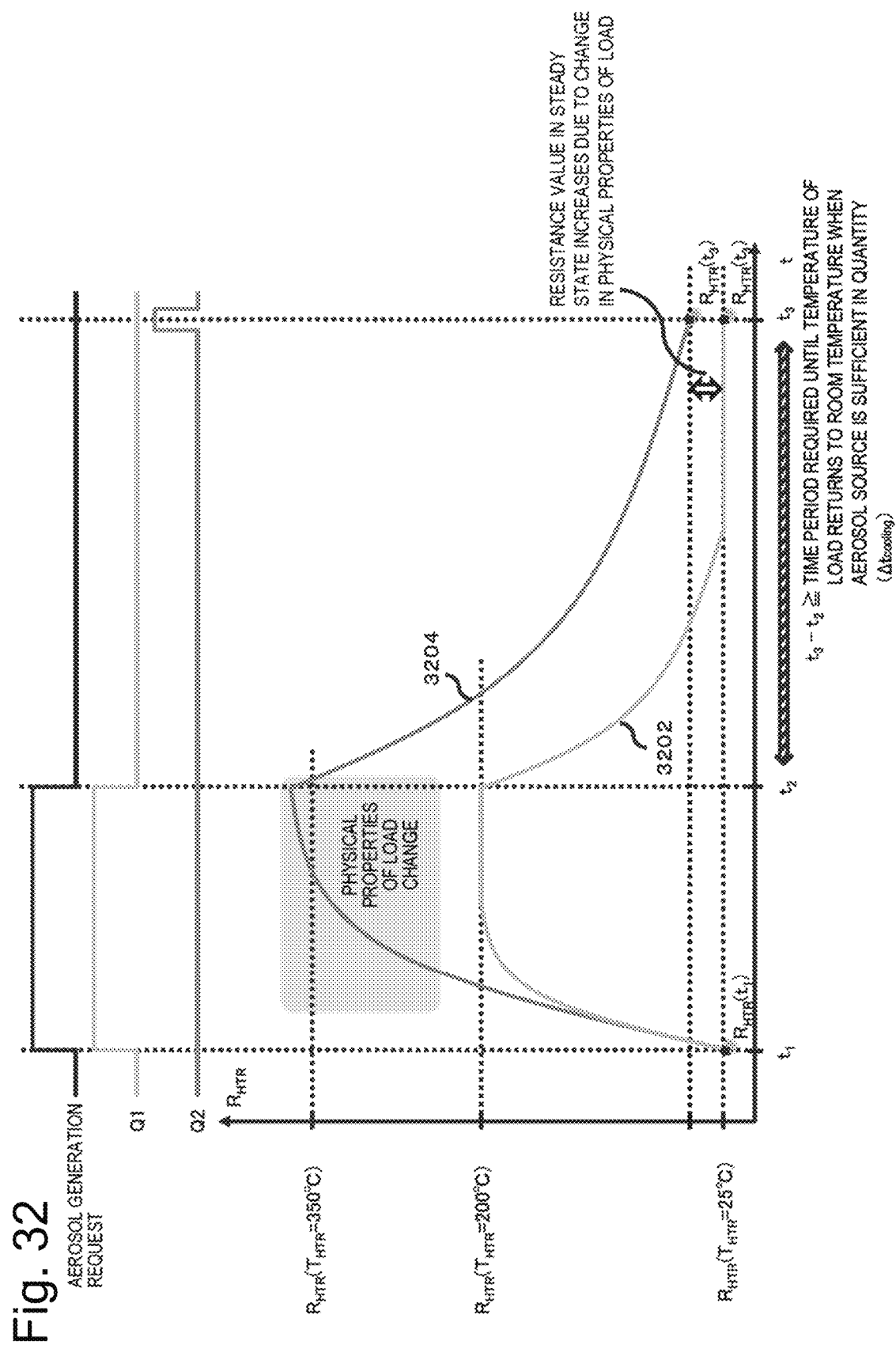

FIG. 32 conceptually shows a method of determining whether the depletion of the aerosol source has occurred, in an embodiment of the present disclosure.

"$R_{HTR}(t_1)$" represents a resistance value of the load 132 at the room temperature (here, 25° C.) (or the steady state) at a time $t_1$ when the switch Q1 is turned on and the power supply to the load 132 is started. A curve 3202 shows a change in the resistance value of the load 132 when the aerosol source is sufficient in quantity. A curve 3204 shows a change in the resistance value of the load 132 when the aerosol source is depleted.

As in the example of FIG. 29, in the case where the aerosol source is sufficient in quantity, when the temperature of the load 132 reaches the maximum temperature (here, 200° C.) reached by the aerosol source in the normal state, the resistance value of the load 132 no longer increases, as indicated by the curve 3202. Then, when the aerosol generation request is completed at a time $t_2$ and the switch Q1 is turned off, the temperature of the load 132 decreases, and the resistance value of the load 132 decreases. The resistance value $R_{HTR}(t_3)$ when the temperature of the load 132 reaches the room temperature (or the steady state) is approximately equal to a value $R_{HTR}(t_1)$ before heating of the load 132.

As in the example of FIG. 29, in the case where the aerosol source is depleted, when the temperature of the load 132 exceeds the maximum temperature reached by the aerosol source in the normal state, and then further increases to the temperature achievable only when the depletion of the aerosol source occurs, as indicated by the curve 3204. At this time, the physical properties of the load 132 may change depending on the material of the load 132. When the switch Q1 is turned off, the temperature of the load 132 decreases, and the resistance value of the load 132 also decreases accordingly. However, even when the temperature of the load 132 returns to the room temperature (or the steady state), the resistance value $R_{HTR}(t_3)$ of the load 132 becomes larger than the value $R_{HTR}(t_1)$ before heating due to an influence of the changes in the physical properties.

Figure 33:
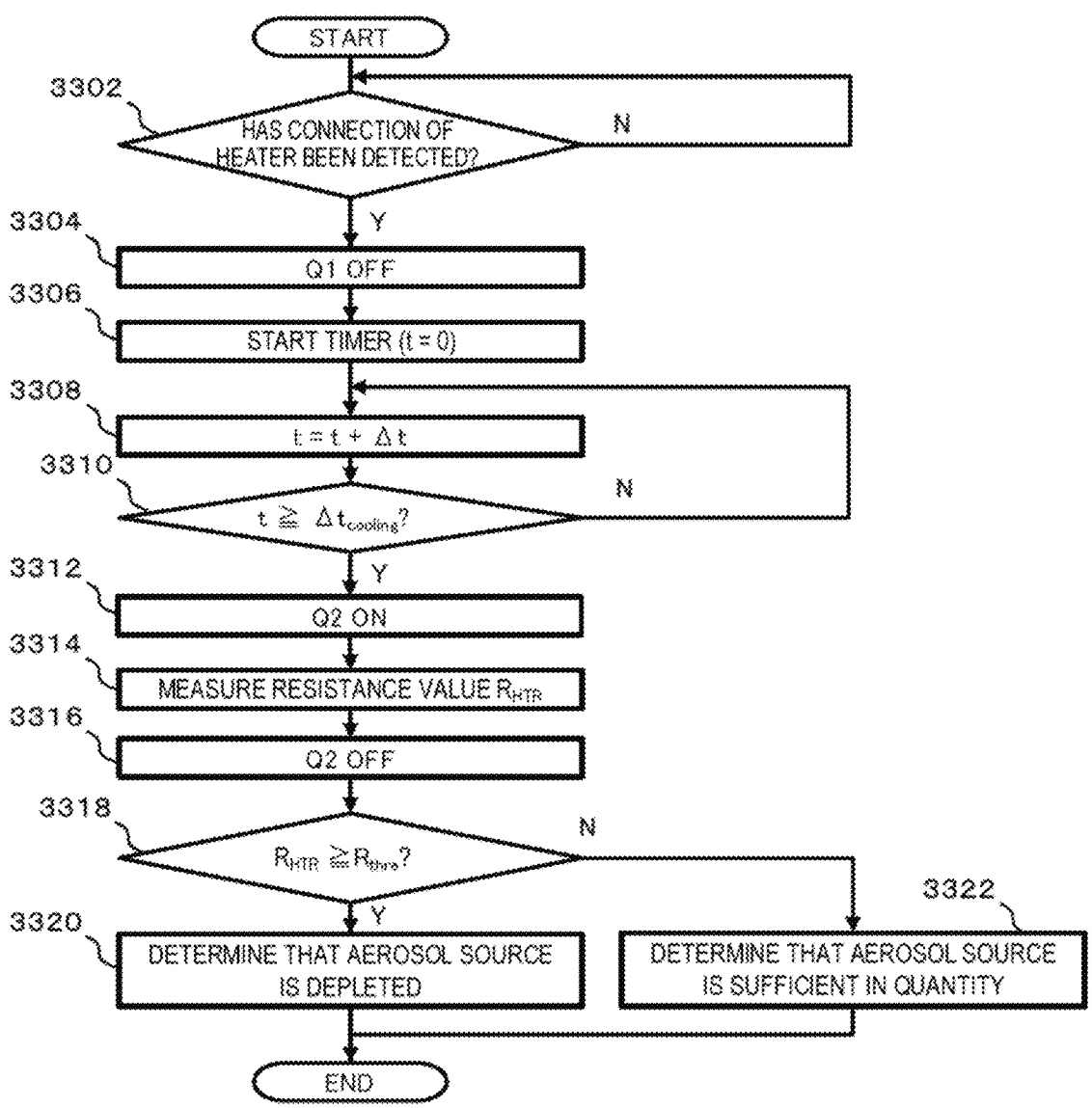

FIG. 33 is a flowchart of processing according to an embodiment of the present disclosure, in connection with FIG. 32. The processes in steps 3302 to 3316 are the same as the processes in steps 3014 to 3028 in FIG. 30.

The process proceeds to step 3318, and the control unit 106 determines whether the resistance value of the load 132 in a state of being returned to the steady state is equal to or larger than a predetermined threshold $R_{thre}$. The threshold $R_{thre}$ is a total value of the resistance value in the steady state when the aerosol source is sufficient in quantity and an increasing amount that is known in advance for the resistance value of the load 132 when the physical properties of the load 132 have changed due to overheating. In other words, the threshold $R_{thre}$ is a resistance value of the load 132 when the physical properties of the load 132 have changed due to overheating. The threshold $R_{thre}$ may be prestored in the memory 114. Instead of the above-described process, in step 3318, the control unit 106 may measure the resistance value at the time $t_1$ in FIG. 32, and determine whether a difference between the resistance value measured at the time $t_3$ and the resistance value measured at the time $t_1$ is equal to or larger than the predetermined threshold. The predetermined threshold may be prestored in the memory. The processes in steps 3320 and 3322 are the same as the processes in steps 3032 and 3034.

In the embodiment of FIG. 29 and FIG. 30 and the embodiment of FIG. 32 and FIG. 33, when the aerosol generation request is issued again before the temperature of the load 132 decreases to the room temperature or the steady state during cooling of the load 132, the temperature and the resistance value of the load 132 increases again. In this case, it becomes difficult to determine accurately whether the aerosol source is depleted, in the processing in FIG. 30 or FIG. 33. As a solution to this problem, the control unit 106 may prohibit the aerosol source from being atomized by the load 132 until the resistance value of the load 132 is returned to the steady state. As an example, even when the aerosol generation request is issued during $\Delta t_{cooling}$ indicated in FIG. 29 and FIG. 32, the control unit 106 need not to respond to the request.

Figure 34:
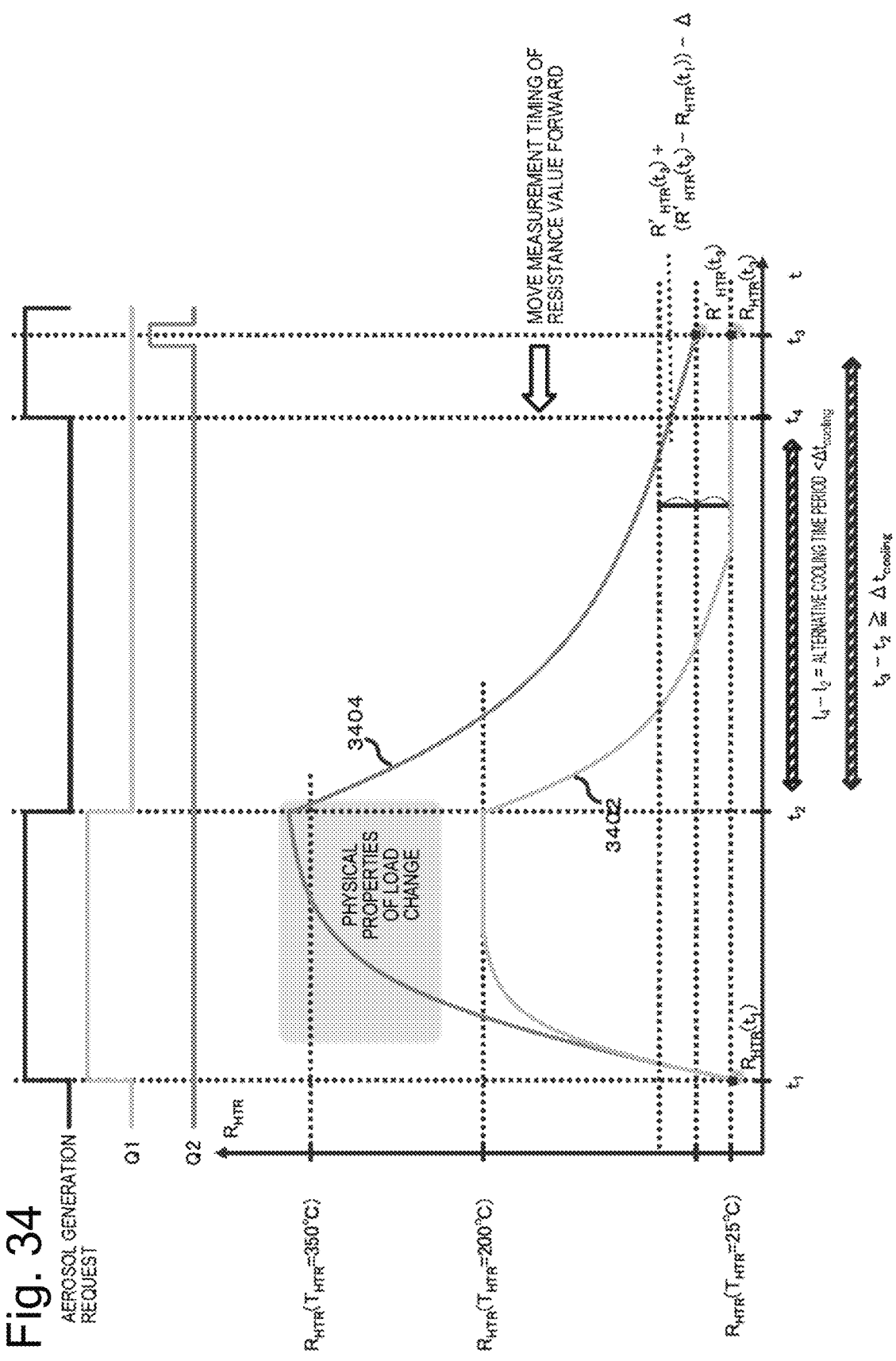

FIG. 34 conceptually shows a method of determining whether the depletion of the aerosol source has occurred, in an embodiment of the present disclosure. Unlike the case of FIG. 32, in this example, the control unit 106 measures the resistance value of the load 132 at a time $t_4$ before a time $t_3$, and determines whether the aerosol source is depleted. The time $t_4$ is a time point prior to a time point when the temperature of the load 132 decreases to the steady state after the temperature of the load 132 increases up to a temperature in which the aerosol source can be atomized or higher, in the case where the aerosol source is depleted.

Figure 35:
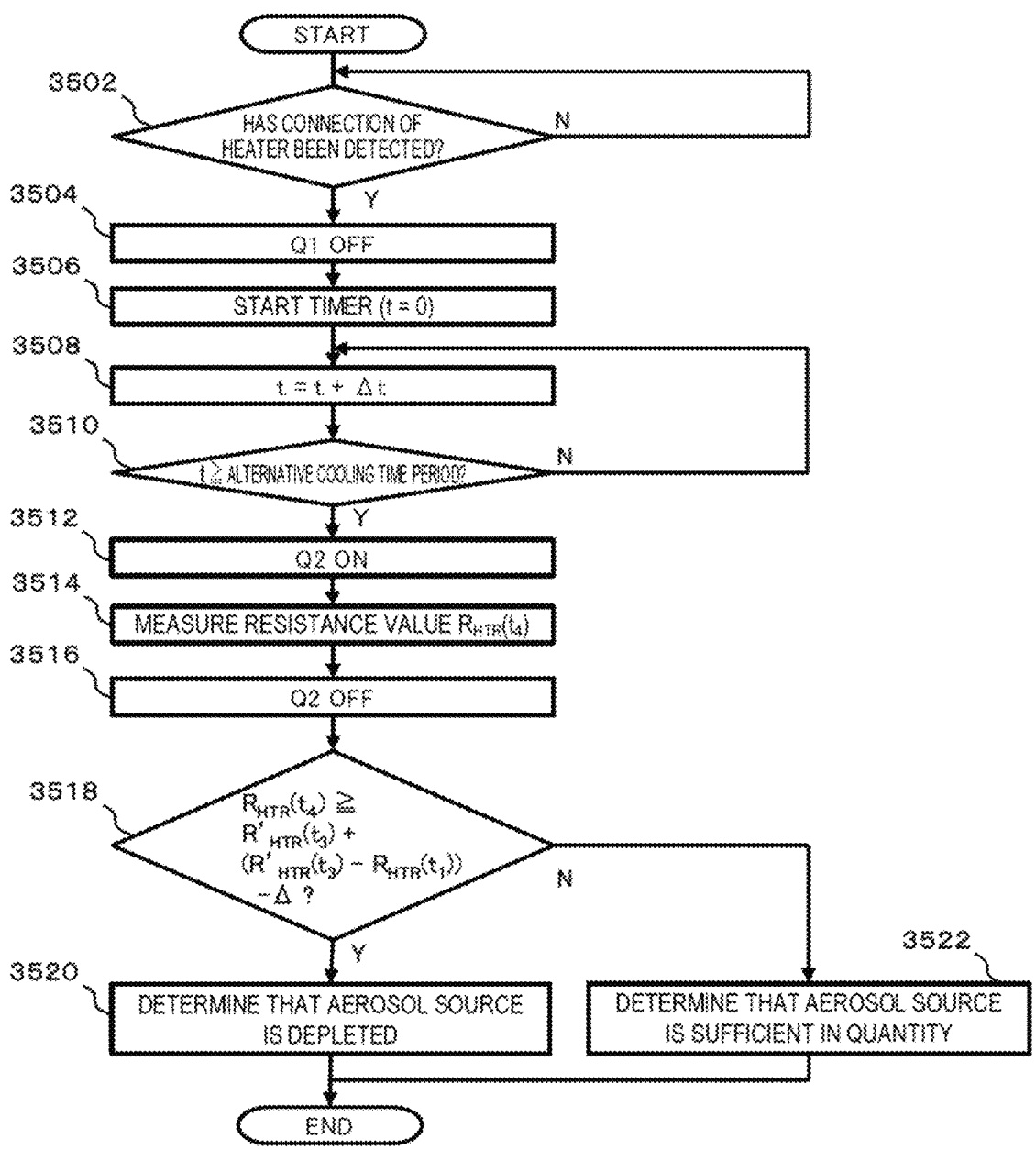

FIG. 35 is a flowchart of processing according to an embodiment of the present disclosure, in connection with FIG. 32. The processes in steps 3502 to 3508 are the same as the processes in steps 3302 to 3308 in FIG. 33.

The process proceeds to step 3510, and the control unit 106 determines whether the value t of the timer is equal to or larger than an alternative cooling time period shown in FIG. 34. When the condition is not satisfied ("N" in step 3510), the process returns to before step 3508. When the condition is satisfied ("Y" in step 3510), the process proceeds to step 3512. The processes in steps 3512 to 3516 are the same as the processes in steps 3312 to 3316 in FIG. 33.

The process proceeds to step 3518, and the control unit 106 determines whether a resistance value $R_{HTR}(t_4)$ of the load 132 measured in step 3514 is equal to or larger than a predetermined value. The predetermined value may be $R'_{HTR}(t_3)+(R'_{HTR}(t_3)-R_{HT}R((t_1))-\Delta$ (see FIG. 34) as an example. This reflects the fact that a resolution of the resistance value of the load 132 by the sensor 112 must be smaller than $R_{HTR}(t_3)-R_{HT}R(t_1)$, and $\Delta$ as a correction term. That is, the resistance value of the load 132 before reaching the steady state is compared to a value obtained by adding the predetermined value to the resistance value of the load 132 in the steady state when the depletion has occurred. The latter value may be prestored in the memory 114. Alternatively, a value obtained by subtracting the predetermined value from the resistance value of the load 132 before reaching the steady state may be compared to the resistance value of the load 132 in the steady state when the depletion has occurred.

When the condition is satisfied ("Y" in step 3518), the process proceeds to step 3520, and the control unit 106 determines that the aerosol source is depleted. When the condition is not satisfied ("N" in step 3518), the process proceeds to step 3522, and the control unit 106 determines that the aerosol source sufficiently remains.

As described above, the aerosol generation device according to the third embodiment of the present disclosure includes the load 132 of which physical properties change when the load 132 is heated at the temperature achievable only when the depletion of the aerosol source in the storage unit 116A or the aerosol base material 116B occurs. The value related to the physical properties of the load 132 is output by the sensor 112. The control unit 106 may be configured to determine whether the depletion has occurred, based on the output value of the sensor 112 after the temperature of the load 132 increases up to a temperature in which the aerosol source can be atomized or higher. This enables the depletion of the aerosol source to be detected based on the changes in the physical properties of the load 132 due to the depletion of the aerosol source. Accordingly, the occurrent of depletion of the aerosol source can be detected with high accuracy.

In addition, as described above, the control unit 106 may be configured to determine whether the depletion has occurred, based on the output value of the sensor 112 after the temperature of the load 132 increases up to a temperature in which the aerosol source can be atomized or higher. This enables the depletion of the aerosol source to be detected based on the physical properties of the load 132 in the steady state. Accordingly, the possibility of false detection is reduced.

In addition, as described above, the control unit 106 may be configured to determine whether the depletion has occurred, based on an amount of change in the output value of the sensor 112 before and after the temperature of the load 132 increases up to a temperature in which the aerosol source can be atomized or higher. This enables the depletion of the aerosol source to be detected based on the amount of change in the physical properties of the load 132 before and after the power supply to the load 132. Accordingly, the determination is less likely to be affected by the individual differences of the load as compared to the case where the physical properties after the end of the power supply are compared to the threshold.

In addition, as described above, the control unit 106 may be configured to determine whether the depletion has occurred, based on a difference in the output value of the sensor 112 before and after the temperature of the load 132 increases up to a temperature in which the aerosol source can be atomized or higher. This enables the depletion of the aerosol source to be detected based on the amount of change in the physical properties in the steady state before and after the power supply. Accordingly, the determination is less likely to be affected by the individual differences of the load 132 as compared to the case where the physical properties after the end of the power supply are compared to the threshold.

In addition, as described above, the control unit 106 may be configured to prohibit the aerosol source from being atomized by the load 132 until the output value of the sensor 112 reaches the steady state after the temperature of the load 132 increases up to a temperature in which the aerosol source can be atomized or higher. Thus, an interval until the steady state is reached is defined. Accordingly, the frequency of determining the depletion of the aerosol source can be increased.

In addition, as described above, the control unit 106 may be configured to determine whether the depletion has occurred, based on a comparison between the output value of sensor 112 before reaching the steady state and a value obtained by adding the predetermined value to the value related to the physical properties of the load 132 in the steady state when the depletion has occurred, in the cooling process after the temperature of the load 132 increases up to a temperature in which the aerosol source can be atomized or higher. Alternatively, the control unit 106 may be configured to determine whether the depletion has occurred, based on a comparison between a value obtained by subtracting the predetermined value from the output value of the sensor 112 before reaching the steady state and a value related to the physical properties of the load 132 in the steady state when the depletion has occurred, in the cooling process after the temperature of the load 132 increases up to a temperature in which the aerosol source can be atomized or higher. In this way, the physical properties of the load 132 are measured at a time point prior to a time point when the steady state is reached. Accordingly, this makes it possible to specify earlier that the depletion of the aerosol source has occurred.

In addition, as described above, the sensor may output a value related to the electric resistance value of the load 132, as a value related to the physical properties of the load 132. Thus, the temperature is derived from the resistance value of the load. Accordingly, an expensive dedicated temperature sensor becomes unnecessary.

In addition, as described above, the control unit 106 may be configured to determine whether the depletion has occurred, based on a comparison between an output value of the sensor 112 after the temperature of the load 132 increases up to a temperature in which the aerosol source can be atomized or higher and a value related to the resistance value of the load 132 when the protective film e.g., an oxide film) is formed on the surface of the load 132. In addition, as described above, the control unit 106 may be configured to determine whether the depletion has occurred, based on a comparison between an amount of change in the output value of the sensor 112 before and after the temperature of the load 132 increases up to a temperature in which the aerosol source can be atomized or higher and an amount of change in a value related to the resistance value of the load 132 due to the protective film formed on the surface of the load 132. In these cases, a value corresponding to a value of the protective film portion is regarded as a threshold. The threshold may be prestored in the memory 114. Accordingly, this makes it possible to properly detect a change in the resistance value due to formation of the protective film, i.e., the occurrence of depletion of the aerosol source.

The aerosol generation device according to the third embodiment of the present disclosure may include the circuit 200 illustrated in FIG. 2, in an example. The circuit 200 may include a first circuit 202 that is connected in series between the power source 110 and the load 132 and includes the first switch Q1, and a second circuit 204 that is connected in series between the power source 110 and the load 132, is connected in parallel to the first circuit 202, includes the second switch Q2, and has an electric resistance value larger than that of the first circuit 202. The control unit 106 may be configured to control the first switch Q1 and the second switch Q2, and determine whether the depletion has occurred based on the output value of the sensor while only the second switch Q2 of the first switch Q1 and the second switch Q2 is on. This configuration includes a dedicated circuit for measuring a resistance value of a high-resistance resistor. Accordingly, the influence on the cooling process of the load when the resistance value is measured can be reduced.

In the above description, the third embodiment of the present disclosure has been described as an aerosol generation device and a method of operating the aerosol generation device. However, it will be appreciated that the present disclosure, when being executed by a processor, can be implemented as a program that causes the processor to perform the method or as a computer readable storage medium storing the same program.

The embodiments of the present disclosure have been described thus far, and it should be understood that these embodiments are only illustration, and do not limit the scope of the present disclosure. It should be understood that modification, addition, alteration and the like of the embodiments can be properly performed without departing from the gist and the scope of the present disclosure. The scope of the present disclosure should not be limited by any of the aforementioned embodiments, but should be specified by only the claims and the equivalents of the claims.

REFERENCE SIGNS LIST 100A, 100B . . . aerosol generation device, 102 . . . main body, 104A . . . cartridge, 104B . . . aerosol generating article, 106 . . . control unit, 108 . . . notifying unit, 110 . . . power source, 112 . . . sensor, 114 . . . memory, 116A . . . storage unit, 116B . . . aerosol base material, 118A, 118B . . . atomizing unit, 120 . . . air intake channel, 121 . . . aerosol flow path, 122 . . . mouthpiece unit, 130 . . . retention unit, 132 . . . load, 134 . . . circuit, 200 . . . circuit, 202 . . . first circuit, 204 . . . second circuit, 208 . . . conversion part, 217 . . . shunt resistor

The invention claimed is:

1. An aerosol generation device, comprising:
a storage configured to store an aerosol source or an aerosol base material that retains the aerosol source;
a load configured to generate heat upon receipt of power supply from a power source and atomizes the aerosol source;
a sensor configured to output a value related to a temperature of the load; and
a controller configured to determine that depletion of the aerosol source in the storage or the aerosol base material has occurred, based on a cooling rate derived from the output value of the sensor in a cooling process after the temperature of the load increases up to a temperature in which the aerosol source can be atomized or higher, wherein
the cooling rate in the cooling process is greater in a case that the depletion of the aerosol source occurs than in a case that the depletion of the aerosol source does not occur.

2. The aerosol generation device according to claim 1, wherein
the controller is configured to determine whether the depletion has occurred, based on the cooling rate in a time zone in which a difference between the cooling rate when the depletion of the aerosol source occurs and the cooling rate when the depletion of the aerosol source does not occur is equal to or larger than a threshold, in the cooling process.

3. The aerosol generation device according to claim 1, wherein
the controller is configured to determine whether the depletion has occurred, based on the cooling rate in a time zone in which the temperature of the load belongs to a temperature range achievable only when the depletion occurs, in the cooling process.

4. The aerosol generation device according to claim 1, wherein the controller is configured to
derive the cooling rate from a plurality of output values of the sensor, and
acquire at least an earliest value in terms of a time axis among the plurality of output values of the sensor, in a time zone in which the temperature of the load belongs to a temperature range achievable only when the depletion occurs, in the cooling process.

5. The aerosol generation device according to claim 4, wherein
the controller is configured to acquire the plurality of output values of the sensor in the time zone in which the temperature of the load belongs to the temperature range achievable only when the depletion occurs, in the cooling process.

6. The aerosol generation device according to claim 1, wherein
the load has an electric resistance value that changes in response to a temperature, and
the sensor is configured to output the value related to the electric resistance value as a value related to the temperature of the load.

7. The aerosol generation device according to claim 6, wherein
the controller is configured to provide a dead zone in which the value related to the electric resistance value is not acquired by the sensor or the cooling rate is not derived, when or immediately after the cooling process starts, or is configured to derive the cooling rate based on the output value of the sensor when or immediately after the cooling process starts, the output value being corrected by smoothing a time-series change in the output value of the sensor.

8. The aerosol generation device according to claim 7, wherein
the controller is configured to control the power supply from the power source to the load so that the electric power supplied from the power source to the load before the cooling process decreases in a stepped manner or decreases gradually.

9. The aerosol generation device according to claim 7, wherein
the controller is configured to control the power supply from the power source to the load based on a request for aerosol generation, and
the dead zone is provided to continue until a current value of at least one of a residual current and a surge current that are generated at an end of the power supply becomes equal to or smaller than a threshold.

10. The aerosol generation device according to claim 7, wherein
the dead zone is shorter than a time period until the cooling process is completed in a case where the depletion does not occur.

11. The aerosol generation device according to claim 6, comprising:
a first circuit that is connected in series between the power source and the load and includes a first switch; and
a second circuit that is connected in series between the power source and the load, is connected in parallel to the first circuit, includes a second switch, and has an electric resistance value larger than the electric resistance value of the first circuit, wherein
the controller is configured to
control the first switch and the second switch, and
derive the cooling rate based on the output value of the sensor while only the second switch of the first switch and the second switch is on.

12. The aerosol generation device according to claim 11, wherein
the controller is configured to turn on the second switch immediately before the cooling process.

13. The aerosol generation device according to claim 6, wherein
at least one of a time period from the end of the power supply to a start of acquisition of the value related to the electric resistance value by the sensor and a cycle in which the sensor acquires the value related to the electric resistance value is larger than the minimum value achievable by the controller.

* * * * *